(12) United States Patent
Giannoukakis et al.

(10) Patent No.: US 10,940,164 B2
(45) Date of Patent: **\*Mar. 9, 2021**

(54) MICROSPHERE-BASED DELIVERY AND EX VIVO MANIPULATION OF DENDRITIC CELLS FOR AUTOIMMUNE THERAPIES

(71) Applicant: University of Pittsburgh—Of the Commonwealth System of Higher Education, Pittsburgh, PA (US)

(72) Inventors: Nick Giannoukakis, Coraopolis, PA (US); Massimo M. Trucco, Pittsburgh, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 100 days.

This patent is subject to a terminal disclaimer.

(21) Appl. No.: 16/297,484

(22) Filed: Mar. 8, 2019

(65) Prior Publication Data

US 2019/0321398 A1 Oct. 24, 2019

Related U.S. Application Data

(63) Continuation of application No. 15/635,007, filed on Jun. 27, 2017, now Pat. No. 10,272,112, which is a continuation of application No. 14/546,755, filed on Nov. 18, 2014, now Pat. No. 9,724,365.

(60) Provisional application No. 61/905,787, filed on Nov. 18, 2013.

(51) Int. Cl.
| A61K 35/15 | (2015.01) |
| C12N 5/0784 | (2010.01) |
| A61K 9/00 | (2006.01) |
| C12N 15/113 | (2010.01) |

(52) U.S. Cl.
CPC ............ *A61K 35/15* (2013.01); *A61K 9/0019* (2013.01); *C12N 5/064* (2013.01); *C12N 15/1138* (2013.01); *C12N 2310/11* (2013.01); *C12N 2501/52* (2013.01)

(58) Field of Classification Search
CPC ......... A61K 35/15; A61P 37/08; C12N 5/064; C12N 15/1138; C12N 2310/11; C12N 2501/52
USPC ...... 424/9.1; 435/6.1, 91.1, 91.31, 455, 458; 514/44 A; 536/23.1, 24.5
See application file for complete search history.

(56) References Cited

U.S. PATENT DOCUMENTS

| 6,475,483 | B1 | 11/2002 | Steinman et al. |
| 6,936,468 | B2 | 8/2005 | Robbins et al. |
| 7,884,085 | B2 | 2/2011 | Brown et al. |
| 7,964,574 | B2 | 6/2011 | Brown et al. |
| 8,022,046 | B2 | 9/2011 | Brown et al. |
| 8,389,493 | B2 | 3/2013 | Brown et al. |
| 9,724,365 | B2 * | 8/2017 | Giannoukakis ......... A61P 29/00 |
| 10,272,112 | B2 * | 4/2019 | Giannoukakis ......... A61P 29/00 |
| 2010/0260855 | A1 | 10/2010 | Brown et al. |
| 2014/0248212 | A1 | 9/2014 | Radu et al. |

FOREIGN PATENT DOCUMENTS

| CN | 103 074 299 A | 5/2013 |
| WO | WO 1993/20185 | 4/1993 |
| WO | WO 2001/083713 A2 | 11/2001 |
| WO | WO 2003/104456 A1 | 12/2003 |
| WO | WO 2008/019346 A2 | 2/2008 |
| WO | WO 2009/129544 A1 | 10/2009 |
| WO | WO 2011/109833 A2 | 9/2011 |
| WO | WO 2012/054920 A2 | 4/2012 |
| WO | WO 2013/010998 A2 | 1/2014 |

OTHER PUBLICATIONS

Giannoukakis et al., "Phase I (Safety) Study of Autologous Tolerogenic Dendritic Cells in Type 1 Diabetic Patients," *Diabetes Care* 34:2026-2032 (2011).
International Search Report from PCT Application No. PCT/US2014/066186 6 pages (dated Apr. 1, 2015).
Kriegel et al., "Pancreatic islet expression of chemokine CCL2 suppresses autoimmune diabetes via tolerogenic CD11c+CD11b+ dendritic cells," *PNAS* 109(9): 3457-3462 (Feb. 28, 2012).
Phillips et al., "A Microsphere-Based Vaccine Prevents and Reverses New-Onset Autoimmune Diabetes," *Diabetes* 57:1544-1555 (2008).
Written Opinion from PCT Application No. PCT/US2014/066186 7 pages (dated Apr. 1, 2015).

\* cited by examiner

*Primary Examiner* — Jane J Zara
(74) *Attorney, Agent, or Firm* — Klarquist Sparkman, LLP

(57) ABSTRACT

The present invention relates to tolerogenic mammalian dendritic cells (iDCs) and methods for the production of tolerogenic DCs. In addition, the present invention provides methods for administration of tolerogenic dendritic cells as well as particles containing oligonucleotides to mammalian subjects. Enhanced tolerogenicity in a host can be useful for treating inflammatory and autoimmune related diseases, such as type 1 diabetes.

20 Claims, 49 Drawing Sheets
Specification includes a Sequence Listing.

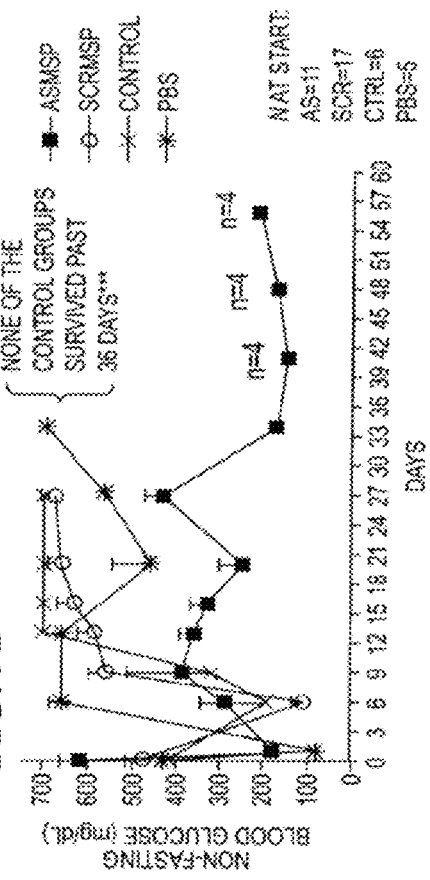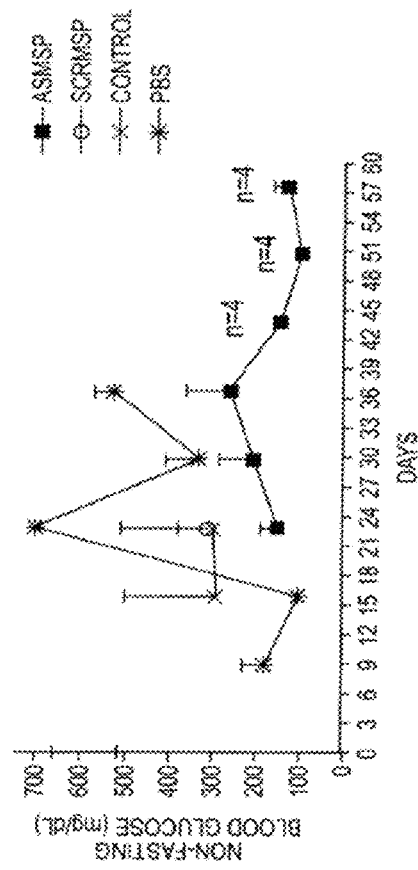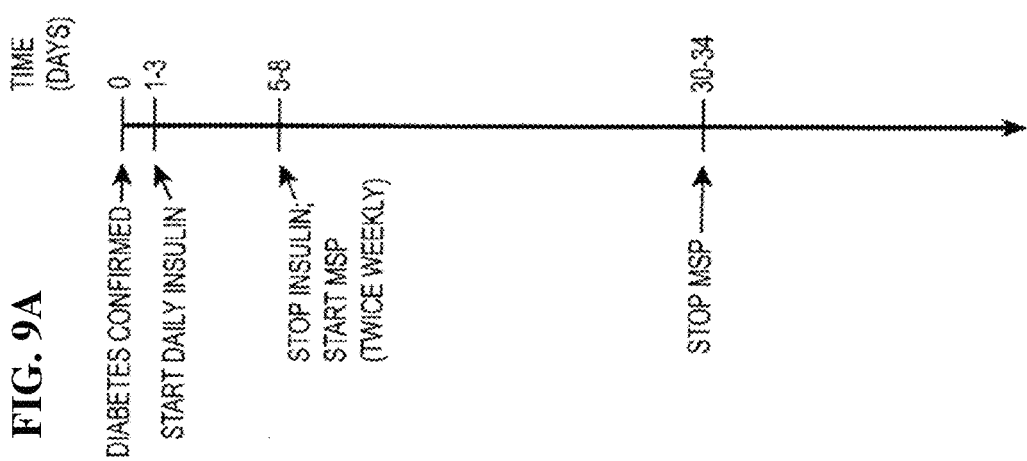
FIG. 9A
FIG. 9B
FIG. 9C

FIG. 15A Accumulation of ASMSP into visceral organs of rhesus monkeys
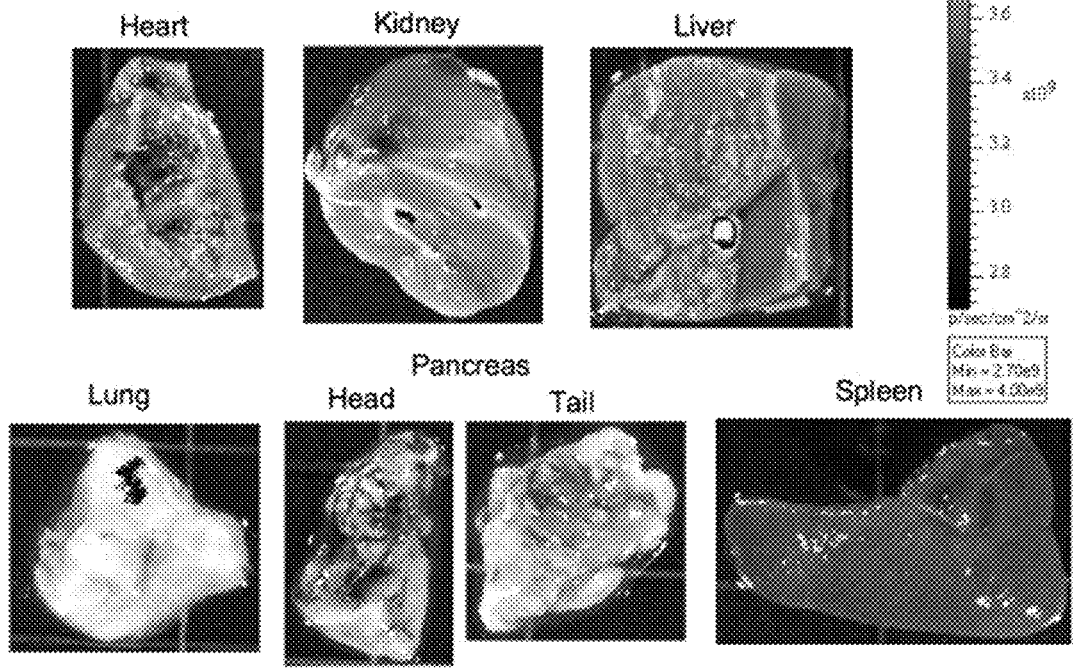
FIG. 15B
Accumulation of fluorescent MSP into the pancreatic lymph nodes of rhesus monkeys
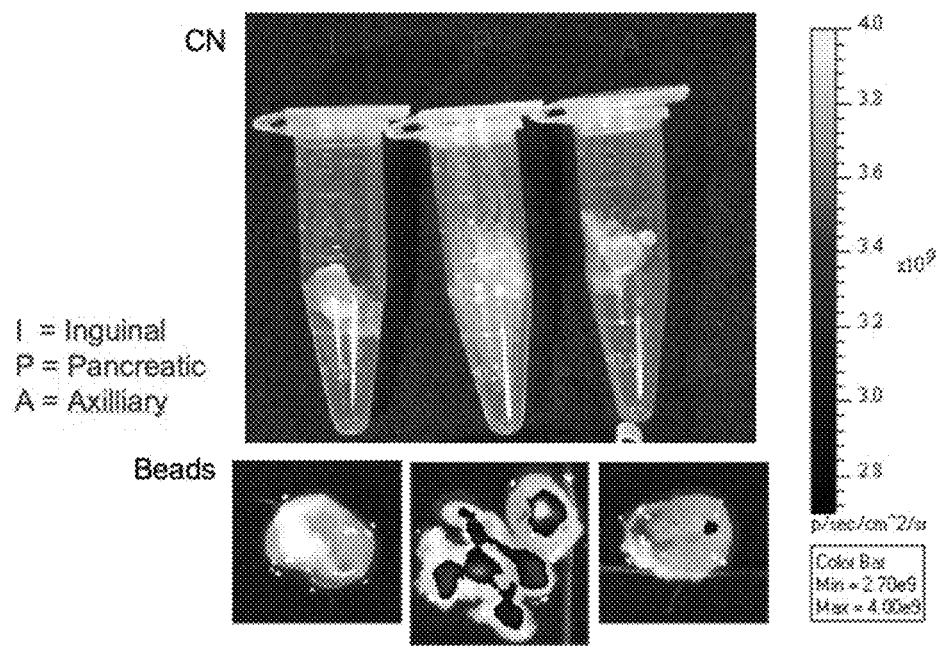

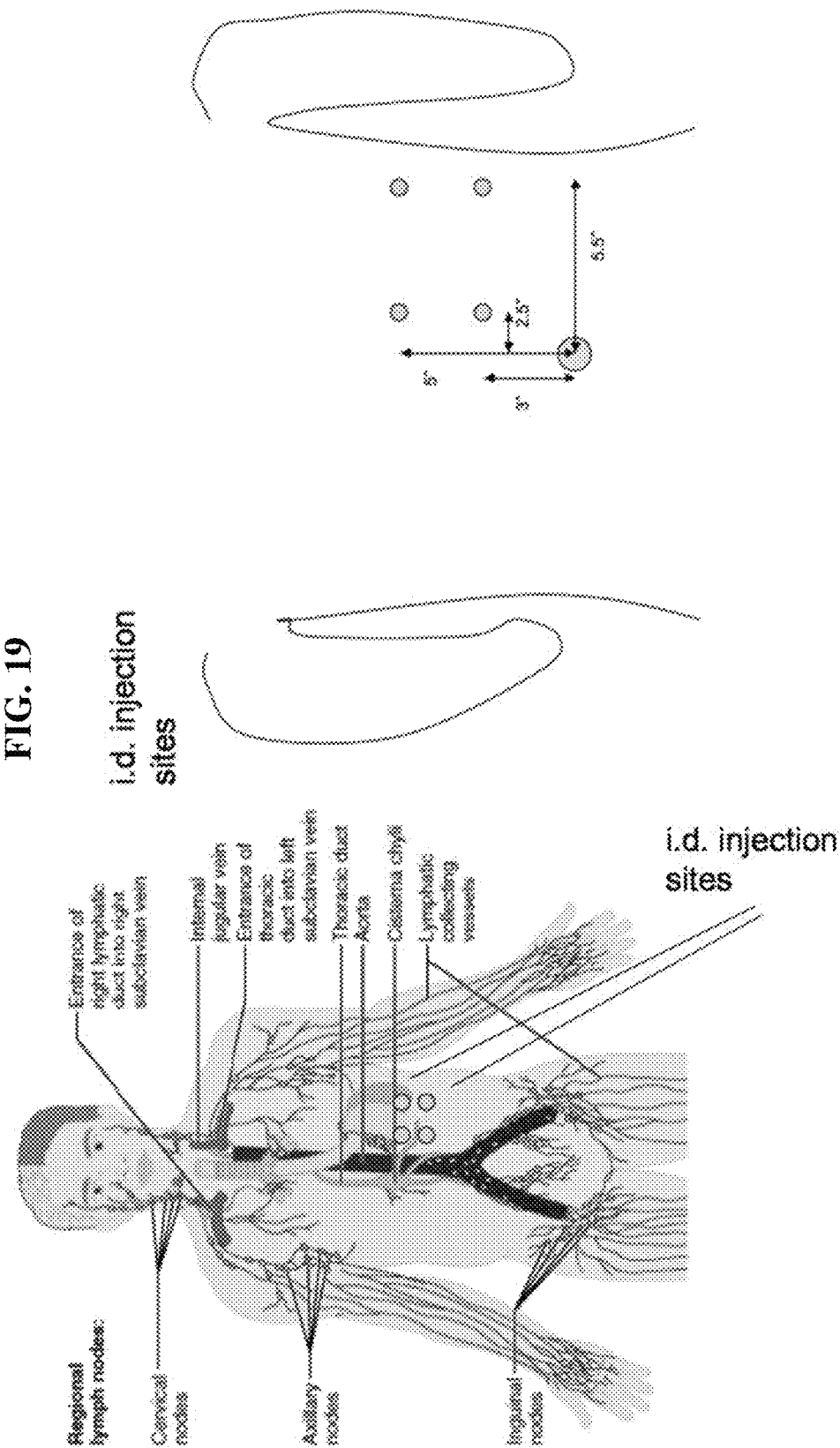

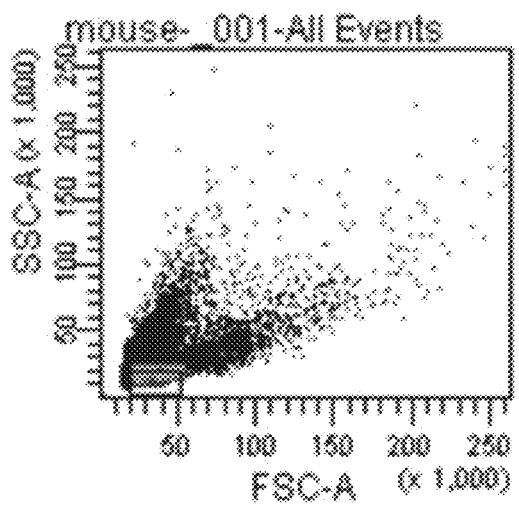
Wild-type non-transgenic
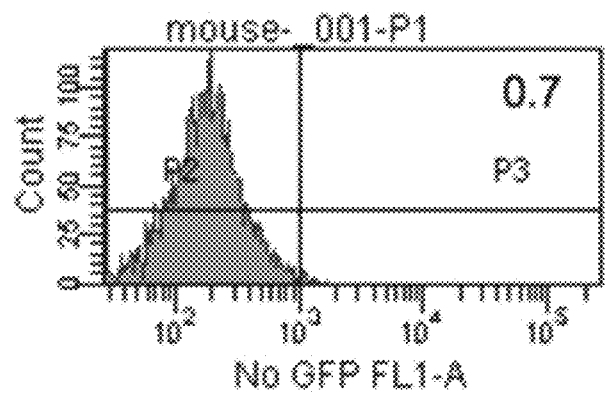
FIG. 23C

SEQUENCE LISTING

```
<160> NUMBER OF SEQ ID NOS: 19

<210> SEQ ID NO 1
<211> LENGTH: 1616
<212> TYPE: DNA
<213> ORGANISM: Homo sapiens

<400> SEQUENCE: 1
gccaaggctg gggcagggga gtcagcagag gcctcgctcg ggcgcccagt ggtcctgccg      60
cctggtctca cctcgctatg gttcgtctgc ctctgcagtg cgtcctctgg ggctgcttgc     120
tgaccgctgt ccatccagaa ccacccactg catgcagaga aaaacagtac ctaataaaca     180
gtcagtgctg ttctttgtgc cagccaggac agaaactggt gagtgactgc acagagttca     240
ctgaaacgga atgccttcct tgcggtgaaa gcgaattcct agacacctgg aacagagaga     300
cacactgcca ccagcacaaa tactgcgacc ccaacctagg gcttcgggtc cagcagaagg     360
gcacctcaga aacagacacc atctgcacct gtgaagaagg ctggcactgt acgagtgagg     420
cctgtgagag ctgtgtcctg caccgctcat gctcgcccgg ctttggggtc aagcagattg     480 ctacagggt ttctgatacc atctgcgagc cctgcccagt cggcttcttc tccaatgtgt     540
catctgcttt cgaaaaatgt caccccttgga caagctgtga gaccaaagac ctggttgtgc     600
aacaggcagg cacaaacaag actgatgttg tctgtggtcc ccaggatcgg ctgagagccc     660
tggtggtgat ccccatcatc ttcgggatcc tgtttgccat cctcttggtg ctggtcttta     720
tcaaaaaggt ggccaagaag ccaaccaata aggcccccca ccccaagcag gaaccccagg     780
agatcaattt tcccgacgat cttcctggct ccaacactgc tgctccagtg caggagactt     840
```

| | | |
|---|---|---|
| tacatggatg ccaaccggtc acccaggagg atggcaaaga gagtcgcatc tcagtgcagg | 900 | |
| agagacagtg aggctgcacc cacccaggag tgtggccacg tgggcaaaca ggcagttggc | 960 | |
| cagagagcct ggtgctgctg ctgctgtggc gtgagggtga ggggctggca ctgactgggc | 1020 | |
| atagctcccc gcttctgcct gcaccccctgc agtttgagac aggagacctg gcactggatg | 1080 | |
| cagaaacagt tcaccttgaa gaacctctca cttcaccctg gagcccatcc agtctcccaa | 1140 | |
| cttgtattaa agacagaggc agaagtttgg tggtggtggt gttggggtat ggtttagtaa | 1200 | |
| tatccaccag accttccgat ccagcagttt ggtgcccaga gaggcatcat ggtggcttcc | 1260 | |
| ctgcgcccag gaagccatat acacagatgc ccattgcagc attgtttgtg atagtgaaca | 1320 | |
| actggaagct gcttaactgt ccatcagcag gagactggct aaataaaatt agaatatatt | 1380 | |
| tatacaacag aatctcaaaa acactgttga gtaaggaaaa aaaggcatgc tgctgaatga | 1440 | |
| tgggtatgga acttttttaaa aaagtacatg cttttatgta tgtatattgc ctatggatat | 1500 | |
| atgtataaat acaatatgca tcatatatt atataacaag ggttctggaa gggtacacag | 1560 | |
| aaaacccaca gctcgaagag tggtgacgtc tggggtgggg aagaagggtc tggggg | 1616 | |

<210> SEQ ID NO 2
<211> LENGTH: 2757
<212> TYPE: DNA
<213> ORGANISM: Homo sapiens

<400> SEQUENCE: 2

| | | |
|---|---|---|
| gacaagtact gagtgaactc aaaccctctg taaagtaaca gaagttagaa ggggaaatgt | 60 | |
| cgcctctctg aagattaccc aaagaaaaag tgatttgtca ttgctttata gactgtaaga | 120 | |
| agagaacatc tcagaagtgg agtcttaccc tgaaatcaaa ggatttaaag aaaaagtgga | 180 | |
| atttttcttc agcaagctgt gaaactaaat ccacaacctt tggagaccca ggaacaccct | 240 | |
| ccaatctctg tgtgttttgt aaacatcact ggagggtctt ctacgtgagc aattggattg | 300 | |
| tcatcagccc tgcctgtttt gcacctggga agtgccctgg tcttacttgg gtccaaattg | 360 | |
| ttggctttca cttttgaccc taagcatctg aagccatggg ccacacacgg aggcagggaa | 420 | |
| catcaccatc caagtgtcca tacctcaatt tctttcagct cttggtgctg gctggtcttt | 480 | |
| ctcacttctg ttcaggtgtt atccacgtga ccaaggaagt gaaagaagtg caacgctgt | 540 | |
| cctgtggtca caatgtttct gttgaagagc tggcacaaac tcgcatctac tggcaaaagg | 600 | |
| agaagaaaat ggtgctgact atgatgtctg gggacatgaa tatatggccc gagtacaaga | 660 | |
| accggaccat cttttgatatc actaataacc tctccattgt gatcctggct ctgcgcccat | 720 | |
| ctgacgaggg cacatacgag tgtgttgttc tgaagtatga aaaagacgct ttcaagcggg | 780 | |
| aacacctggc tgaagtgacg ttatcagtca agctgactt ccctacacct agtatatctg | 840 | |
| actttgaaat tccaacttct aatattagaa ggataaatttg ctcaacctct ggaggttttc | 900 | |
| cagagcctca cctctcctgg ttggaaaatg gagaagaatt aaatgccatc aacacaacag | 960 | |
| tttcccaaga tcctgaaact gagctctatg ctgttagcag caaactggat ttcaatatga | 1020 | |
| caaccaacca cagcttcatg tgtctcatca gtatggaca tttaagagtg aatcagacct | 1080 | |
| tcaactggaa tacaaccaag caagagcatt ttcctgataa cctgctccca tcctgggcca | 1140 | |
| ttaccttaat ctcagtaaat ggaattttgt tgatatgctg cctgacctac tgctttgccc | 1200 | |
| caagatgcag agagaaagg aggaatgaga gattgagaag ggaaagtgta cgccctgtat | 1260 | |
| aacagtgtcc gcagaagcaa ggggctgaaa agatctgaag gtcccacctc catttgcaat | 1320 | |
| tgacctcttc tggaaacttc ctcagatgga caagattacc ccaccttgcc ctttacgtat | 1380 | |

```
ctgctcttag gtgcttcttc acttcagttg ctttgcagga agtgtctaga ggaatatggt      1440
gggcacagaa gtagctctgg tgaccttgat caaggtgttt tgaaatgcag aattcttgag      1500
ttctggaagg gactttagag aataccagtg ttattaatga caaaggcact gaggcccagg      1560
gaggtgaccc gaattataaa ggccagcgcc agaacccaga tttcctaact ctggtgctct      1620 ttcccttttat cagtttgact gtggcctgtt aactggtata tacatatata tgtcaggcaa     1680
agtgctgctg gaagtagaat tgtccaata caggtcaac ttcagagact atctgatttc        1740
ctaatgtcag agtagaagat tttatgctgc tgtttacaaa agcccaatgt aatgcatagg      1800
aagtatggca tgaacatctt taggagacta atggaaatat tattggtgtt tacccagtat      1860
tccatttttt tcattgtgtt ctctattgct gctctctcac tcccccatga ggtacagcag      1920
aaaggagaac tatccaaaac taatttcctc tgacatgtaa gacgaatgat ttaggtacgt      1980
caaagcagta gtcaaggagg aaagggatag tccaaagact taactggttc atattggact      2040
gataatctct ttaaatggct ttatgctagt ttgacctcat ttgtaaaata tttatgagaa      2100
agttctcatt taaaatgaga tcgttgttta cagtgtatgt actaagcagt aagctatctt      2160
caaatgtcta aggtagtaac tttccatagg gcctccttag atccctaaga tggctttttc      2220
tccttggtat ttctgggtct ttctgacatc agcagagaac tggaaagaca tagccaactg      2280
ctgttcatgt tactcatgac tccttttctct aaaactgcct tccacaattc actagaccag     2340
aagtggacgc aacttaagct gggataatca cattatcatc tgaaaatctg gagttgaaca      2400
gcaaaagaag acaacatttc tcaaatgcac atctcatggc agctaagcca catggctggg      2460
atttaaagcc tttagagcca gcccatggct ttagctacct cactatgctg cttcacaaac      2520
cttgctcctg tgtaaaacta tattctcagt gtagggcaga gaggtctaac accaacataa      2580
ggtactagca gtgtttcccg tattgacagg aatacttaac tcaataattc ttttcttttc      2640
catttagtaa cagttgtgat gactatgttt ctattctaag taattcctgt attctacagc      2700
agatactttg tcagcaatac taagggaaga acaaagttg aaccgtttct ttaataa        2757
```

<210> SEQ ID NO 3
<211> LENGTH: 2399
<212> TYPE: DNA
<213> ORGANISM: Homo sapiens
<400> SEQUENCE: 3

```
agtcattgcc gaggaaggct tgcacagggt gaaagctttg cttctctgct gctgtaacag       60
ggactagcac agacacacgg atgagtgggg tcatttccag atattaggtc acagcagaag      120
cagccaaaat ggatccccag tgcactatgg gactgagtaa cattctcttt gtgatggcct      180
tcctgctctc tgctaacttc agtcaacctg aaatagtacc aatttctaat ataacagaaa      240
atgtgtacat aaatttgacc tgctcatcta tacacggtta cccagaacct aagaagatga      300
gtgttttgct aagaaccaag aattcaacta tcgagtatga tggtattatg cagaaatctc      360
aagataatgt cacagaactg tacgacgttt ccatcagctt gtctgtttca ttccctgatg      420
ttacgagcaa tatgaccatc ttctgtattc tggaaactga caagacgcgg cttttatctt      480 caccttttctc tatagagctt gaggaccctc agcctccccc agaccacatt ccttggatta      540
cagctgtact tccaacagtt attatatgtg tgatggtttt ctgtctaatt ctatggaaat      600
ggaagaagaa gaagcggcct cgcaactctt ataaatgtgg aaccaacaca atggagaggg      660
aagagagtga acagaccaag aaaagagaaa aatccatat acctgaaaga tctgatgaag      720
cccagcgtgt ttttaaaagt tcgaagacat cttcatgcga caaaagtgat acatgttttt      780
```

```
aattaaagag taaagcccat acaagtattc attttttcta ccctttcctt tgtaagttcc    840
tgggcaacct ttttgatttc ttccagaagg caaaaagaca ttaccatgag taataagggg    900
gctccaggac tccctctaag tggaatagcc tccctgtaac tccagctctg ctccgtatgc    960
caagaggaga ctttaattct cttactgctt cttttcactt cagagcacac ttatgggcca   1020
agcccagctt aatggctcat gacctggaaa taaaatttag gaccaatacc tcctccagat   1080
cagattcttc tcttaatttc atagattgtg ttttttttt aaatagacct ctcaatttct    1140
ggaaaactgc cttttatctg cccagaattc taagctggtg ccccactgaa ttttgtgtac   1200
ctgtgactaa acaactacct cctcagtctg ggtgggactt atgtatttat gaccttatag   1260
tgttaatatc ttgaaacata gagatctatg tactgtaata gtgtgattac tatgctctag   1320
agaaaagtct acccctgcta aggagttctc atccctctgt cagggtcagt aaggaaaacg   1380
gtggcctagg gtacaggcaa caatgagcag accaacctaa atttgggaa attaggagag    1440 gcagagatag aacctggagc cacttctatc tgggctgttg ctaatattga ggaggcttgc   1500
cccacccaac aagccatagt ggagagaact gaataaacag gaaaatgcca gagcttgtga   1560
accctgtttc tcttgaagaa ctgactagtg agatggcctg gggaagctgt gaaagaacca   1620
aaagagatca caatactcaa aagagagaga gagaaaaaa agagagatct tgatccacag    1680
aaatacatga aatgtctggt ctgtccaccc catcaacaag tcttgaaaca agcaacagat   1740
ggatagtctg tccaaatgga cataagacag acagcagttt cctggtggt cagggagggg    1800 ttttggtgat acccaagtta ttgggatgtc atcttcctgg aagcagagct ggggagggag   1860
agccatcacc ttgataatgg gatgaatgga aggaggctta ggactttcca ctcctggctg   1920
agagaggaag agctgcaacg gaattaggaa gaccaagaca cagatcaccc ggggcttact   1980
tagcctacag atgtcctacg ggaacgtggg ctggcccagc atagggctag caaatttgag   2040
ttggatgatt gttttttgctc aaggcaacca gaggaaactt gcatacagag acagatatac   2100
tgggagaaat gactttgaaa acctggctct aaggtgggat cactaaggga tggggcagtc   2160
tctgcccaaa cataaagaga actctgggga gcctgagcca caaaaatgtt cctttatttt   2220
atgtaaaccc tcaagggtta tagactgcca tgctagacaa gcttgtccat gtaatattcc   2280 catgtttta ccctgcccct gccttgatta gactcctagc acctggctag tttctaacat     2340
gttttgtgca gcacagtttt taataaatgc ttgttacatt catttaaaaa aaaaaaaaa    2399
```

<210> SEQ ID NO 4
<211> LENGTH: 30
<212> TYPE: DNA
<213> ORGANISM: Homo sapiens
<400> SEQUENCE: 4
actgggcgcc cgagcgaggc ctctgctgac                                       30

<210> SEQ ID NO 5
<211> LENGTH: 30
<212> TYPE: DNA
<213> ORGANISM: Homo sapiens
<400> SEQUENCE: 5
ttgctcacgt agaagaccct cccagtgatg                                       30

<210> SEQ ID NO 6
<211> LENGTH: 30
<212> TYPE: DNA
<213> ORGANISM: Homo sapiens

```
<400> SEQUENCE: 6
aaggagtatt tgcgagctcc ccgtacctcc                                        30

<210> SEQ ID NO 7
<211> LENGTH: 29
<212> TYPE: DNA
<213> ORGANISM: Homo sapiens

<400> SEQUENCE: 7
ttgctcacgt agaagaccct ccagtgatg                                         29

<210> SEQ ID NO 8
<211> LENGTH: 31
<212> TYPE: DNA
<213> ORGANISM: Homo sapiens

<400> SEQUENCE: 8
cacagccgag gcaaagacac catgcagggc a                                      31

<210> SEQ ID NO 9
<211> LENGTH: 29
<212> TYPE: DNA
<213> ORGANISM: Homo sapiens

<400> SEQUENCE: 9
gggaaagcca ggaatctaga gccaatgga                                         29

<210> SEQ ID NO 10
<211> LENGTH: 30
<212> TYPE: DNA
<213> ORGANISM: Homo sapiens

<400> SEQUENCE: 10
tgggtgcttc cgtaagttct ggaacacgtc                                        30

<210> SEQ ID NO 11
<211> LENGTH: 25
<212> TYPE: DNA
<213> ORGANISM: Homo sapiens

<400> SEQUENCE: 11
agggactttc cgctggggac tttcc                                             25

<210> SEQ ID NO 12
<211> LENGTH: 25
<212> TYPE: DNA
<213> ORGANISM: Homo sapiens

<400> SEQUENCE: 12
ggaaagtccc cagcggaaag tccct                                             25

<210> SEQ ID NO 13
<211> LENGTH: 25
<212> TYPE: DNA
<213> ORGANISM: Homo sapiens

<400> SEQUENCE: 13
accagtccct agctaccagt cccta                                             25

<210> SEQ ID NO 14
<211> LENGTH: 25
<212> TYPE: DNA
<213> ORGANISM: Homo sapiens
```

```
<400> SEQUENCE: 14
tagggactgg tagctaggga ctggt                                              25

<210> SEQ ID NO 15
<211> LENGTH: 25
<212> TYPE: DNA
<213> ORGANISM: Homo sapiens

<400> SEQUENCE: 15
aggtactgtc cgcgttagac gtgcc                                              25

<210> SEQ ID NO 16
<211> LENGTH: 25
<212> TYPE: DNA
<213> ORGANISM: Homo sapiens

<400> SEQUENCE: 16
ggcacgtcta acgcggacag tacct                                              25

<210> SEQ ID NO 17
<211> LENGTH: 30
<212> TYPE: DNA
<213> ORGANISM: Homo spaiens

<400> SEQUENCE: 17
actgggcgcc cgagcgaggc ctctgctgac                                         30

<210> SEQ ID NO 18
<211> LENGTH: 30
<212> TYPE: DNA
<213> ORGANISM: Homo spaiens

<400> SEQUENCE: 18
aaggagtatt tgcgagctcc ccgtacctcc                                         30

<210> SEQ ID NO 19
<211> LENGTH: 29
<212> TYPE: DNA
<213> ORGANISM: Homo sapiens

<400> SEQUENCE: 19
ttgctcacgt agaagaccct ccagtgatg                                          29
```

MICROSPHERE-BASED DELIVERY AND EX VIVO MANIPULATION OF DENDRITIC CELLS FOR AUTOIMMUNE THERAPIES

CROSS-REFERENCE

This application is a continuation of U.S. patent application Ser. No. 15/635,007, filed on Jun. 27, 2017, which is a continuation of U.S. patent application Ser. No. 14/546,755, filed on Nov. 18, 2014, issued as U.S. Pat. No. 9,724,365, which in turn claims the benefit of U.S. Provisional Application No. 61/905,787, filed Nov. 18, 2013. The prior applications are incorporated herein by reference in their entirety.

STATEMENT AS TO FEDERALLY SPONSORED RESEARCH

This invention was made with government support under NIDDK DK063499 and NIDDK DK49835-01, both awarded by the National Institutes of Health. The government has certain rights in this invention.

BACKGROUND OF THE INVENTION

Diabetes mellitus results from the failure of cells to transport endogenous glucose across their membranes either because of an endogenous deficiency of insulin or an insulin receptor defect. Diabetes type 1 is caused by the destruction of beta cells, which results in insufficient levels of endogenous insulin. Type 1 diabetes selectively impairs and destroys insulin-producing beta-cells of the pancreas. The subsequent lack of insulin leads to increased blood glucose levels. Diabetes type 2, may initiate as a defect in either the insulin receptor itself or in the number of insulin receptors present or in the balance between insulin and glucagon signals, although it is ultimately caused due to a loss of functional β cells. Current treatment of individuals with clinical manifestation of diabetes attempts to emulate the role of the pancreatic β cells in a non-diabetic individual. Despite such intervention, there is often a gradual decline in the health of diabetics. Diabetes afflicts millions of people in the United States alone; a need remains for additional methods to treat type 1 diabetes.

SUMMARY OF THE INVENTION

This disclosure provides methods, compositions, and kits for treating a mammal with a disease. The methods, compositions, and kits are particularly useful for treating a mammal that has or is likely to have onset of diabetes.

In some aspects, provided herein, are methods for restoration of blood glucose to a pre-diabetic level in a pediatric mammal comprising: administering two or more subcutaneous injections of tolerogenic dendritic cells at one or more injection sites proximal to a pancreatic lymph node or the pancreas in a mammal, wherein said blood glucose may be restored to said pre-diabetic level for a period of at least twenty four hours. In some embodiments, said tolerogenic dendritic cells may be isolated from said mammal or from a different mammal. In some embodiments, said tolerogenic dendritic cells may be previously frozen.

BRIEF DESCRIPTION OF DRAWINGS

FIG. 9A is a timeline for the experiments with mice having new-onset diabetes.

FIGS. 9B-9C are graphs summarizing the mean blood glucose levels from new-onset diabetic mice treated with either AS-MSP or controls.

FIGS. 15A-15C is a figure summarizing preferential accumulation of fluorescence-labeled microspheres inside the pancreatic lymph nodes of a non-human primate.

FIG. 19 is a figure summarizing the location of the injection sites in a human.

FIGS. 23A-23C is flow cytometric data measuring green fluorescent protein (GFP) fluorescence of DC-Bregs after 5 days in co-culture with cDC, iDC and media.

SEQUENCE LISTING

Figure 1B:
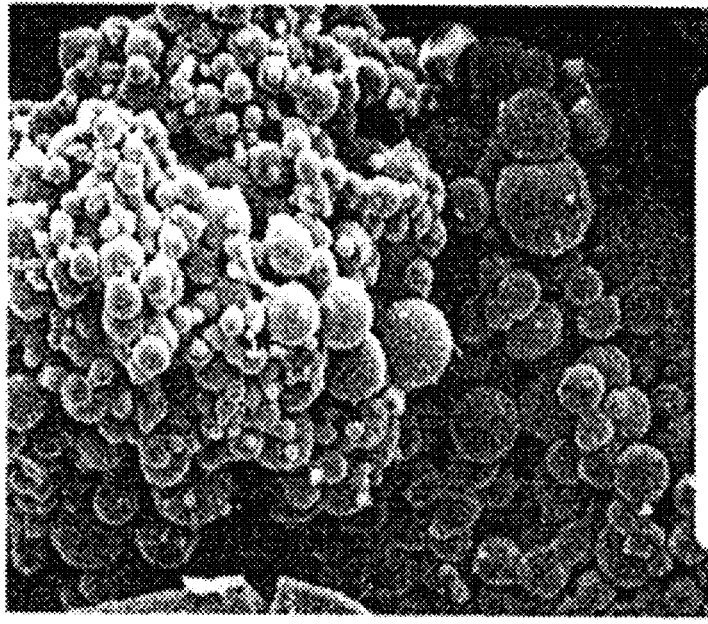
FIG. 1A and FIG. 1B are scanning electron micrographs of microspheres of AS-oligonucleotides and poly-L-lysine polycation.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand when appropriate. The Sequence Listing is provided as an ASCII text file [8123-92198-11_Sequence_Listing, Mar. 8, 2019, 11.5 KB], which is incorporated by reference herein.

DETAILED DESCRIPTION OF THE INVENTION

General Overview

U.S. Pat. Nos. 8,022,046, 7,964,574, 8,389,493, and 7,884,085 and U.S. application Ser. No. 12/822,774 are incorporated by reference. All publications and patent applications mentioned in this specification are herein incorporated by reference to the same extent as if each individual publication or patent application was specifically and individually indicated to be incorporated by reference.

This disclosure provides methods, compositions, and kits for the treatment of a condition, particularly autoimmune diseases and inflammatory diseases. Included within this disclosure are modifications of oligonucleotides, methods of making particles, methods of making tolerogenic DC populations, methods of delivery, including composition of delivery, route of delivery, frequency of delivery, methods of treating a condition, methods of evaluating the location of an in vivo delivery, and the like.

The methods of this disclosure may be useful for a variety of applications including, but not limited to, treatment of an existing condition following clinical onset, treatment of a chronic condition, or prevention of a condition. A condition may include diseases such as autoimmune disorders and inflammatory conditions, for example type I diabetes. The methods of this disclosure may also be useful for vaccine strategies, for chronic conditions, for controlled drug delivery applications, for improving bioavailability of treatment options (e.g. co-delivery of nanoparticles could be enhance delivery of oligonucleotides to endogeneous DC populations), for altering endogenous tissue responses, and other applications.

Methods of Treating

The methods, compositions, and kits of this disclosure may comprise a treatment method to prevent, arrest, reverse, or reduce a condition. In some cases, the condition may be an autoimmune disease. Autoimmune diseases may include alopecia areata, anklosing spondylitis, antiphospholipid syndrome, asthma, arthritis, autoimmune addison's disease, autoimmune deficiency syndrome (AIDS), autoimmune hemolytic anemia, autoimmune hepatitis, autoimmune inner ear disease, autoimmune lymphoproliferative syndrome (ALPS), autoimmune thrombocytopenic purpura (ATP), Behcet's disease, bullous pemphigoid, cardiomyopathy, celiac sprue-dermatitis, chronic fatigue syndrome immune deficiency syndrome (CFIDS), chronic inflammatory, demyelinating polyneuropathy, cicatricial pemphigoid, cold agglutinin disease, limited scleroderma (CREST syndrome), Crohn's disease, Dego's disease, dermatomyositis, discoid lupus, essential mixed cryoglobulinemia, fibromyalgia, fibromyositis, Grave's disease, Guillain-Barre, Hashimoto's thyroiditis, idiopathic pulmonary fibrosis, idiopathic thrombocytopenia purpura (ITP), IgA nephropathy, insulin dependent diabetes (Type I), juvenile arthritis, lung fibrosis, lupus, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis, dermatomyositis, primary agammaglobulinemia, primary biliary cirrhosis, psoriasis, Raynaud's phenomenon, Reiter's syndrome, rheumatic fever, rheumatoid arthritis, sarcoidosis, scleroderma, septic shock, Sjogren's syndrome, Stiff-Man syndrome, takayasu arteritis, temporal arteritis/Giant cell arteritis, ulcerative colitis, uveitis, vasculitis, vitiligo, Wegener's granulomatosis, and others.

The autoimmune disease may be type 1 diabetes. Type I diabetes is an autoimmune disorder where there is a progressive inflammation of the pancreas. The inflammation renders the pancreatic beta cells dysfunctional. Left untreated, type 1 diabetes results in chronic inflammation and a reduction in functional pancreatic beta cell mass.

The condition may be an inflammatory disease. Inflammatory diseases may include acne vulgaris, Alzheimer's, arthritis, asthma, atherosclerosis, cancer, celiac disease, chronic prostatitis, colitis, crown's disease, dermatitis, hepatitis, inflammatory bowel disease (IBD), interstitial cystitis, irritable bowel syndrome, multiple sclerosis, nephritis, Parkinson's, pelvic inflammatory disease, reperfusion injury, rheumatoid arthritis, sarcoidosis, systemic lupus erythematosus, type 1 diabetes, ulcerative colitis, vasculitis and others.

It may be desirable to have a treatment method that may prevent the onset of a condition (e.g. autoimmune disease, inflammatory disease). It may be desirable to have a treatment that may arrest a condition (e.g. autoimmune disease, inflammatory disease) after clinical onset. It may be desirable to have a treatment that may reverse a condition (e.g. autoimmune disease, inflammatory disease) after clinical onset. It may be desirable to have a treatment that may reduce the condition (e.g. autoimmune disease, inflammatory disease) after clinical onset. A treatment method that may prevent, arrest, reverse, or reduce a condition (e.g. type 1 diabetes) may include preserving viability of remaining beta cell populations, restoring or expanding remaining beta cell populations, reducing inflammation, reducing blood glucose levels to pre-diabetic levels, increasing suppressive B-cell populations, reducing T-cell populations, inducing retinoic acid (RA) production in dendritic cell (DC) populations, increasing tolerogenic DC populations, or combinations thereof. A treatment that may prevent, arrest, reverse, or reduce a condition (e.g. inflammatory bowel disease) may include reducing inflammation, increasing suppressive B-cell populations, reducing T-cell populations, inducing RA production in DC populations, increasing tolerogenic DC populations, or combinations thereof.

The treatment method may comprise treating a subject (e.g. a patient with a condition and/or a lab animal with a condition). The condition may be an autoimmune disease. The condition may be an inflammatory disease. The subject may be a mammal. The mammal may be a mouse, including NOD mice, NOD/LU mice, NOD-scid mice, C3H/HeJ (H2$^k$) mice, C57BL6 mice, Balb/c mice, diabetes-free mice, new-onset diabetic mice, and others. The mammal may be a non-human primate including *Maccaca fascicularis* monkeys, rhesus monkeys, and others. The mammal may be a human. The human may be an infant, a child, an adolescent, an adult, and others.

The subject may be a pediatric mammal. The subject may be a neonatal mammal. The subject may be a geriatric mammal. The subject may be a pediatric mammal at risk of developing a condition (e.g. type 1 diabetes). The subject may be a pediatric mammal with a condition (e.g. type 1 diabetes). The treatment method may be preferred for a pediatric mammal.

In some instances, composition of injections, timing of injections, amount of injections, anatomical location of injections may be altered to accommodate a pediatric mammal. In some instances, composition of injections, timing of injections, amount of injections, anatomical location of injections may be altered to accommodate physically smaller or physically larger patients.

A pediatric mammal may be a human. A pediatric mammal may be a mouse or non-human primate. A pediatric mammal may be a human that is less than 18 years of age. A pediatric mammal may be 1, 2, 3, 4, 5, 6, 7, 8, 9, 10, 11, 12, 13, 14, 15, 16, 17, 18 years old. A pediatric mammal may be an infant, such as a child of less than about 1 year of age. A pediatric mammal may be a young child, such as between about 1 year and about 2 years of age, between about 1 year and about 3 years of age, or between about 1 year and about 5 years of age. A pediatric mammal may be a child, such as between about 6 years and 10 years of age, between about 6 years of age and about 12 years of age. A pediatric mammal may be between about 11 years and 13 years of age. A pediatric mammal may be between about 11 years and 18 years of age. A pediatric mammal may be an adolescent, such as between about 13 years and 18 years of year.

Treatment may be provided to the subject before clinical onset of the condition (e.g. type 1 diabetes). Treatment may be provided for about: 1 day, 1 week, 1 month, 2 months, 3 months, 4 months, 5 months, 6 months, 7 months, 8 months, 9 months, 10 months, 11 months, 1 year, 1.5 years, 2 years, 3 years, 4 years, 5 years, 10 years, 15 years before onset of the condition. Treatment may be provided for more than about: 1 day, 1 week, 1 month, 2 months, 3 months, 4 months, 5 months, 6 months, 7 months, 8 months, 9 months, 10 months, 11 months, 1 year, 1.5 years, 2 years, 3 years, 4 years, 5 years, 10 years, 15 years, before clinical onset of the condition. Treatment may be provided for less than about: 1 day, 1 week, 1 month, 2 months, 3 months, 4 months, 5 months, 6 months, 7 months, 8 months, 9 months, 10 months, 11 months, 1 year, 1.5 years, 2 years, 3 years, 4 years, 5 years, 10 years, 15 years, before clinical onset of the condition.

Treatment may be provided to the subject after clinical onset of the condition (e.g. type 1 diabetes). Clinical onset of type 1 diabetes may be the need for a subject to utilize insulin injections to regulate blood sugar levels. In pediatric patients, a blood sugar level below 70 mg/dl can be considered low and, in some instances, can be characterized by symptoms such as, e.g. sweating, hunger and/or shakiness. In pediatric patients, a blood sugar level above 200 mg/dl can be considered high and can be characterized, in some instances, by low energy, stomachaches, and/or difficulty breathing. In pediatric patients, about 70 to about 120 mg/dl blood sugar level is considered normal. In pediatric patients, about 120 to about 200 mg/dl blood sugar level is considered outside the normal range, but it can be within the goal or target range for pediatric patients trying to maintain blood sugar levels. For pediatric patients aged about 12 years and older, maintaining a blood sugar level from about 70 to about 150 mg/dl can be a goal (e.g. for pediatric patients with diabetes). For pediatric patients aged about five years of age to about eleven years of age, maintaining a blood sugar level from about 70 to about 180 mg/dl can be a goal (e.g. for pediatric patients with diabetes). For pediatric patients aged about five years of age or younger, maintaining a blood sugar level from about 80 to about 200 mg/dl can be a goal (e.g. for pediatric patients with diabetes). One skilled in the art will recognize that these ranges are standard guidelines and, e.g., individual target ranges may vary based on a patient's age, body size, development, and the like.

Clinical onset of type 1 diabetes may be hyperglycemia. Clinical onset of type 1 diabetes may be the inability for a subject to regulate blood glucose levels. Clinical onset of type 1 diabetes may be inflammation of the pancreas. Clinical onset of type 1 diabetes may be pancreatic beta cell autoimmunity. Clinical onset of type 1 diabetes may be partial destruction of pancreatic beta cell mass. Destruction of pancreatic beta cell mass may be inflamed tissue, expansion of fibrotic legions, cellular apoptosis, cellular necrosis, cellular loss of function (e.g. inability to produce insulin, reduced insulin production). Clinical onset of type 1 diabetes may be about: 99%, 95%, 90%, 85%, 80%, 75%, 70%, 65%, 60%, 55%, 50%, 45%, 40%, 35%, 30%, 25%, 20%, 15%, 10%, or 5% destruction of pancreatic beta cell mass. Clinical onset of type 1 diabetes may be more than about: 99%, 95%, 90%, 85%, 80%, 75%, 70%, 65%, 60%, 55%, 50%, 45%, 40%, 35%, 30%, 25%, 20%, 15%, 10%, 5% destruction of pancreatic beta cell mass. Clinical onset of type 1 diabetes may be less than about: 99%, 95%, 90%, 85%, 80%, 75%, 70%, 65%, 60%, 55%, 50%, 45%, 40%, 35%, 30%, 25%, 20%, 15%, 10%, 5% destruction of pancreatic beta cell mass. Clinical onset of type 1 diabetes may be complete destruction of pancreatic beta cell mass. Clinical onset of type 1 diabetes may include the onset of one or more symptoms of type 1 diabetes such as blurred vision, nausea, hyperglycemia, fatigue, weakness, muscle cramps, peripheral neuropathy, retinopathy, nephropathy, ulcers, other symptoms, and combinations thereof.

Treatment after clinical onset may be about: 1 hour, 6 hours, 12 hours, 1 day, 2 days, 3 days, 4 days, 5 days, 6 days, 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, or 20 years after clinical onset. Treatment after clinical onset may be more than about: 1 hour, 6 hours, 12 hours, 1 day, 2 days, 3 days, 4 days, 5 days, 6 days, 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 20 years after clinical onset. Treatment after clinical onset may be less than about: 1 hour, 6 hours, 12 hours, 1 day, 2 days, 3 days, 4 days, 5 days, 6 days, 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 20 years after clinical onset. In some instances, treatment may be provided within 5 years of clinical onset. In some instances, treatment may be provided before about 5 years of clinical onset. In some instances, treatment may begin within about 5 years of clinical onset. In some instances, treatment may begin within about 4 years of clinical onset. In some instances, treatment may begin within about 3 years of clinical onset. In some instances, treatment may begin within about 2 years of clinical onset. Treatment may be provided to the subject after two, three, four, or more consecutive measurements of nonfasting blood glucose level greater than a given concentration (e.g. 250 mg/dl, 300 mg/dl). Treatment may also include treating a mammal in a clinical trial.

An "effective amount" of treatment may comprise various compositions as described throughout the disclosure including in vivo delivery of cells (e.g. ex vivo manipulated DCs), in vivo delivery of particles (e.g. microspheres or nanospheres comprising antisense oligonucleotides), in vivo delivery of substances (e.g. chemicals such as buffer salts; drug compounds such as small molecules; proteins such as growth factors, cytokines, chemokines; hormones, peptides, DNA, RNA, and others), recruitment of endogenous cell populations or combinations thereof. An "effective amount" of treatment may comprise in vivo delivery of cells, in vivo delivery of particles, in vivo delivery of substances, recruitment of endogenous cell populations or combinations thereof at specific anatomical locations, one or more repeated dosages, of specific amounts or specific concentrations as described throughout the disclosure. An "effective amount" of treatment may prevent, arrest, reverse, or reduce a condition (e.g. type 1 diabetes), may include preserving viability of remaining beta cell populations, reducing inflammation, reducing blood glucose levels to pre-diabetic levels, increasing suppressive B-cell populations, reducing T-cell populations, inducing retinoic acid (RA) production in dendritic cell (DC) populations, increasing tolerogenic DC populations, or combinations thereof.

Cells

Cells may refer to mammalian cells, including human cells, mouse cells, and non-human primate cells. Cells may also refer to endogenous cells, primary cells or freshly isolated cells, and cell lines. In one non-limiting example, cell lines may include HEK293 cells. Cell lines may include any cell lines provided by American Tissue Culture Center (ATCC). In some cases, primary cells or freshly isolated cells may be isolated from various tissues. Primary cells may be isolated from bone marrow, lymph node, skin, pancreas, peripheral blood or others. Cells may be passaged cells, frozen cells, thawed cells, transfected cells, sorted cells, and labeled cells. Cells may refer to immune cells. Immune cells may be suppressive or tolerogenic. Immune cells may refer to white blood cells or leukocytes. Leukocytes may include lymphocytes, neutrophils, eosinophils, basophils, and monocytes. Leukocytes may also include antigen-presenting cells, such as dendritic cells. Lymphocytes may include T-cells and B-cells. In some cases, B-cells may be suppressive B-cells, DC-Bregs, B10 Bregs. In some cases, B-cells may express a combination of markers, for example, B220+ CD11c−; CD1 $d^{HIGH}$, CD5+, IL-10+; B220+, CD19+, CD1 d+, CD5+, IL-10+; B220+, CD19+, CD1 d+, CD5, CD11c−, IL-10+; CD19+, CD24$^{HIGH}$, CD27+, CD38$^{HIGH}$; CD19+, CD24$^{HIGH}$, CD27+, CD38$^{HIGH}$, IL-10+; B220+, CD19+, IL-10+; B220+, CD19+, CD11c−, IL-10+; B220+, CD19+, CD11c−; B220+, CD19+, CD11c−, IgD$^{HIGH}$, IgM+, CD10$^{LOW}$, CD21+, CD27+, CD38+, CD40$^{HIGH}$, IL-10+; CD19+, CD27+, CD38+, CD40+; and others. In some cases, dendritic cells may be tolerogenic dendritic cells (iDCs) or control dendritic cells (cDCs). In some cases, DCs may express a combination of markers, for example, CD11c+, CD45+; CD83+ HLA-DR+CD11c+; MHCII+, CD11c+, CD80+, CD40+, CD86+; CD1B+, CD5+, CD19+, IL10+; CD19+, CD27+, CD38, CD24+; or others. Memory populations may additionally express CD27+. Positive expression levels of cell markers may vary between experimental samples, vary between cell populations, vary between subjects from which they are isolated, vary within a subpopulation, or combinations thereof. In some cases, positive expression levels of one or more markers may be high, such as CD1 d, CD24, CD38, IgD, or CD40. In some cases, positive expression levels of one or more markers may be medium, such as CD1 d, CD24, CD38, IgD, or CD40. In some cases, positive expression levels of one or more markers may be low, such as CD1 d, CD24, CD38, IgD, or CD40. In some cases, positive expression levels of one or more markers may be low, such as CD10. Expression of a marker may be determined by any methods know to those of skill in the art. In some non-limiting examples, expression can be determined by fluorescence activate cells sorting using standard method for gating for high and low expressing cells.

In some embodiments, the tolerogenic dendritic cells have at least one of the following properties i) capable of converting naive T-cells to Foxp3+ T regulatory cells ex vivo and/or in vivo (e.g., inducing expression of FoxP3 in the naive T-cells); blocking the conversion of naive T-cells to TH17 T-cells; iii) capable of deleting effector T-cells ex vivo and/or in vivo; iv) retain their tolerogenic phenotype upon stimulation with at least one TLR agonist ex vivo (and, in some embodiments, increase expression of costimulatory molecules in response to such stimulus); and/or v) do not transiently increase their oxygen consumption rate upon stimulation with at least one TLR agonist ex vivo; and/or vi) capable of converting B-cells to regulatory B-cells ex vivo and/or in vivo. In some embodiments, the iDCs have at least 2, at least 3, 4, or all 5 of the above properties. Tolerogenic DCs are generally derived from mammalian DCs. Tolerogenic DCs may be obtained from donor mammals. A donor mammal may be the same subject mammal receiving the administration (i.e. autologous). A donor mammal may be a mammal different from the one receiving the administration, but of the same species (i.e. allogeneic). A donor mammal may be a mammal different from the one receiving the administration and also from a different species (i.e. xenogeneic). A therapeutically effective amount of tolerogenic DCs can be administered to a subject for prevention and/or treatment, such as of type I diabetes. In some embodiments, DCs are isolated from a donor, and transplanted into a recipient. The donor and the recipient can be the same subject, and thus the cells can be autologous. The donor and the recipient can be from different subjects, and thus the cells can be allogeneic. In some embodiments, tissues from which DCs may be isolated to produce the tolerogenic DCs include, but are not limited to, liver, spleen, bone marrow, peripheral blood, thymus or lymph nodes. In one embodiment, the source of the DCs is bone marrow.

Tolerogenic DCs may be mixed with known cells. Known cells can be cells than can promote ex vivo tolerogenic DC survival and growth, such as cells from a feeder layer. Known cells can be cells than can promote in vivo tolerogenic DC survival and growth, such as stromal cells. A known cell can be a cell that is a positive or negative control population, such as a non-tolerogenic DC. A positive or negative control cell can be a cell from a known origin, such as the spleen or bone marrow. The control cell may contain a functional moiety. The functional moiety can be a marker. The marker can be an antigen that can be recognized. The moiety can be a fluorescent protein.

Cells may contain one or more markers. The marker can be an antigen, a fluorescent protein, a fluorescent quantum dot, a radio-active isotope, and others. The marker can be used to indicate cell viability. The marker can be used to distinguish distinct cell populations based on surface marker combinations, cell size, and other characteristics. The marker can be used to sort subpopulations of cells prior to in vivo delivery. Cells may be sorted by viability. Cells may be sorted by surface marker expression. Cells may be sorted by size. The marker can be used to track cells in vivo after delivery. Imaging may be used to detect markers to determine location or viability of cells after delivery.

Non-limiting examples of sorting methods than may be used to sort cells as described herewith include, size-specific cell strainers, positive magnetic sorting columns (e.g. magnetic-activated cell sorting, MACS), negative magnetic sorting columns, size exclusion columns, microfluidic devices, laser sorting, fluorescent activated cell sorting (FACS), FACS by flow cytometry, single color FACS by flow cytometry, multi-color FACS by flow cytometry, IsoRaft array, DEPArray lab-on-a-chip, density gradient centrifugation and others.

In one non-limiting example, the present invention provides for a method of producing tolerogenic DCs comprising a) propagating immature mammalian DCs from a mammalian donor, b) incubating the DCs with one or more antisense oligonucleotides having at least one binding site for CD40, one or more antisense oligonucleotides having at least one binding site for CD80, and one or more antisense oligonucleotides having at least one binding site for CD86 under conditions wherein the DCs may internalize the one or more oligonucleotides, and c) culturing said DCs.

Ex vivo DCs may internalize all oligonucleotides. Ex vivo DCs may internalize all CD40 oligonucleotides. Ex vivo DCs may internalize all CD80 oligonucleotides. Ex vivo DCs may internalize all CD86 oligonucleotides. Ex vivo DCs may internalize a portion of oligonucleotides. Ex vivo DCs may internalize about: 99%, 98%, 97%, 96%, 95%, 90%, 85%, 80%, 75%, 70%, 65%, 60%, 55%, 50%, 45%, 40%, 35%, 30%, 25%, 20%, 15%, or 10% of oligonucleotides. Ex vivo DCs may internalize more than about: 99%, 98%, 97%, 96%, 95%, 90%, 85%, 80%, 75%, 70%, 65%, 60%, 55%, 50%, 45%, 40%, 35%, 30%, 25%, 20%, 15%, 10% of oligonucleotides. Ex vivo DCs may internalize less than about: 99%, 98%, 97%, 96%, 95%, 90%, 85%, 80%, 75%, 70%, 65%, 60%, 55%, 50%, 45%, 40%, 35%, 30%, 25%, 20%, 15%, 10% of oligonucleotides. Non-internalized oligonucleotides may be removed prior to in vivo delivery. Non-internalized oligonucleotides may not be removed prior to in vivo delivery. One or more oligonucleotides may attach to the surface of one or more cells. Oligonucleotides may be internalized by cells other than ex vivo DCs.

In one non-limiting example, the one or more oligonucleotides may have the nucleotide sequence set forth as SEQ ID NO: 4. In one non limiting example, the one or more oligonucleotides may comprise or consist of the nucleotide sequence set forth as SEQ ID NO: 5. In one non limiting example, the one or more oligonucleotides may comprise or consist of the nucleotide sequence set forth as SEQ ID NO: 6. In one non limiting example, the one or more oligonucleotides may comprise or consist of the nucleotide sequence set forth as SEQ ID NO: 7. In one non limiting example, the one or more oligonucleotides may comprise a combination of nucleotide sequences set forth as SEQ ID NOs: 4, 5, 6, and 7. The method may further comprise incubating the DCs in the presence of one or more substances such as small molecules, hormones, chemokines, growth factors, cytokines, including GM-CSF, TGF-β, IL-4, or combinations thereof. Incubation of one or more substances such as cytokines with DCs may occur prior to or contemporaneously with the incubation with the one or more oligonucleotides containing at least one binding site for CD40, at least one binding site for CD80, and at least one binding site for CD86. Expression of a marker, such as CD40, CD80, or CD86 in a cell, such as a DC, may be inhibited when one or more binding sites is bound by an inhibitory RNA. Any of the oligonucleotides described below can be used in the disclosed methods.

The propagating, the incubating, and the culturing steps may take place in a culture device. The culture device may be an open system. The culture device may be a closed system. The culture device may be an automated system. The culture device may not be an automated system. The culture device may be kept in sterile conditions. The culture device may be in a clinical setting. Automated culture systems may include for example, TAP Biosystem's Select, Cello, Piccolo, and Cellmate systems, Hamilton's Cell Host, TerumoBCT's Quantum Cell Expansion, Logos Biosystem's CELF, Aastrom Bioscience's Replicell System, and others. Non-automated culture systems may include tissue culture plates, treated petri dishes, and others.

The one or more oligonucleotides may be added to the DC cultures at a concentration of about 0.001 µM to about 20 µM, such as about 1 to about 15 µM, such as about 1 µM to about 5 µM, such as about 3 µM to about 4 µM, such as about: 0.001 µM, 0.01 µM, 0.1 µM, 0.5 µM, 1.0 µM, 1.5 µM, 2.0 µM, 2.5 µM, 3.0 µM, 3.1 µM, 3.2 µM, 3.3 µM, 3.4 µM, 3.5 µM, 4.0 µM, 4.5 µM, 5.0 µM, 6.0 µM, 7.0 µM, 8.0 µM, 9.0 µM, 10 µM, 15 µM, or 20 µM. The one or more oligonucleotides may be added to the DC cultures at a concentration of more than about: 0.001 µM, 0.01 µM, 0.1 µM, 0.5 µM, 1.0 µM, 1.5 µM, 2.0 µM, 2.5 µM, 3.0 µM, 3.1 µM, 3.2 µM, 3.3 µM, 3.4 µM, 3.5 µM, 4.0 µM, 4.5 µM, 5.0 µM, 6.0 µM, 7.0 µM, 8.0 µM, 9.0 µM, 10 µM, 15 µM, or 20 µM. The one or more oligonucleotides may be added to the DC cultures at a concentration of less than about: 0.001 µM, 0.01 µM, 0.1 µM, 0.5 µM, 1.0 µM, 1.5 µM, 2.0 µM, 2.5 µM, 3.0 µM, 3.1 µM, 3.2 µM, 3.3 µM, 3.4 µM, 3.5 µM, 4.0 µM, 4.5 µM, 5.0 µM, 6.0 µM, 7.0 µM, 8.0 µM, 9.0 µM, 10 µM, 15 µM, or 20 µM. The one or more oligonucleotides may be added to the DC cultures at the same concentration. The one or more oligonucleotides may be added to the DC cultures at different concentrations for each oligonucleotide.

DCs can be isolated from tissues. Some non-limiting examples of tissue from which to isolate DCs can include: liver, spleen, bone marrow, peripheral blood, thymus, lymph nodes, pancreas, and others tissues or any combination thereof. The tissues may be collected via syringe, for example, peripheral blood. The tissues may be collected via tissue biopsy, for example, bone marrow. The tissue may be collected via complete organ resection, for example, pancreas.

Isolating DCs may be accomplished by any technique known to the skilled artisan. For example, DCs may be generated from precursors. DCs may be isolated from a subject or a donor in accordance with the method described in the examples section. Once generated, DCs may be propagated by any suitable cell culturing technique known to the skilled artisan. For example, the DCs may be propagated in accordance with the method in the examples section herein.

A method for enhancing tolerogenicity in a host can comprise: a) propagating immature DCs from an isolated tissue, b) incubating the DCs with one or more antisense oligonucleotides having at least one binding site for CD40, one or more antisense oligonucleotides having at least one binding site for CD80, and one or more antisense oligonucleotides having at least one binding site for CD86 under conditions wherein the DCs internalize the one or more oligonucleotides, c) culturing the oligonucleotide-comprising DCs, and d) administering the oligonucleotide-comprising DCs to the mammalian host in an effective amount. The one or more oligonucleotides can comprise of consist of the nucleotide sequence set forth by SEQ ID NO: 4. The one or more oligonucleotides can comprise of consist of the nucleotide sequence set forth by SEQ ID NO: 5. The one or more oligonucleotides can comprise of consist of the nucleotide sequence set forth by SEQ ID NO: 6. The one or more oligonucleotides can comprise of consist of the nucleotide sequence set forth by SEQ ID NO: 7. The method may further comprise incubating the DCs in the presence of one or more small molecules, hormones, proteins, peptides, chemokines, growth factors, cytokines, such as GM-CSF, TGF-β, IL-4, or combinations thereof prior to or contemporaneously with the incubation with the one or more antisense oligonucleotides containing at least one binding site for CD40, at least one binding site for CD80, and at least one binding site for CD86.

Enhancing tolerogenicity in a host may comprise delivery of one or more entities (e.g. antisense oligonucleotides, retinoic acid (RA), transforming growth factor beta (TGF-β)) to an ex vivo DCs population, a population which may be subsequently injected into the subject in an effective amount. The one or more entities can be modified to enhance receptor-mediated internalization of said entities in ex vivo DC populations. The one or more entities can be coated onto, attached to, embedded within, suffused throughout, covalently linked, or physically encapsulated within particles and delivered to ex vivo DC populations. Particles can be liposomes, microspheres, nanospheres, or the like. In some embodiments, particles and DC populations containing internalized entities are co-injected into a subject in an effective amount. Particles and DC populations containing internalized particles can be co-injected into a subject in an effective amount. Particles and tolerogenic DC populations can be co-injected into a subject in an effective amount. Particles and immature DC populations can be co-injected into a subject in an effective amount. Particles and ex vivo manipulated DC populations can be co-injected into a subject in an effective amount.

The term "about," as used herein and throughout the disclosure, generally refers to a range that may be 15% greater than or 15% less than the stated numerical value within the context of the particular usage, unless otherwise specified. For example, "about 10" would include a range from 8.5 to 11.5.

Oligonucleotides

The methods, compositions, and kits of this disclosure may comprise entities, such as oligonucleotides that are antisense to and targeted to bind to primary transcripts selected from the group consisting of CD40, CD80, and CD86 primary transcripts and combinations thereof, or indeed any other oligonucleotides that target CD40, CD80, and CD86. Any type of antisense compound that specifically binds to ribonucleic acid (RNA) that encodes CD40, CD80 and CD86 is contemplated for use. In some examples, the agent is an antisense compound selected from an antisense oligonucleotide, a small inhibitory (si)RNA, a short hairpin RNA (shRNA), or a ribozyme specific for an RNA that encodes CD40, CD80, or CD86 or combinations thereof.

Antisense compounds can be prepared by designing compounds that are complementary to, and specifically bind, the target nucleotide sequence. Antisense compounds need not be 100% complementary to the target nucleic acid molecule to specifically bind with the target nucleic acid molecule. For example, the antisense compound, or antisense strand of the compound if a double-stranded compound, can be at least 70%, at least 75%, at least 80%, at least 85%, at least 90%, at least 91%, at least 92%, at least 93%, at least 94%, at least 95%, at least 96%, at least 97%, at least 98%, at least 99% or 100% complementary to the selected target nucleic acid sequence. The antisense compound, or antisense strand of the compound can be slightly longer than the selected target nucleic acid sequence, for example, about: 1, 2, 3, 4, 5, 6, 7, 8, 9, 10, 15, 20, 25, 30 base pairs (bps) longer. The antisense compound, or antisense strand of the compound can be slightly shorter than the selected target nucleic acid sequence, for example, about: 1, 2, 3, 4, 5, 6, 7, 8, 9, 10, 15, 20, 25, 30 base pairs (bps) shorter. Methods of screening antisense compounds for specificity are well known in the art (see, for example, U.S. Patent Application Publication No. 2003-0228689).

Exemplary nucleic acid sequences encoding human CD40, CD80 and CD86 are provided below:

```
Human CD40 (SEQ ID NO: 1):
GCCAAGGCTG GGGCAGGGGA GTCAGCAGAG GCCTCGCTCG GGCGCCCAGT GGTCCTGCCG

CCTGGTCTCA CCTCGCTATG GTTCGTCTGC CTCTGCAGTG CGTCCTCTGG GGCTGCTTGC

TGACCGCTGT CCATCCAGAA CCACCCACTG CATGCAGAGA AAAACAGTAC CTAATAAACA

GTCAGTGCTG TTCTTTGTGC CAGCCAGGAC AGAAACTGGT GAGTGACTGC ACAGAGTTCA

CTGAAACGGA ATGCCTTCCT TGCGGTGAAA GCGAATTCCT AGACACCTGG AACAGAGAGA

CACACTGCCA CCAGCACAAA TACTGCGACC CCAACCTAGG GCTTCGGGTC CAGCAGAAGG

GCACCTCAGA AACAGACACC ATCTGCACCT GTGAAGAAGG CTGGCACTGT ACGAGTGAGG

CCTGTGAGAG CTGTGTCCTG CACCGCTCAT GCTCGCCCGG CTTTGGGGTC AAGCAGATTG

CTACAGGGGT TTCTGATACC ATCTGCGAGC CCTGCCCAGT CGGCTTCTTC TCCAATGTGT

CATCTGCTTT CGAAAAATGT CACCCTTGGA CAAGCTGTGA GACCAAAGAC CTGGTTGTGC

AACAGGCAGG CACAAACAAG ACTGATGTTG TCTGTGGTCC CCAGGATCGG CTGAGAGCCC

TGGTGGTGAT CCCCATCATC TTCGGGATCC TGTTTGCCAT CCTCTTGGTG CTGGTCTTTA

TCAAAAAGGT GGCCAAGAAG CCAACCAATA AGGCCCCCCA CCCCAAGCAG GAACCCCAGG

AGATCAATTT TCCCGACGAT CTTCCTGGCT CCAACACTGC TGCTCCAGTG CAGGAGACTT

TACATGGATG CCAACCGGTC ACCCAGGAGG ATGGCAAAGA GAGTCGCATC TCAGTGCAGG

AGAGACAGTG AGGCTGCACC CACCCAGGAG TGTGGCCACG TGGGCAAACA GGCAGTTGGC

CAGAGAGCCT GGTGCTGCTG CTGCTGTGGC GTGAGGGTGA GGGGCTGGCA CTGACTGGGC

ATAGCTCCCC GCTTCTGCCT GCACCCCTGC AGTTTGAGAC AGGAGACCTG GCACTGGATG

CAGAAACAGT TCACCTTGAA GAACCTCTCA CTTCACCCTG GAGCCCATCC AGTCTCCCAA

CTTGTATTAA AGACAGAGGC AGAAGTTTGG TGGTGGTGGT GTTGGGGTAT GGTTTAGTAA

TATCCACCAG ACCTTCCGAT CCAGCAGTTT GGTGCCCAGA GAGGCATCAT GGTGGCTTCC

CTGCGCCCAG GAAGCCATAT ACACAGATGC CCATTGCAGC ATTGTTTGTG ATAGTGAACA

ACTGGAAGCT GCTTAACTGT CCATCAGCAG GAGACTGGCT AAATAAAATT AGAATATATT

TATACAACAG AATCTCAAAA ACACTGTTGA GTAAGGAAAA AAAGGCATGC TGCTGAATGA

TGGGTATGGA ACTTTTTAAA AAAGTACATG CTTTTATGTA TGTATATTGC CTATGGATAT

ATGTATAAAT ACAATATGCA TCATATATTG ATATAACAAG GGTTCTGGAA GGGTACACAG

AAAACCCACA GCTCGAAGAG TGGTGACGTC TGGGGTGGGG AAGAAGGGTC TGGGGG

CD80 (SEQ ID NO: 2):
GACAAGTACT GAGTGAACTC AAACCCTCTG TAAAGTAACA GAAGTTAGAA GGGGAAATGT

CGCCTCTCTG AAGATTACCC AAAGAAAAAG TGATTTGTCA TTGCTTTATA GACTGTAAGA

AGAGAACATC TCAGAAGTGG AGTCTTACCC TGAAATCAAA GGATTTAAAG AAAAAGTGGA

ATTTTTCTTC AGCAAGCTGT GAAACTAAAT CCACAACCTT TGGAGACCCA GGAACACCCT

CCAATCTCTG TGTGTTTTGT AAACATCACT GGAGGGTCTT CTACGTGAGC AATTGGATTG

TCATCAGCCC TGCCTGTTTT GCACCTGGGA AGTGCCCTGG TCTTACTTGG GTCCAAATTG

TTGGCTTTCA CTTTTGACCC TAAGCATCTG AAGCCATGGG CCACACACGG AGGCAGGGAA
```

-continued

```
CATCACCATC CAAGTGTCCA TACCTCAATT TCTTTCAGCT CTTGGTGCTG GCTGGTCTTT

CTCACTTCTG TTCAGGTGTT ATCCACGTGA CCAAGGAAGT GAAAGAAGTG GCAACGCTGT

CCTGTGGTCA CAATGTTTCT GTTGAAGAGC TGGCACAAAC TCGCATCTAC TGGCAAAAGG

AGAAGAAAAT GGTGCTGACT ATGATGTCTG GGGACATGAA TATATGGCCC GAGTACAAGA

ACCGGACCAT CTTTGATATC ACTAATAACC TCTCCATTGT GATCCTGGCT CTGCGCCCAT

CTGACGAGGG CACATACGAG TGTGTTGTTC TGAAGTATGA AAAAGACGCT TTCAAGCGGG

AACACCTGGC TGAAGTGACG TTATCAGTCA AAGCTGACTT CCCTACACCT AGTATATCTG

ACTTTGAAAT TCCAACTTCT AATATTAGAA GGATAATTTG CTCAACCTCT GGAGGTTTTC

CAGAGCCTCA CCTCTCCTGG TTGGAAAATG GAGAAGAATT AAATGCCATC AACACAACAG

TTTCCCAAGA TCCTGAAACT GAGCTCTATG CTGTTAGCAG CAAACTGGAT TTCAATATGA

CAACCAACCA CAGCTTCATG TGTCTCATCA AGTATGGACA TTTAAGAGTG AATCAGACCT

TCAACTGGAA TACAACCAAG CAAGAGCATT TTCCTGATAA CCTGCTCCCA TCCTGGGCCA

TTACCTTAAT CTCAGTAAAT GGAATTTTTG TGATATGCTG CCTGACCTAC TGCTTTGCCC

CAAGATGCAG AGAGAGAAGG AGGAATGAGA GATTGAGAAG GGAAAGTGTA CGCCCTGTAT

AACAGTGTCC GCAGAAGCAA GGGGCTGAAA AGATCTGAAG GTCCCACCTC CATTTGCAAT

TGACCTCTTC TGGGAACTTC CTCAGATGGA CAAGATTACC CCACCTTGCC CTTTACGTAT

CTGCTCTTAG GTGCTTCTTC ACTTCAGTTG CTTTGCAGGA AGTGTCTAGA GGAATATGGT

GGGCACAGAA GTAGCTCTGG TGACCTTGAT CAAGGTGTTT TGAAATGCAG AATTCTTGAG

TTCTGGAAGG GACTTTAGAG AATACCAGTG TTATTAATGA CAAAGGCACT GAGGCCCAGG

GAGGTGACCC GAATTATAAA GGCCAGCGCC AGAACCCAGA TTTCCTAACT CTGGTGCTCT

TTCCCTTTAT CAGTTTGACT GTGGCCTGTT AACTGGTATA TACATATATA TGTCAGGCAA

AGTGCTGCTG GAAGTAGAAT TTGTCCAATA ACAGGTCAAC TTCAGAGACT ATCTGATTTC

CTAATGTCAG AGTAGAAGAT TTTATGCTGC TGTTTACAAA AGCCCAATGT AATGCATAGG

AAGTATGGCA TGAACATCTT TAGGAGACTA ATGGAAATAT TATTGGTGTT TACCCAGTAT

TCCATTTTTT TCATTGTGTT CTCTATTGCT GCTCTCTCAC TCCCCCATGA GGTACAGCAG

AAAGGAGAAC TATCCAAAAC TAATTTCCTC TGACATGTAA GACGAATGAT TTAGGTACGT

CAAAGCAGTA GTCAAGGAGG AAAGGGATAG TCCAAAGACT TAACTGGTTC ATATTGGACT

GATAATCTCT TTAAATGGCT TTATGCTAGT TTGACCTCAT TTGTAAAATA TTTATGAGAA

AGTTCTCATT TAAAATGAGA TCGTTGTTTA CAGTGTATGT ACTAAGCAGT AAGCTATCTT

CAAATGTCTA AGGTAGTAAC TTTCCATAGG GCCTCCTTAG ATCCCTAAGA TGGCTTTTTC

TCCTTGGTAT TTCTGGGTCT TTCTGACATC AGCAGAGAAC TGGAAAGACA TAGCCAACTG

CTGTTCATGT TACTCATGAC TCCTTTCTCT AAAACTGCCT TCCACAATTC ACTAGACCAG

AAGTGGACGC AACTTAAGCT GGGATAATCA CATTATCATC TGAAAATCTG GAGTTGAACA

GCAAAAGAAG ACAACATTTC TCAAATGCAC ATCTCATGGC AGCTAAGCCA CATGGCTGGG

ATTTAAAGCC TTTAGAGCCA GCCCATGGCT TTAGCTACCT CACTATGCTG CTTCACAAAC

CTTGCTCCTG TGTAAAACTA TATTCTCAGT GTAGGGCAGA GAGGTCTAAC ACCAACATAA

GGTACTAGCA GTGTTTCCCG TATTGACAGG AATACTTAAC TCAATAATTC TTTTCTTTTC

CATTTAGTAA CAGTTGTGAT GACTATGTTT CTATTCTAAG TAATTCCTGT ATTCTACAGC

AGATACTTTG TCAGCAATAC TAAGGGAAGA AACAAAGTTG AACCGTTTCT TTAATAA
```

-continued

CD86 (SEQ ID NO: 3):
```
AGTCATTGCC GAGGAAGGCT TGCACAGGGT GAAAGCTTTG CTTCTCTGCT GCTGTAACAG

GGACTAGCAC AGACACACGG ATGAGTGGGG TCATTTCCAG ATATTAGGTC ACAGCAGAAG

CAGCCAAAAT GGATCCCCAG TGCACTATGG GACTGAGTAA CATTCTCTTT GTGATGGCCT

TCCTGCTCTC TGCTAACTTC AGTCAACCTG AAATAGTACC AATTTCTAAT ATAACAGAAA

ATGTGTACAT AAATTTGACC TGCTCATCTA TACACGGTTA CCCAGAACCT AAGAAGATGA

GTGTTTTGCT AAGAACCAAG AATTCAACTA TCGAGTATGA TGGTATTATG CAGAAATCTC

AAGATAATGT CACAGAACTG TACGACGTTT CCATCAGCTT GTCTGTTTCA TTCCCTGATG

TTACGAGCAA TATGACCATC TTCTGTATTC TGGAAACTGA CAAGACGCGG CTTTTATCTT

CACCTTTCTC TATAGAGCTT GAGGACCCTC AGCCTCCCCC AGACCACATT CCTTGGATTA

CAGCTGTACT TCCAACAGTT ATTATATGTG TGATGGTTTT CTGTCTAATT CTATGGAAAT

GGAAGAAGAA GAAGCGGCCT CGCAACTCTT ATAAATGTGG AACCAACACA ATGGAGAGGG

AAGAGAGTGA ACAGACCAAG AAAAGAGAAA AAATCCATAT ACCTGAAAGA TCTGATGAAG

CCCAGCGTGT TTTTAAAAGT TCGAAGACAT CTTCATGCGA CAAAAGTGAT ACATGTTTTT

AATTAAAGAG TAAAGCCCAT ACAAGTATTC ATTTTTTCTA CCCTTTCCTT TGTAAGTTCC

TGGGCAACCT TTTTGATTTC TTCCAGAAGG CAAAAAGACA TTACCATGAG TAATAAGGGG

GCTCCAGGAC TCCCTCTAAG TGGAATAGCC TCCCTGTAAC TCCAGCTCTG CTCCGTATGC

CAAGAGGAGA CTTTAATTCT CTTACTGCTT CTTTTCACTT CAGAGCACAC TTATGGGCCA

AGCCCAGCTT AATGGCTCAT GACCTGGAAA TAAAATTTAG GACCAATACC TCCTCCAGAT

CAGATTCTTC TCTTAATTTC ATAGATTGTG TTTTTTTTTT AAATAGACCT CTCAATTTCT

GGAAAACTGC CTTTTATCTG CCCAGAATTC TAAGCTGGTG CCCCACTGAA TTTTGTGTAC

CTGTGACTAA ACAACTACCT CCTCAGTCTG GGTGGGACTT ATGTATTTAT GACCTTATAG

TGTTAATATC TTGAAACATA GAGATCTATG TACTGTAATA GTGTGATTAC TATGCTCTAG

AGAAAGTCT ACCCCTGCTA AGGAGTTCTC ATCCCTCTGT CAGGGTCAGT AAGGAAAACG

GTGGCCTAGG GTACAGGCAA CAATGAGCAG ACCAACCTAA ATTTGGGAA ATTAGGAGAG

GCAGAGATAG AACCTGGAGC CACTTCTATC TGGGCTGTTG CTAATATTGA GGAGGCTTGC

CCCACCCAAC AAGCCATAGT GGAGAGAACT GAATAAACAG GAAAATGCCA GAGCTTGTGA

ACCCTGTTTC TCTTGAAGAA CTGACTAGTG AGATGGCCTG GGGAAGCTGT GAAAGAACCA

AAAGAGATCA CAATACTCAA AAGAGAGAGA GAGAGAAAAA AGAGAGATCT TGATCCACAG

AAATACATGA AATGTCTGGT CTGTCCACCC CATCAACAAG TCTTGAAACA AGCAACAGAT

GGATAGTCTG TCCAAATGGA CATAAGACAG ACAGCAGTTT CCCTGGTGGT CAGGGAGGGG

TTTTGGTGAT ACCCAAGTTA TTGGGATGTC ATCTTCCTGG AAGCAGAGCT GGGGAGGGAG

AGCCATCACC TTGATAATGG GATGAATGGA AGGAGGCTTA GGACTTTCCA CTCCTGGCTG

AGAGAGGAAG AGCTGCAACG GAATTAGGAA GACCAAGACA CAGATCACCC GGGGCTTACT

TAGCCTACAG ATGTCCTACG GGAACGTGGG CTGGCCCAGC ATAGGGCTAG CAAATTTGAG

TTGGATGATT GTTTTTGCTC AAGGCAACCA GAGGAAACTT GCATACAGAG ACAGATATAC

TGGGAGAAAT GACTTTGAAA ACCTGGCTCT AAGGTGGGAT CACTAAGGGA TGGGGCAGTC

TCTGCCCAAA CATAAAGAGA ACTCTGGGGA GCCTGAGCCA CAAAAATGTT CCTTTATTTT

ATGTAAACCC TCAAGGGTTA TAGACTGCCA TGCTAGACAA GCTTGTCCAT GTAATATTCC

CATGTTTTTA CCCTGCCCCT GCCTTGATTA GACTCCTAGC ACCTGGCTAG TTTCTAACAT

GTTTTGTGCA GCACAGTTTT TAATAAATGC TTGTTACATT CATTTAAAAA AAAAAAAA
```

Exemplary antisense oligonucleotides encoding human CD40, human CD80, and human CD86 are provided below:

```
Human CD40 (SEQ ID NO: 4):
ACTGGGCGCC CGAGCGAGGC CTCTGCTGAC

Human CD80 (SEQ ID NO: 5):
TTGCTCACGT AGAAGACCCT CCCAGTGATG

Human CD86 (SEQ ID NO: 6):
AAGGAGTATT TGCGAGCTCC CCGTACCTCC

Human CD80 (SEQ ID NO: 7):
TTGCTCACGT AGAAGACCCT CCAGTGATG
```

In some embodiments, the antisense compounds are antisense oligonucleotides. The antisense oligonucleotides can be any suitable length to allow for specific binding to the target and modulation of gene expression. The length of an antisense oligonucleotide can vary, but is typically about 15 to about 40 nucleotides, including 15, 16, 17, 18, 19, 20, 21, 22, 23, 24, 25, 26, 27, 28, 29, 30, 31, 32, 33, 34, 35, 36, 37, 38, 39 or 40 nucleotides. In some embodiments, the antisense oligonucleotides are about 20 to about 35 nucleotides in length. The antisense oligonucleotides can be DNA, RNA or analogs thereof. Furthermore, the oligonucleotides provided herein can be unmodified or can comprise one or more modifications, such as modified internucleoside linkages, modified sugar moieties, modified bases, or a combination thereof. Oligonucleotide modifications are described in detail below.

In other embodiments, the antisense compounds are siRNA molecules. siRNAs useful for the disclosed methods include short double-stranded RNA from about 17 nucleotides to about 30 nucleotides in length, preferably from about 20 to about 35 nucleotides in length, such as about 25 to about 32 nucleotides in length. In this context, "about" indicates within one nucleotide. The siRNAs are made up of a sense RNA strand and a complementary antisense RNA strand annealed together by standard Watson-Crick base-pairing interactions. The sense strand includes a nucleic acid sequence that is substantially identical to a nucleic acid sequence contained within the target CD40, CD80 or CD86 gene product. In some non-limiting examples, a siRNA nucleic acid sequence that is "substantially identical" to a target sequence is a nucleic acid sequence that is identical to the target sequence, or that differs from the target sequence by one, two or three nucleotides. The sense and antisense strands of the siRNA can either include two complementary, single-stranded RNA molecules, or can be a single molecule having two complementary portions (which are base-paired) separated a single-stranded "hairpin" region.

The siRNA can also be altered RNA that differs from naturally-occurring RNA by the addition, deletion, substitution and/or alteration of one or more nucleotides. Such alterations can include addition of non-nucleotide material, such as to one or both of the ends of the siRNA or to one or more internal nucleotides of the siRNA; modifications that make the siRNA resistant to nuclease digestion; or the substitution of one or more nucleotides in the siRNA with deoxyribonucleotides. One or both strands of the siRNA can also include a 3' overhang. As used herein, a "3' overhang" refers to at least one unpaired nucleotide extending from the 3'-end of a duplexed RNA strand. Thus, in certain embodiments, the siRNA includes at least one 3' overhang of from 1 to about 6 nucleotides (which includes ribonucleotides or deoxyribonucleotides) in length, from 1 to about 5 nucleotides in length, from 1 to about 4 nucleotides in length, or from about 2 to about 4 nucleotides in length. In a particular embodiment, the 3' overhang is present on both strands of the siRNA and is 2 nucleotides in length. For example, each strand of the siRNA can comprise 3' overhangs of dithymidylic acid ("TT") or diuridylic acid ("uu").

In other embodiments, the antisense compound is a ribozyme. Ribozymes are nucleic acid molecules having a substrate binding region that is complementary to a contiguous nucleic acid sequence of a CD40, CD80 or CD86 gene product, and which is able to specifically cleave this gene product. The substrate binding region need not be 100% complementary to the target CD40, CD80 or CD86 gene product. For example, the substrate binding region can be, for example, at least about 50%, at least about 75%, at least about 85%, or at least about 95% complementary to a contiguous nucleic acid sequence in a CD40, CD80 or CD86 gene product. The enzymatic nucleic acids can also include modifications at the base, sugar, and/or phosphate groups.

Antisense compounds, such as antisense oligonucleotides, siRNAs and ribozymes, can be produced chemically or biologically, or can be expressed from a recombinant plasmid or viral vector. Exemplary methods for producing and testing antisense compounds are well known in the art (see, for example, U.S. Pat. Nos. 5,849,902 and 4,987,071; U.S. Patent Application Publication Nos. 2002/0173478 and 2004/0018176; Stein and Cheng, Science 261:1004, 1993; Werner and Uhlenbeck, *Nucl. Acids Res.* 23:2092-2096, 1995; Hammann et al., *Antisense and Nucleic Acid Drug Dev.* 9:25-31). The antisense oligonucleotides can specifically inhibit CD40, CD80 or CD86 mRNA expression by at least 10%, 20%, 30%, 40%, 50%, 55% 60%, 65%, 70%, 75%, 80%, 90% or 95% of that seen with vehicle treated controls i.e., cells exposed only to the transfection agent and the PBS vehicle, but not an antisense oligonucleotide.

The oligonucleotides can be selected from the group consisting of the nucleic acid sequence set forth as SEQ ID NO: 4, SEQ ID NO: 5, SEQ ID NO: 6, or SEQ ID NO: 7 and combinations thereof. Antisense oligonucleotides comprising about 70, 80, 85, 90, 95, 96, 97, 98, or 99% sequence homology over a sequence of about 15 nucleotides to CD40, CD80, or CD86 may also been used in the methods, compositions, and kits of this disclosure. Antisense oligonucleotides comprising more than about 70, 80, 85, 90, 95, 96, 97, 98, or 99% sequence homology over a sequence of about 15 nucleotides to CD40, CD80, or CD86 may also been used in the methods, compositions, and kits of this disclosure. Antisense oligonucleotides comprising less than about 70, 80, 85, 90, 95, 96, 97, 98, or 99% sequence homology over a sequence of about 15 nucleotides to CD40, CD80, or CD86 may also been used in the methods, compositions, and kits of this disclosure.

In various aspects of the disclosure, delivery of oligonucleotides to dendritic cells to induce tolerogenicity may be done by contacting dendritic cells with antisense transcripts or by contacting dendritic cells with particles containing antisense transcripts. Receptor endocytosis may mediate uptake of naked antisense or particles by dendritic cells. Oligonucleotides may be modified to enhance receptor-mediated endocytosis. Furthermore, oligonucleotides may be surface bound, coated, or encapsulated in particles that dendritic cells phagocytosis.

Specific examples of antisense oligonucleotides directed against transcripts of CD40, CD80, and CD86 are disclosed in the examples herein. Additional antisense oligonucleotides may be designed to be effective in binding the CD40, CD80 and/or CD86 transcripts to achieve the effects described herein. Such oligonucleotides may incorporate modifications known in the art including, but not limited to, thioation, methylation and methoxyethylation and that the location and number of such modifications may be varied to achieve an optimal effect. These oligonucleotides may be designed to induce immune tolerance in dendritic cell populations.

Oligonucleotides may be short, single-stranded DNA or RNA molecules. Oligonucleotides may be fragments of DNA. Oligonucleotides may be a primer sequence. Oligonucleotides may be complementary to a specific sequence. Oligonucleotides may be antisense oligonucleotides. Oligonucleotides may be aptamers. Oligonucleotides may be unmodified. Modified forms of oligonucleotides may include those having at least one modified internucleotide linkage. "Modified forms" of oligonucleotides include, without limitation, modified internucleoside linkages and/or modified bases. Oligonucleotides may be morpholinos with non-natural backbones.

The oligonucleotide may be all or in part a peptide nucleic acid. Other modified internucleoside linkages may include at least one phosphorothioate linkage. Still other modified oligonucleotides may include those comprising one or more universal bases. "Universal base" may refer to molecules capable of substituting for binding to any one of A, C, G, T and U in nucleic acids by forming hydrogen bonds without significant structure destabilization.

Specific examples of oligonucleotides may include those containing modified backbones or non-natural internucleoside linkages. Oligonucleotides having modified backbones may include those that retain a phosphorus atom in the backbone and those that may not have a phosphorus atom in the backbone. Modified oligonucleotides that may not have a phosphorus atom in their internucleoside backbone may be considered to be within the meaning of "oligonucleotide".

Modified oligonucleotide backbones may contain a phosphorus atom including, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Also contemplated may be oligonucleotides having inverted polarity comprising a single 3' to 3' linkage at the 3'-most internucleotide linkage. i.e. a single inverted nucleoside residue which may be abasic (the nucleotide is missing or has a hydroxyl group in place thereof). Salts, mixed salts and free acid forms may also be contemplated.

Modified oligonucleotide can have backbones that may be formed by short chain alkyl or cycloalkyl internucleoside linkages, mixed heteroatom and alkyl or cycloalkyl internucleoside linkages, or one or more short chain heteroatomic or heterocyclic internucleoside linkages. These may include those having morpholino linkages; siloxane backbones; sulfide, sulfoxide and sulfone backbones; formacetyl and thioformacetyl backbones, methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Modified oligonucleotides may include oligonucleotide mimetics wherein both one or more sugar and/or one or more internucleotide linkage of the nucleotide units may be replaced with "non-naturally occurring" groups. The bases of the oligonucleotide may be maintained for hybridization with the target polynucleotide (e.g. a peptide nucleic acid (PNA)). In PNA compounds, the sugar-backbone of an oligonucleotide may be replaced with an amide containing backbone.

Oligonucleotides may be provided with phosphorothioate backbones and oligonucleosides with heteroatom backbones, and including $-CH_2-NH-O-CH_2-$, $-CH_2-N(CH_3)-O-CH_2-$, $-CH_2-O-N(CH_3)-CH_2-$, $-CH_2-N(CH_3)-N(CH_3)-CH_2$, and $-O-N(CH_3)-H_2-CH_2-$. In various forms, the linkage between two successive monomers in the oligonucleotide may consist of 2 to 4, in some cases 3, groups/atoms selected from $-CH_2-$, $-O-$, $-S-$, $-NR^H$, $>C=O$, $>C=NR^H$, $>C=S$, $Si(R")_2-$, $-SO-$, $-S(O)_2-$, $-P(O)_2-$, $-PO(BH_3)-$, $-P(O,S)-$, $-P(S)_2-$, $-PO(R")-$, $-PO(OCH_3)-$, and $-PO(NHR^H)$, where RH is selected from hydrogen and $C_{1-4}$-alkyl, and R" is selected from $C_{1-6}$-alkyl and phenyl. Illustrative examples of such linkages are $-CH_2-CH_2-CH_2-$, $-CH_2-CO-CH_2-$, $-CH_2-CHOH-CH_2-$, $-O-CH_2-$, $-O-CH_2-CH_2-$, $-O-CH_2-CH=$ (including $R^5$ when used as a linkage to a succeeding monomer), $-CH_2-CH_2-O-$, $-NR^H-CH_2CH_2-$, $-CH_2-CH_2-NR^H$, $-CH_2-NR^H-CH_2-$, $-O-CH_2-CH_2-NR"-NR^H-CO-O-$, $-NR^H-CO-NR^H$, $NR^H-CS-NR^H$, $NR^H-C(=NR^H)-NR^H$, $NR^H-CO-CH_2-NR^H-O-CO-O-$, $-O-CO-CH_2-O-$, $-O-CH_2-CO-O-$, $-CH_2-CO-NR^H$, $-O-CO-NR^H$, $-NR^H-CO-CH_2-$, $-O-CH_2-CO_2-NR^H$, $-O-CH_2-CH_2-NR$, $CH=N^H$, $CH_2-NR^H-O-$, $-CH_2-O-N=$ (including $R^5$ when used as a linkage to a succeeding monomer), $-CH_2-O-NR^H-$, $-CO-NR^H-CH_2-$, $-CH_2-NR^H-O-$, $-CH_2-NR^H-CO-$, $-O-NR^H-CH_2-$, $-O-NR^H$, $-O-CH_2-S-$, $-S-CH_2-O-$, $-CH_2-CH_2-S-$, $-CH_2CH_2-S-$, $-S-CH_2CH=$ (including $R^5$ when used as a linkage to a succeeding monomer), $-S-CH_2-CH_2-$, $-S-CH_2-CH_2-O-$, $-S-CH_2CH_2-S-$, $-CH_2-S-CH_2-$, $-CH_2-SO-CH_2-$, $-CH_2-SO_2-CH_2-$, $-O-SO-O-$, $-O-S(O)_2-O-$, $-O-S(O)_2-CH_2-$, $-O-S(O)_2-NR^H-$, $-NR^H-S(O)_2CH_2-$; $-O-S(O)_2-CH_2-$, $-O-P(O)_2-O-$, $-O-P(O,S)-O-$, $-O-P(S)_2-O-$, $-S-P(O)_2-O-$, $-S-P(O,S)-O-$, $-S-P(S)_2-O-$, $-O-P(O)_2-S-$, $-O-P(O,S)-S-$, $-O-P(S)_2-S-$, $-S-P(O)_2-S-$, $-S-P(O,S)-S-$, $-S-P(S)_2-S-$, $-O-PO(R")-O-$, $-O-PO(OCH_3)-O-$, $-O-PO(OCH_2CH_3)-O-$, $-O-PO(OCH_2CH_2S-R)-O-$, $-O-PO(BH_3)-O-$, $-O-PO(NHR^N)-O-$, $-O-P(O)_2-NR" H-$, $-NR^H-P(O)_2-O-$, $-O-P(O,NR^H)-O-$, $-CH_2-P(O)_2-O-$, $-O-P(O)_2CH_2-$, and $-O-Si(R")_2-O-$; among which $-CH_2-CO-NR^H-$, $-CH_2-NR^H-O-$, $-S-CH_2-O-$, $-O-P(O)_2-O-P(=O,S)-O-$, $-O-P(S)_2-O-$, $-NR^H-P(O)_2-O-$, $-O-P(O,NR^H)-O-$, $-O-PO(R")-O-$, $-O-PO(CH_3)-O-$, and $-O-PO(NHR^N)-O-$, where RH may be selected from hydrogen and $C_{1-4}$-alkyl, and R" may be selected from $C_{1-6}$-alkyl and phenyl.

Modified oligonucleotides may also contain one or more substituted sugar moieties. In certain aspects, oligonucleotides may comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Other embodiments may include $O[(CH_2)_nO]_mCH_3$, $O(CH_2)_nOCH_3$, $O(CH_2)_n NH_2$, $O(CH_2)_nCH_3$, $O(CH_2)_nONH_2$, and $O(CH_2)_nON [(CH_2)_nCH_3]_2$, where n and m may be from 1 to about 10. Other oligonucleotides may comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In one aspect, a modification may include 2'-methoxyethoxy (2'-O—$CH_2CH_2OCH_3$), i.e., an alkoxyalkoxy group. Other modifications may include 2'-dimethylaminooxyethoxy, i.e., a $O(CH_2)_2ON(CH_3)_2$ group, and 2'-dimethylaminoethoxyethoxy, i.e., 2'-O—$CH_2$—O—$CH_2$—$N(CH_2$—$N(CH_3)_2$, also described in examples herein.

Still other modifications may include 2'-methoxy (2'-O—$CH_3$), 2'-aminopropoxy (2'-$OCH_2CH_2CH_2NH_2$), 2'-allyl (2'-$CH_2$—CH═$CH_2$), 2'-O-allyl (2'-O—$CH_2$—CH═$H_2$) and 2'-fluoro (2'-F). The 2'-modification may be in the arabino (up) position or ribo (down) position. In one aspect, a 2'-arabino modification is 2'-F. Similar modifications may also be made at other positions on the oligonucleotide, for example, at the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

In one aspect, a modification of the sugar may include Locked Nucleic Acids (LNAs) in which the 2'-hydroxyl group may be linked to the 3' or 4' carbon atom of the sugar ring, thereby forming a bicyclic sugar moiety. The linkage in certain aspects may be a methylene (—$CH_2$—)$_n$ group bridging the 2' oxygen atom and the 4' carbon atom wherein n may be 1 or 2.

Oligonucleotides may also include base modifications or substitutions. As used herein, "unmodified" or "natural" bases may include the purine bases adenine (A) and guanine (G), and the pyrimidine bases thymine (T), cytosine (C) and uracil (U). Modified bases may include other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine (1H-pyrimido[5,4-b][1,4]benzoxazin-2(3H)-one), phenothiazine cytidine (1H-pyrimido[5,4-b][1.4]benzothiazin-2 (3H)-one), G-clamps such as a substituted phenoxazine cytidine (e.g. 9-(2-aminoethoxy)-H-pyrimido[5,4-b][1,4] benzox-azin-2(3H)-one), carbazole cytidine (2H-pyrimido [4,5-b]indol-2-one), pyridoindole cytidine (H-pyrido[3',2':4, 5]pyrrolo[2,3-d]pyrimidin-2-one). Modified bases may also include those in which the purine or pyrimidine base is replaced with other heterocycles, for example 7-deazaadenine, 7-deazaguanosine, 2-aminopyridine and 2-pyridone. Certain of these bases may be useful for increasing the binding affinity and may include 5-substituted pyrimidines, 6-azapyrimidines and N-2, N-6 and O-6 substituted purines, including 2-aminopropyladenine, 5-propynyluracil and 5-propynylcytosine, 5-methylcytosine substitutions have been shown to increase nucleic acid duplex stability by 0.6-1.2° C. and may be, in certain aspects, combined with 2'-O-methoxyethyl sugar modifications.

A "modified base" or other similar term may refer to a composition which may pair with a natural base (e.g., adenine, guanine, cytosine, uracil, and/or thymine) and/or may pair with a non-naturally occurring base. In certain aspects, the modified base may provide a $T_m$ differential of 15, 12, 10, 8, 6, 4, or 2° C. or less.

A "nucleobase" may refer to the naturally occurring nucleobases adenine (A), guanine (G), cytosine (C), thymine (T) and uracil (U) as well as non-naturally occurring nucleobases such as xanthine, diaminopurine, 8-oxo-$N^6$-methyladenine, 7-deazaxanthine, 7-deazaguanine, $N^4,N^4$-ethanocytosin, N',N'-ethano-2,6-diaminopurine, 5-methylcytosine (mC), 5-($C^3$-$C^6$)-alkynyl-cytosine, 5-fluorouracil, 5-bromouracil, pseudoisocytosine, 2-hydroxy-5-methyl-4-triazolopyridin, isocytosine, isoguanine, inosine and the "non-naturally occurring" nucleobases. The term nucleobase thus includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., Angewandte Chemie, International Edition, 1991, 30, 613-722. The term "nucleosidic base" or "base unit" may be further intended to include compounds such as heterocyclic compounds that may serve like nucleobases including certain "universal bases" that may not be nucleosidic bases in the most classical sense but may serve as nucleosidic bases. Especially mentioned as universal bases may be 3-nitropyrrole, optionally substituted indoles (e.g., 5-nitroindole), and optionally substituted hypoxanthine. Other desirable universal bases may include, pyrrole, diazole or triazole derivatives, including those universal bases known in the art.

The oligonucleotides of the invention may be modified at one base position. The oligonucleotides may be modified at two, three, four, five, six, seven, eight, nine, ten or more base positions. Any modification may be contemplated by the invention as long as the resulting oligonucleotide may retain the ability to bind to its target transcript.

Particles

The methods, compositions, devices, and kits of this disclosure may be used with any suitable particle, including polymeric microspheres and polymeric nanospheres and other types of particles. Particles may serve to localize or to partition various entities, including nucleic acids, proteins, peptides, antibodies, cells, chromosomes, oligonucleotides, biomolecules, DNA, RNA, and the like. Oligonucleotides may include antisense oligonucleotides, modified oligonucleotides, polynucleotides and the like. Proteins may include growth factors, cytokines (e.g. transforming growth factor beta (TGF-β)), chemokines, and the like. Biomolecules may include cell media components, serum, antibiotics, antifungicides, labeling moieties (e.g. fluorescent, magnetic), and the like. Various entities may be associated with the surface of the particle, may be affixed directly to the surface of the particle, may be affixed to the surface of the particle through other oligonucleotides sequences, may be affixed to the surface of the particle through peptide sequences, may be suffused throughout the particle, or may be directly coupled to the particle through chemical linkages. Other entities including media components, serum, cytokines, chemokines, growth factors, biomolecules and the like may be suffused throughout the particle.

Particles may serve as a solid surface. The solid surface may be rigid or may be flexible. The solid surface may be porous or may be non-porous. The solid surface may be solid or semi-solid.

Particles may serve to localize samples. Entities (e.g. oligonucleotides, peptides, proteins, cells and the like) may be associated with the surface of the particle. Entities may be located throughout the particle. Entities may be directly attached to the particle. Direct attachment may comprise adsorption or chemical linkage, such as a covalent or ionic bond. The entities may be associated with the entire surface, with half the surface, or with a portion of the surface. The entities may be located throughout the particle, located within half the particle, or located within a portion of the particle.

Particle Characteristics

The methods, compositions, and kits of this disclosure may be used with any suitable particle. A particle may refer to a carrier, a capsule, a vesicle, a micelle, a microsphere, a microparticle, a nanosphere, a nanoparticle or the like. A particle may be porous, non-porous, solid, or hollow.

A particle may be dissolvable, disruptable, or degradable. A particle may not be dissolvable or degradable. Changes in temperature or pH may trigger particle disruption or degradation. In some cases, particles exposed to low pH acidic conditions (e.g. intracellular lysosomal and endosomal compartments) may degrade. In some cases, exposure to aqueous solution may trigger particle disruption or degradation. In some cases, particles exposed to aqueous solution may degrade by hydrolytic degradation.

The particle may be a bead (e.g. gel bead, a solid bead, or a semi-solid bead). A gel bead may be a hydrogel bead. A gel bead may be formed from molecular monomers, such as polymeric monomers. A semi-solid bead may be a liposomal bead. A semi-solid bead may be formed from molecular components, such as lipids. A solid bead may be a gold bead. A solid bead may be a polystyrene bead. Gel beads may range in material hardness. In one non limiting example, a gel bead formed from polymeric monomers such as polyethylene glycol (PEG) may be softer than a bead formed from polymer monomers of silica or polystyrene, which may be harder beads than PEG beads. Solid beads may also be formed from metals including iron oxide, gold, and silver.

The particle may contain molecular monomers, which may form a polymer network by copolymerizing individual monomers. In some cases, the particle may contain prepolymers, oligomers capable of further polymerization. For example, polyurethane beads may be prepared using prepolymers. The particle may contain individual polymers that may be further polymerized together.

Examples of natural polymers include proteins and sugars such as chitosan, dextran, collagen, carrageenan, agarose, alginate, or natural polymers thereof. Examples of synthetic polymers include carboxylic acids, vinyl acetate, acrylamide, acrylate, ethylene glycol, urethanes, lactic acid, silica, polystyrene, and oligomers and polymers thereof. Particles may be formed from monomers of N-vinylpyrrolidone. Particles may be formed from polymers of polyvinylpyrrolidone. Particles may be formed from polymers of ethylene oxide, including polyethylene glycol. Particles may be formed from various weight and volume ratios of polyethylene glycol and polyvinylpyrrolidone polymers. Particles may also be formed from materials other than polymers, including lipids, micelles, ceramics, glass-ceramics, material composites, metals and others.

Molecular monomers may combine with themselves by reacting at double bond sites to form oligomers or polymers. Alternatively, molecular monomers (e.g. polymeric monomer such as acrylic acid) may have a substantial number of chemically modifiable groups, such as thiol groups. Thus, polymeric monomers may be connected together specifically with a chemical crosslinker to form oligomers or polymers.

The surface of the particles may have modifications. The surface of the particles may be modified to be hydrophobic, hydrophilic, positively charged, negatively charged, uncharged, or the like. The surface of the particles may have chemical modifications such that chemical groups are added (e.g. carboxyl groups, thiol groups, di-sulfide groups, and the like).

The particles may have entities attached to their surface. Entities, for example, may include nucleic acids, proteins, peptides, antibodies, cells, chromosomes, oligonucleotides, antisense oligonucleotides, modified oligonucleotides, polynucleotides, DNA, RNA, or biomolecules (e.g. transforming growth factor beta (TGF-$\beta$), retinoic acid (RA)). Such entities may be covalently attached or attached by other means such as adsorption. In some cases, entities, such as oligonucleotides may be physically encapsulated within particles, embedded within particles, or may be directly attached to particle components, such as individual polymeric monomers, such that entities are suffuse throughout the particle.

Making Particles

In making the particles that are used for treatment of autoimmune or inflammatory conditions in a subject, one, two, three or more entities (e.g. oligonucleotides, cytokines, biomolecules) may be dissolved in aqueous solution and may be combined with one or more molecular monomers (e.g. one or more water soluble polymer(s)) and optionally a polycation. In some cases, the one, two, three or more oligonucleotides are antisense oligonucleotides. In some cases, individual oligonucleotides are dissolved in aqueous solution, wherein each solution contains one of the oligonucleotides. The individual aliquots from each oligonucleotide may then be combined.

In one non-limiting example, the final solution containing oligonucleotides may contain about 10 mg/ml of each oligonucleotide. Subsequently, the aqueous solution containing one, two, three, or more oligonucleotides may be combined with one or more molecular monomers (e.g. water soluble polymer (s)) and optionally a polycation. This solution may be incubated (e.g. at about 60-70° C.), may be cooled (e.g. to about 23° C.), and the excess polymer may be removed.

Particles may be monodisperse. Particles may be polydisperse. Particles may be monodisperse with less than about 1%, 5%, 10%, 15%, 20%, or 25% variance. Particles may be monodisperse with about 1%, 5%, 10%, 15%, 20%, or 25% variance. Particles may be monodisperse with about 10% variance.

For microspheres, the nucleic acids may comprise between about 30 and about 100 weight percent of the microspheres. Average particle size of microspheres may be about: 0.001 µm, 0.01 µm, 0.1 µm, 0.25 µm, 0.5 µm, 0.75

µm, 1 µm, 1.5 µm, 2 µm, 2.5 µm, 3 µm, 3.5 µm, 4 µm, 4.5 µm, 5 µm, 10 µm, 20 µm, 25 µm, or 50 µm. Average particle size of microspheres may be greater than about: 0.001 µm, 0.01 µm, 0.1 µm, 0.25 µm, 0.5 µm, 0.75 µm, 1 µm, 1.5 µm, 2 µm, 2.5 µm, 3 µm, 3.5p m, 4 µm, 4.5 µm, 5p m, 10 µm, 20 µm, 25 µm, 50 µm or more. Average particle size of microspheres may be less than about: 0.001 µm, 0.01 µm, 0.1 µm, 0.25 µm, 0.5 µm, 0.75 µm, 1 µm, 1.5 µm, 2 µm, 2.5 µm, 3 µm, 3.5 µm, 4 µm, 4.5 µm, 5 µm, 10 µm, 20 µm, 25 µm, or 50 µm. Average particle size of microspheres may not be greater than about 2 µm. Average particle size of microspheres may be between about 0.5 µm and about 2.5 µm. Average particle size of microspheres may be between about 1 µm and about 10 µm.

For nanospheres, the nucleic acids typically comprise between about 30 and about 100 weight percent of the nanospheres. Average particle size of nanospheres may be about: 0.1 nm, 0.5 nm, 1 nm, 5 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 150 nm, 200 nm, 250 nm, 300 nm, 350 nm, 400 nm, 450 nm, 500 nm, 600 nm, 650 nm, 700 nm, 710 nm, 720 nm, 730 nm, 740 nm, 750 nm, 760 nm, 770 nm, 780 nm, 790 nm 800 nm, 850 nm, 900 nm, or 1000 nm. Average particle size of nanospheres may be greater than about: 0.1 nm, 0.5 nm, 1 nm, 5 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 150 nm, 200 nm, 250 nm, 300 nm, 350 nm, 400 nm, 450 nm, 500 nm, 600 nm, 650 nm, 700 nm, 710 nm, 720 nm, 730 nm, 740 nm, 750 nm, 760 nm, 770 nm, 780 nm, 790 nm 800 nm, 850 nm, 900 nm, 1000 nm or more. Average particle size of nanospheres may be less than about: 0.1 nm, 0.5 nm, 1 nm, 5 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 150 nm, 200 nm, 250 nm, 300 nm, 350 nm, 400 nm, 450 nm, 500 nm, 600 nm, 650 nm, 700 nm, 710 nm, 720 nm, 730 nm, 740 nm, 750 nm, 760 nm, 770 nm, 780 nm, 790 nm 800 nm, 850 nm, 900 nm, or 1000 nm. Average particle size of nanospheres may not be greater than about 1000 nm. Average particle size of nanospheres may be between about 1 nm and about 500 nm. Average particle size of nanospheres may be between about 50 nm and about 1000 nm. The average particle size of nanospheres may be between about 650 nm and about 900 nm, about 700 nm and about 850 nm, about 710 nm and about 820 nm, or about 716 nm and about 818 nm.

The particle formulation may comprise about: 65%, 70%, 75%, 80%, 85%, 90% (w/w) or greater load of oligonucleotides. In such embodiments, the compositions may have a poly-L-lysine content of about: 6%, 6.5%, 7%, 7.5%, 8%, 8.5%, 9%, 9.5%, or 10% (w/w). In addition, the moisture content of the particles may vary. In some cases, the moisture content may be approximately 4%. In some cases, the oligonucleotides may be present in a ratio of about 1:1:1 of antisense CD40: antisense CD80: antisense CD86. In some cases, the oligonucleotides may be present in a ratio of about 1.5:1:1 or 1:1.5:1 or 1:1:1.5 of antisense CD40: antisense CD80: antisense CD86. In some cases, the oligonucleotides may be present in a ratio of about 2:1:1 or 1:2:1 or 1:1:2 of antisense CD40: antisense CD80: antisense CD86. In some cases, the oligonucleotides may be present in a ratio of about 3:1:1 or 1:3:1 or 1:1:3 of antisense CD40: antisense CD80: antisense CD86. In some cases, the oligonucleotides may be present in a ratio of about 1-3:1-3:1-3 of antisense CD40: antisense CD80: antisense CD86.

Aqueous solutions of one or more oligonucleotides may be combined with one or more polycations. In some cases, the one or more polycations may include poly-lysine and poly-ornithine. Others may include polyethyleneimine (PEI), prolamine, protamine, polyvinyl pyrrolidone (PVP), polyarginine, vinylamine, and derivatives of positively-charged polysaccharides, such as positively charged chitosan, and combinations thereof. The polycation solution may be at volumetric ratios of polycation:oligonucleotide of from about 1:1 to about 4:1. Commonly used polycations include poly-L-lysine.HBr (e.g. up to about 70,000 Daltons) and poly-L-ornithine.HBr (e.g. up to about 11,900 Daltons). Polycations may be added to the aqueous solution of one or more oligonucleotides from a stock solution of about 10 mg/ml.

Particle components (e.g. polymers) may function as phase-separation enhancing agents. Examples of suitable polymers may include linear or branched polymers, copolymers and block copolymers. These polymers may be water soluble, semi-water soluble, water-miscible, or soluble in a water-miscible solvent. Examples of polymers may include pharmaceutically acceptable additives such as polyethylene glycol (PEG) of various molecular weights, such as PEG 200, PEG 300, PEG 3350, PEG 8000, PEG 10000, PEG 20000, and others, and poloxamers of various molecular weights such as poloxamer 188 and Pluronic F127 or Pluronic F68. In some cases, the polymer may be polyvinylpyrrolidone (PVP). In other cases, the polymer may be hydroxyethylstarch. Other amphiphilic polymers may be used alone or in combinations. The phase-separation enhancing agent may also be a non-polymer such as a mixture of propylene glycol and ethanol.

A polymer solution of polyvinyl pyrrolidone and/or of polyethylene glycol may be prepared and combined with the other solutions. Heating, cooling, centrifuging and washing individual steps may be repeated one or more times to provide an aqueous suspension. The resulting aqueous suspensions may be frozen and lyophilized to form a dry powder of particles which may or may not comprise one or more entities (e.g. oligonucleotides) and one or more polycations.

In some cases, particles may be already formed. Preformed particles (e.g. carboxylate polystyrene microspheres, silica beads, glass beads, and the like) may be subjected to surface modifications (e.g. adding positive charge, adding negative change, and the like). Surface modifications may include incubating particles with peptides of a specific overall net charge, with DNA molecules, or with others to alter the overall net charge. Subsequently, entities may be directly attached to particles by adsorption, by covalent or ionic bonds or indirectly via linkages with peptides (e.g. $O_{10}H_6$ peptide) or DNA molecules previously attached to the particle surface.

Particles for Delivery

Particles may be suitable for in vivo delivery by an injectable route. Injectable routes can include: intravenous, intramuscular, subcutaneous, intraperitoneal, intrathecal, epidural, intra-arterial, intra-articular and the like. Other delivery routes that may be practiced include topical, oral, rectal, nasal, pulmonary, vaginal, buccal, sublingual, transdermal, transmucosal, optic or intraocular. The delivery route may be syringable delivery. Thus, in some cases, particles may be aspirated into a syringe and injected through fine needles.

Without being bound by any particular theory, it is believed that particles containing one or more oligonucleotides (e.g. antisense oligonucleotides) exemplified herein may down-regulate specific cell surface molecules (e.g. CD40, CD80 and CD86) in dendritic cell populations. In some cases, immature DCs cultured ex vivo may actively take up particles added to DC cultures. In some cases, particles are co-delivered with ex vivo cultured DCs (e.g. immature DCs, control DCs, tolerogenic DCs, DCs treated with one or more oligonucleotides, DCs treated with one or more particles, DCs treated with growth factors, hormones, cytokines, chemokines, or combinations thereof), wherein co-delivered DCs may actively take up particles before, during, after in vivo delivery (e.g. syringable injection), or any combination thereof. In some cases, endogenous dendritic cell populations may actively take up particles containing oligonucleotides (e.g. antisense oligonucleotides) after in vivo delivery (e.g. syringable injection). In some cases, both co-delivered and endogenous DCs may actively take up particles after in vivo delivery (e.g. syringable injection). In such embodiments, one or more oligonucleotides may suppress the expression of cell surface cell molecules (e.g. CD40. CD80 and CD86) in endogeneous and co-delivered dendritic cell populations. The administration of these oligonucleotide-containing particles after type 1 diabetes development in a mammal may reverse diabetes, may reduce diabetes, may promote survival of remaining beta cells, may reduce blood glucose levels to pre-diabetic levels, may increase suppressive B-cell populations, may increase tolerogenic DC populations, may decrease T-cell populations, may increase RA production in DC populations, and the like.

Injections

In the methods, compositions, and kits of this disclosure, dendritic cells and/or particles can be delivered by injection. These injections may occur by any route, including intravenous, intramuscular, subcutaneous, intraperitoneal, intrathecal, epidural, intra-arterial, intra-articular, intranodal (e.g. directly into a draining lymph node) and the like.

Injections may comprise a fluidic phase. In some cases, injections may comprise a solid suspension in a fluidic phase. In some cases, injections may comprise a semi-solid suspension in a fluidic phase. In some cases, injections may comprise a gel suspension in a fluidic phase. In some cases, injections may comprise one or more cells suspended in a fluidic phase. In some cases, injections may comprise one or more particles suspended in a fluidic phase. In some cases, injections may comprise one or more particles and one or more cells suspended in a fluidic phase. In some cases, injections may comprise one or more entities (e.g. cells, media, serum, growth factors, cytokines, biomolecules, and the like) in solution in a fluidic phase.

Subjects may receive about: $0.05\times10^6$, $0.1\times10^6$, $0.15\times10^6$, $0.2\times10^6$, $0.25\times10^6$, $0.3\times10^6$, $0.4\times10^6$, $0.5\times10^6$, $0.6\times10^6$, $0.7\times10^6$, $0.8\times10^6$, $0.9\times10^6$, $0.05\times10^7$, $0.1\times10^7$, $0.15\times10$, $0.2\times10^7$, $0.25\times10^7$, $0.3\times10^7$, $0.4\times10^7$, $0.5\times10^7$, $0.6\times10^7$, $0.7\times10^7$, $0.8\times10^7$, $0.9\times10^7$, $0.05\times10^8$, $0.1\times10^8$, $0.15\times10^8$, $0.2\times10^8$, $0.25\times10^8$, $0.3\times10^8$, $0.4\times10^8$, $0.5\times10^8$, $0.6\times10^8$, $0.7\times10^8$, $0.8\times10^8$, or $0.9\times10^8$ cells at each injection site. Subjects may receive more than about: $0.05\times10^6$, $0.1\times10^6$, $0.15\times10^6$, $0.2\times10^6$, $0.25\times10^6$, $0.3\times10^6$, $0.4\times10^6$, $0.5\times10^6$, $0.6\times10^6$, $0.7\times10^6$, $0.8\times10^6$, $0.9\times10^6$, $0.05\times10^6$, $0.1\times10^7$, $0.15\times10^7$, $0.2\times10^7$, $0.25\times10^7$, $0.3\times10$, $0.4\times10^7$, $0.5\times10^7$, $0.6\times10^7$, $0.7\times10^7$, $0.8\times10^7$, $0.9\times10^7$, $0.05\times10$, $0.1\times10$, $0.15\times10^8$, $0.2\times10^8$, $0.25\times10^8$, $0.3\times10^8$, $0.4\times10^8$, $0.5\times10^8$, $0.6\times10^8$, $0.7\times10^8$, $0.8\times10^8$, $0.9\times10^8$ cells at each injection site. Subjects may receive less than about: $0.05\times10^6$, $0.1\times10^6$, $0.15\times10^6$, $0.2\times10^6$, $0.25\times10^6$, $0.3\times10^6$, $0.4\times10^6$, $0.5\times10^6$, $0.6\times10^6$, $0.7\times10^6$, $0.8\times10^6$, $0.9\times10^6$, $0.05\times10^7$, $0.1\times10^7$, $0.15\times10^7$, $0.2\times10^7$, $0.25\times10^7$, $0.3\times10^7$, $0.4\times10^7$, $0.5\times10^7$, $0.6\times10^7$, $0.7\times10^7$, $0.8\times10^7$, $0.9\times10^7$, $0.05\times10^8$, $0.1\times10^8$, $0.15\times10^8$, $0.2\times10^8$, $0.25\times10^8$, $0.3\times10^8$, $0.4\times10^8$, $0.5\times10^8$, $0.6\times10^8$, $0.7\times10^8$, $0.8\times10^8$, $0.9\times10^8$ cells at each injection site.

Subjects may receive about: $0.5\times10^7$, $0.1\times10^7$, $0.15\times10^7$, $0.2\times10^7$, $0.25\times10^7$, $0.3\times10^7$, $0.4\times10^7$, $0.45\times10^7$, $0.5\times10^7$, $0.6\times10^7$, $0.75\times10^7$, $0.8\times10^7$, $0.9\times10^7$, $1.0\times10^7$, $1.2\times10^7$, or $1.6\times10^7$ cells at each of one or more treatments. Subjects may receive more than about: $0.5\times10^7$, $0.1\times10^7$, $0.15\times10^7$, $0.2\times10^7$, $0.25\times10^7$, $0.3\times10^7$, $0.4\times10^7$, $0.45\times10^7$, $0.5\times10^7$, $0.6\times10^7$, $0.75\times10^7$, $0.8\times10^7$, $0.9\times10^7$, $1.0\times10^7$, $1.2\times10^7$, or $1.6\times10^7$ cells at each of one or more treatments. Subjects may receive less than about: $0.5\times10^7$, $0.1\times10^7$, $0.15\times10^7$, $0.2\times10^7$, $0.25\times10^7$, $0.3\times10^7$, $0.4\times10^7$, $0.45\times10^7$, $0.5\times10^7$, $0.6\times10^7$, $0.75\times10^7$, $0.8\times10^7$, $0.9\times10^7$, $1.0\times10^7$, $1.2\times10^7$, or $1.6\times10^7$ cells at each of one or more treatments.

Subjects may receive a total cell number between about $1\times10^5$-about $6.4\times10^7$. Subjects may receive a total cell number of more than between about $1\times10^5$-about $6.4\times10^7$. Subjects may receive a total cell number of less than between about $1\times10^5$-about $6.4\times10^7$. In some non-limiting examples, subjects can receive between about $1\times10^6$ to about $3\times10^6$ cells, or between about $1\times10^6$ to about $5\times10^6$ cells, or between about $8\times10^5$ to about $4\times10^6$ at each of one or more treatments. In some cases, fluorescent imaging results may determine the subsequent number of cellular injections over a treatment course. In some cases, fluorescent imaging results may alter the number of cellular injections over a treatment course. In some cases, fluorescent imaging results may alter the total amount of cells per injection, the frequency of cellular injections over a treatment course, the concentration of cells per injection, or the anatomical location of cellular injections that the subject receives. In some cases, fluorescent imaging results may alter the composition of the injection.

Subjects may receive about: 0.00001, 0.0001, 0.001, 0.01, 0.1, 0.25, 0.5, 0.75, 1.0, 1.25, 1.5, 1.75, 2, 2.25, 2.5, 2.75, 3.0, 3.5, 4.0, 4.5, or 5.0 mg/kg (dry weight) of particles per injection. Subjects may receive more than about: 0.00001, 0.0001, 0.001, 0.01, 0.1, 0.25, 0.5, 0.75, 1.0, 1.25, 1.5, 1.75, 2, 2.25, 2.5, 2.75, 3.0, 3.5, 4.0, 4.5, 5.0 mg/kg (dry weight) of particles per injection. Subjects may receive less than about: 0.00001, 0.0001, 0.001, 0.01, 0.1, 0.25, 0.5, 0.75, 1.0, 1.25, 1.5, 1.75, 2, 2.25, 2.5, 2.75, 3.0, 3.5, 4.0, 4.5, or 5.0 mg/kg (dry weight) of particles per injection. Subjects may receive about 2 mg/kg (dry weight) of particles per injection.

Subjects may receive about: 1, 2, 3, 4, 5, 6, 7 particle injections per week. Subjects may receive more than about: 1, 2, 3, 4, 5, 6, 7 particle injections per week. Subjects may receive less than about: 1, 2, 3, 4, 5, 6, 7 particle injections per week. Subjects may receive particles with each cellular injection. In this case, subjects may receive particles in equal frequencies to cellular injection schedules disclosed above. In some cases, fluorescent imaging results may determine the subsequent number of particle injections over a treatment course. In some cases, fluorescent imaging results may alter the number of particle injections over a treatment course. In some cases, fluorescent imaging results may alter the total amount of particles per injection, the frequency of particle injections over a treatment course, the concentration of particles per injection, or the anatomical location of particle injections that the subject receives. In some cases, fluorescent imaging results may alter the composition of the injection.

The particles can be capable of being injected at a concentration of at least but not limited to about 10 μg of one or more oligonucleotides per mL of the composition being injected. For example, from about 150 to about 500 mg of one or more oligonucleotides may be injectable in a delivery volume of not more than about 1 mL, and generally less than about 2 mL for many applications. The dosage may be divided into two or three or more doses over the day or may be given in a single daily dose.

In various aspects, the particles may be capable of being injected at a concentration of at least but not limited to about 0.01 to about 1000 mg per mL of the composition being injected. In further aspects, the particles may be capable of being injected at a concentration of at least about: 0.02, 0.03, 0.04, 0.05, 0.06, 0.07, 0.08, 0.09, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 25, 30, 35, 40, 45, or 50 mg per mL or more of the composition being injected. In related aspects, the particles may be capable of being injected at a concentration of at least about: 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1000 mg per mL of the composition being injected.

The volume of a single injection may be about: 0.05, 0.075, 0.1, 0.125, 0.15, 0.175, 0.2, 0.25, 0.5, 0.75, 1, 1.25, 1.5, 1.75, 2, 2.5, 3, or 3.5 mL. The volume of a single injection may be more than about: 0.05, 0.075, 0.1, 0.125, 0.15, 0.175, 0.2, 0.25, 0.5, 0.75, 1, 1.25, 1.5, 1.75, 2, 2.5, 3, or 3.5 mL. The volume of the injection may be less than about: 0.05, 0.075, 0.1, 0.125, 0.15, 0.175, 0.2, 0.25, 0.5, 0.75, 1, 1.25, 1.5, 1.75, 2, 2.5, 3, or 3.5 mL. The volume of the injection may be between about 0.15 and about 0.2 mL. The volume of the injection may be between about 0.5 and about 2 mL.

In some embodiments, the number of injections sites for a single subject may be about: 1, 2, 3, 4, or 5. In some embodiments, the number of injections sites for a single subject may be more than 1, 2, 3, 4, 5, or more. In some embodiments, the number of injection sites for a single subject may be less than 1, 2, 3, 4, or 5. In some embodiments, the number of injections sites for a single subject may be 4.

The number of independent delivery treatments may be about: 1, 2, 3, 4, or 5. The number of independent delivery treatments may be more than 1, 2, 3, 4, 5, or more. The number of independent delivery treatments may be less than 1, 2, 3, 4, or 5. The time between two independent delivery treatments may be about: 1 hour, 2 hours, 6 hours, 12 hours, 24 hours, 2 days, 7 days, 14 days, 3 weeks, or 1 month. The time between two independent delivery treatments may be more than 1 hour, 2 hours, 6 hours, 12 hours, 24 hours, 2 days, 7 days, 14 days, 3 weeks, or 1 month. The time between two independent delivery treatments may be less than 1 hour, 2 hours, 6 hours, 12 hours, 24 hours, 2 days, 7 days, 14 days, 3 weeks, or 1 month. The time between independent delivery treatments can range between 1 and 24 hours. The time between independent delivery treatments can be between 2 days and 1 month. The time between independent delivery treatments can be between 1 week and 3 weeks. The time between independent delivery treatments can be between 1 week and 2 weeks. The time between independent delivery treatments can be between 2 weeks and 3 weeks.

In the methods, compositions, and kits of this disclosure, one or more injections may be given at any location in the body. One or more injections may be given in the thoracic cavity, abdominal cavity, or the like. One or more injections may be given proximal to the pancreas, for example at a site where lymphatic drainage leads to a pancreatic lymph node, for example preferentially to a pancreatic lymph node. One or more injections may be given proximal to one or more draining lymph nodes. One or more injections may be given proximal to one or more draining lymph nodes located in the abdominal cavity. The term "proximal" may scale with body size. For example, a "proximal" anatomical location in an adult human is at most 5.5 inches from a target site or organ of interest. For example, a "proximal" anatomical location in a pediatric human is at most 2.75 inches from a target site or organ of interest. One or more injections may be on the ventral side of the abdominal cavity. Injections can also be given at a location "superior" to the pancreas. "Superior" refers to the direction towards the head away from the feet. In contrast. "inferior" refers to the direction towards the feet away from the head. Injections can also be given at a location "lateral" from the pancreas (i.e. in the direction away from the midline). The midline of the body runs along the sagittal plane of the body and the pancreas it located on the left side of the body, hence injections given at a location "left and lateral" to the pancreatic lymph node are given on the subject's left side of the body. In rare cases, an individual can have a condition wherein the organs of the body are in a reversed or in mirrored position (i.e. sometimes call organ reversal, situs inversus, situs transversus or oppositus). In individuals with mirrored organs, one skilled in the art will recognize that the right and left terms used herein (e.g. "left and lateral") would need to be reversed (e.g. "right and lateral), as appropriate for the individual's mirrored organ morphology.

One or more of the administrations may be subcutaneous or intradermal. One of more of the administrations may be given superior and/or lateral to a pancreatic lymph node.

In some embodiments, one or more administrations is provided at most about 6 inches superior to the pancreas. In some embodiments, one or more administrations is provided about 4 to about 6 inches superior to a pancreas. In some embodiments, one or more administrations is provided about 4.5 to 5.5 inches superior to a pancreas. In some embodiments, one or more administrations is provided about 5 inches superior to a pancreas. In some embodiments, one or more administrations is provided about: 6, 5.75, 5.5, 5.25, 5, 4.75, 4.5, 4.25, or about 4 inches superior to a pancreas.

In some embodiments, one or more administrations is provided at most about 3 inches superior to the pancreas. In some embodiments, one or more administrations is provided about 2 to about 3 inches superior to the pancreas. In some embodiments, one or more administrations is provided about 2.25 to 2.75 inches superior to the pancreas. In some embodiments, one or more administrations is provided about 2.5 inches superior to the pancreas. In some embodiments, one or more administrations is provided about: 3, 2.875, 2.75, 2.625, 2.5, 2.375, 2.25, 2.125, or about 2 inches superior to the pancreas.

In additional embodiments, one or more administrations are provided at most about 4 inches superior to the pancreas. In additional embodiments, one or more administrations are provided at most about 2 inches to about 4 inches superior to the pancreas. In additional embodiments, one or more administrations are provided at most about 2.5 to 3.5 inches superior to the pancreas. In additional embodiments, one or more administrations are provided at most about 3 inches superior to the pancreas. In additional embodiments, one or more administrations are provided at most about: 4, 3.75, 3.5, 3.25, 3, 2.75, 2.5, 2.25, or about 2 inches superior to the pancreas.

In additional embodiments, one or more administrations are provided at most about 2 inches superior to the pancreas. In additional embodiments, one or more administrations are provided at most about 1 inch to about 2 inches superior to the pancreas. In additional embodiments, one or more administrations are provided at most about 1.25 to 1.75 inches superior to the pancreas. In additional embodiments, one or more administrations are provided at most about 1.5 inches superior to the pancreas. In additional embodiments, one or more administrations are provided at most about: 2, 1.875, 1.75, 1.625, 1.5, 1.375, 1.25, 1.125, or about 1 inch superior to a pancreatic lymph node.

In further embodiments, one or more administrations are provided about 1.5 to about 3.5 inches left and lateral to the pancreas. In further embodiments, one or more administrations are provided about 2 to about 3 inches left and lateral lateral to the pancreas. In further embodiments, one or more administrations are provided about 2.5 inches left and lateral to the pancreas. In further embodiments, one or more administrations are provided about: 1.5, 1.75, 2, 2.25, 2.5, 2.75, 3, 3.25, or about 3.5 inches left and lateral to the pancreas.

In further embodiments, one or more administrations are provided about 0.75 to about 1.75 inches left and lateral to the pancreas. In further embodiments, one or more administrations are provided about 1 to about 1.5 inches left and lateral to the pancreas. In further embodiments, one or more administrations are provided about 1.25 inches left and lateral to the pancreas. In further embodiments, one or more administrations are provided about: 0.75, 0.875, 1, 1.125, 1.25, 1.375, 1.5, 1.625, or about 1.75 inches left and lateral to the pancreas.

In yet other embodiments, one or more administrations is provided about 4.5 to about 6.5 inches left and lateral to the pancreas. In yet other embodiments, one or more administrations is provided about 5 to about 6 inches left and lateral to the pancreas. In yet other embodiments, one or more administrations is provided about 5.5 inches left and lateral to the pancreas. In yet other embodiments, one or more administrations is provided about: 4.5, 4.75, 5, 5.25, 5.5, 5.75, 6, 6.25, or about 6.5 inches left and lateral to the pancreas.

In yet other embodiments, one or more administrations is provided about 2.25 to about 3.25 inches left and lateral to the pancreas. In yet other embodiments, one or more administrations is provided about 2.5 to about 3 inches left and lateral to the pancreas. In yet other embodiments, one or more administrations is provided about 2.75 inches left and lateral to a pancreas. In yet other embodiments, one or more administrations is provided about: 2.25, 2.375, 2.5, 2.625, 2.75, 2.875, 3, 3.125, or about 3.25 inches left and lateral to the pancreas.

In some instances, the one or more administrations is to a human. In some instances, the subject is a pediatric mammal. In some instances, the subject is not a human (e.g. mouse, non-human primate). In some instances, the location of one or more administrations is scaled to body size. In some instances, the location of one or more administrations is scaled to the body size of a patient. In some instances, the location of one or more administrations is scaled to the size of the pancreas of the patient.

In some embodiments, one or more administrations is provided at most about 6 inches superior to the pancreatic lymph node, such as about 4 to about 6 inches superior to the pancreas, such as about 4.5 to about 5.5 inches superior to the pancreas, such as about 5 inches superior to the pancreas, wherein the one or more administrations is also about 1.5 to about 3.5 inches left and lateral to the pancreas, such as about 2 to about 3 inches left and lateral to the pancreas, such as about 2.5 inches left and lateral to the pancreas.

In some embodiments, one or more administrations is provided at most about 3 inches superior to the pancreatic lymph node, such as about 2 to about 3 inches superior to the pancreas, such as about 2.25 to about 2.75 inches superior to the pancreas, such as about 2.5 inches superior to the pancreas, wherein the one or more administrations is also about 0.75 to about 1.75 inches left and lateral to the pancreas, such as about 1 to about 1.5 inches left and lateral to the pancreas, such as about 1.25 inches left and lateral to the pancreas.

In additional embodiments, one or more administrations is provided at most about 6 inches superior to the pancreatic lymph node, such as about 4 to about 6 inches superior to the pancreas, such as about 4.5 to about 5.5 inches superior to the pancreas, such as about 5 inches superior to the pancreas, wherein the one or more administrations is also is provided about 4.5 to about 6.5 inches left and lateral to the pancreas, such as about 5 to about 6 inches left and lateral to the pancreas, such as about 5.5 inches left and lateral to the pancreas.

In additional embodiments, one or more administrations is provided at most about 3 inches superior to the pancreatic lymph node, such as about 2 to about 3 inches superior to the pancreas, such as about 2.25 to about 2.75 inches superior to a pancreatic lymph node, such as about 2.5 inches superior to a pancreatic lymph node, wherein the one or more administrations is also is provided about 2.25 to about 3.25 inches left and lateral to the pancreas, such as about 2.5 to about 3 inches left and lateral to the pancreas, such as about 2.75 inches left and lateral to the pancreas.

In other embodiments, one or more administrations is provided at most about 4 inches superior to the pancreas, such as about 2 inches to about 4 inches superior to the pancreas, such as about 2.5 to about 3.5 inches superior to the pancreas, such as about 3 inches superior to the pancreas, wherein the one or more administrations is about 4.5 to about 6.5 inches left and lateral to the pancreas, such as about 5 to about 6 inches left and lateral to the pancreas, such as about 5.5 inches left and lateral to a the pancreas.

In other embodiments, one or more administrations is provided at most about 2 inches superior to the pancreas, such as about 1 inch to about 2 inches superior to the pancreatic lymph node, such as about 1.25 to about 1.75 inches superior to the pancreas, such as about 1.5 inches superior to the pancreas, wherein the one or more administrations is about 2.25 to about 3.25 inches left and lateral to the pancreas, such as about 2.5 to about 3 inches left and lateral to the pancreas, such as about 2.75 inches left and lateral to the pancreas.

In other embodiments, one or more administrations is provided at most about 4 inches superior to the pancreas, such as about 2 inches to about 4 inches superior to the pancreas, such as about 2.5 to about 3.5 inches superior to the pancreas, such as about 3 inches superior to the pancreas, wherein the one or more administrations is also about 1.5 to about 3.5 inches left and lateral to the pancreas, such as about 2 to about 3 inches left and lateral to the pancreas, such as about 2.5 inches left and lateral to the pancreas.

In other embodiments, one or more administrations is provided at most about 2 inches superior to the pancreas, such as about 1 inch to about 2 inches superior to the pancreatic lymph node, such as about 1.25 to about 1.75 inches superior to the pancreas, such as about 1.5 inches superior to the pancreas, wherein the one or more administrations is also about 0.75 to about 1.75 inches left and lateral to the pancreas, such as about 1 to about 1.5 inches left and lateral to the pancreas, such as about 1.25 inches left and lateral to the pancreas.

Administrations can be used in combination. In some non-limiting examples, 1, 2, 3 or 4 administrations are provided to the subject, wherein each administration is in a different location from the other administration, in reference to the pancreas. In some non-limiting examples, the injection is subcutaneous. In additional specific non-limiting examples, the injection is subcutaneous. A diagram, showing one exemplary non-limiting administration protocol is provided in FIG. 19. In some instances, the one or more administrations is to a human. In some instances, the one or more administrations is to a pediatric patient. In some instances, the subject is not a human (e.g. mouse, non-human primate). In some instances, the location of one or more administrations is scaled to body size.

One or more injections may be given about 5.5 inches left and lateral to the pancreatic lymph node and about 3 inches superior to the pancreatic lymph node. One or more injections may be given about 2.5 inches left and lateral to the pancreatic lymph node and about 3 inches superior to the pancreatic lymph node. One or more injections may be given about 5.5 inches left and lateral to the pancreatic lymph node and about 5 inches superior to the pancreatic lymph node. One or more injections may be given about 2.5 inches left and lateral to the pancreatic lymph node and about 5 inches superior to the pancreatic lymph node.

One or more injections may be given about 2.75 inches left and lateral to the pancreatic lymph node and about 1.5 inches superior to the pancreatic lymph node. One or more injections may be given about 1.25 inches left and lateral to the pancreatic lymph node and about 1.5 inches superior to the pancreatic lymph node. One or more injections may be given about 2.75 inches left and lateral to the pancreatic lymph node and about 2.5 inches superior to the pancreatic lymph node. One or more injections may be given about 1.25 inches left and lateral to the pancreatic lymph node and about 2.5 inches superior to the pancreatic lymph node.

The location of the pancreatic lymph nodes can readily be determined by one of skill in the art. In specific non-limiting examples, imaging is used, such as computed tomography (CT) is used. In additional non-limiting examples, multidetector computed tomography (MDCT), endoscopic ultrasound (EUS), magnetic resonance imaging (MRI), radionucleotide imaging. [$^{18}$F]-fluorodeoxyglucose positron emission tomography (FDG-PET) scanning, Optical coherence tomography (OCT) can be used to determine the location of the pancreas and the pancreas. However, imaging need not be used, and an expected anatomic location of the pancreatic lymph node can be determined by anatomic landmarks on the abdomen that indicate a location where the pancreatic lymph node is typically located. In some examples, the injections are to the left of the midline, and superior to the umbilicus.

Imaging, such as computed tomography (CT) may be used to collect imaging data on the location of oligonucleotides, particles, cells, or combinations thereof injected into the body. In type 1 diabetes applications, imaging may be used to collect imaging data on whether injected oligonucleotides, particles, cells, or combinations thereof remain near the pancreas or migrate to other organs such as mesenteric lymph nodes, spleen, large intestine, liver, adipose tissue, thymus, lung, kidney, or others. Imaging may be used to collect imaging data on whether injected oligonucleotides, particles, cells or combinations thereof remain near the tissue of interest, such as the pancreas. Imaging may be used to collect imaging data on whether injected cells remain viable after injection. Imaging may be used to collect imaging data on the location of oligonucleotides, particles, cells or combinations thereof at specific times after injection. Imaging data may be used to determine the timing of subsequent injections. Imaging data may be used to determine the location of subsequent injections. Imaging data may be used to determine the composition of subsequent injections. Imaging data may be used to determine the amount of subsequent injections. Imaging data may be used to determine the efficacy of the current injection. Imaging data may be used to determine the percentage of oligonucleotides, particles, cells, or combinations thereof that accumulate in specific organs such as the pancreas. Imaging data may be used to determine the rate of accumulation or the rate of dispersion of oligonucleotides, particles, cells or combinations thereof in a given tissue.

Imaging may be collected continuously in real-time. Imaging may be one or more discrete images taken at specific times. Additional non-limiting imaging examples include, multidetector computed tomography (MDCT), endoscopic ultrasound (EUS), magnetic resonance imaging (MRI), radionucleotide imaging, [$^{18}$F]-fluorodeoxyglucose positron emission tomography (FDG-PET) scanning, or Optical coherence tomography (OCT).

One or more particles may be labeled with one or more moieties to enable image tracking. One or more particles may be labeled with a color tracking marker, a radio-active tracking marker, a pH indicator, or combinations thereof. One or more particles may be labeled with one or more fluorescent moieties. One or more particles may be labeled with a radio-active moiety. All particles may be labeled. A subset of particles may be labeled. Subsets of particles may be labeled differently. Particles may be labeled to enable recovery and analysis following injection.

One or more cells may be labeled with one or more moieties to enable image tracking. One or more cells may be labeled with a color tracking marker, a radio-active tracking marker, a viability marker, a surface marker, an antigen, or combinations thereof. One or more cells may be labeled with one or more fluorescent moieties. One or more cells may be labeled with one or more radio-active moieties. All cells may be labeled. A subset of cells may be labeled. Subsets of cells may be labeled differently. Cells may become labeled from uptake of labeled particles. Cells may be labeled to enable recovery and analysis following injection.

One or more oligonucleotides may be labeled with one or more moieties to enable image tracking. One or more oligonucleotides may be labeled with a color tracking marker, a radio-active tracking marker, or combinations thereof. One or more oligonucleotides may be labeled with one or more fluorescent moieties. One or more oligonucleotides may be labeled with one or more radio-active moieties. All oligonucleotides may be labeled. A subset of oligonucleotides may be labeled. Subsets of oligonucleotides may be labeled differently.

A suitable delivery route may be injection with a fine bore needle, which includes subcutaneous, ocular and the like. The term "fine bore needle" may mean needles of at least 20 gauge size, typically between about 22 gauge and about 30 gauge and above. In some cases, the fine bore needle may be least as fine as 24 gauge, at least as fine bore as 26 gauge, and at least as fine as 28 gauge.

Injection delivery is made during a normal injection time period. In some cases, such time periods may be about: 5, 10, 15, 20, or 25 seconds. In some cases, such time periods may be may be less than about: 5, 10, 15, 20, 25 seconds or less. In some cases, such time periods may be more than about: 5, 10, 15, 20, 25 seconds or more.

Composition of Injection

Syringable injections to subjects for treatment of conditions such as autoimmune diseases (e.g. type 1 diabetes) or inflammatory diseases (e.g. irritable bowel syndrome) may comprise cells, particles or combinations of both. In some cases, ex vivo manipulated DCs (e.g. tolerogenic DCs) may be injected. In some cases, ex vivo unmanipulated DCs may be injected. In some cases, a mixture of different types of ex vivo manipulated DCs may be injected such as a mixture of passage 1 and passage 2 cells or a mixture of frozen and fresh cells or a mixture of donor 1 and donor 2 cells or a mixture of subject and donor cells. In some cases, ex vivo manipulated DCs may be injected with other cell populations, such as supporting cell populations.

In some cases, particles may be injected alone. In some cases, particles containing oligonucleotides (e.g. antisense oligonucleotides) may be injected alone. In some cases, oligonucleotides may be injected alone. In some cases, combinations of cells, oligonucleotides, and particles may be co-injected. In some cases, small molecules, hormones, lipids, proteins such as growth factors, cytokines, chemokines or combinations thereof may be co-injected with cells, oligonucleotides, particles or combinations thereof.

In some embodiments, an effective amount increases numbers of Breg cells are produced. Methods for the isolation and quantitation of populations of B-cells are well known in the art, and the isolation and/or quantitation of regulatory B-cells can be accomplished by any means known to one of skill in the art, see for example, Published U.S. Patent Application No. 2013/36754. In some embodiments, the regulatory B-cells produce interleukin-10 and are $CD24^{HIGH}CD27^+$. In additional embodiments, the regulator B-cells express one or more of CD1 d, CD5, CD19, CD20, CD21, CD22, CD23, CD24, CD25, CD27, CD38, CD40, CD48, CD72, and CD148 and produce IL-10. In specific non-limiting examples, the regulatory B-cells are CD1 $d^{hi}CD5^+CD19^{hi}$ and produce IL-10. In some embodiments, the disclosed method increase regulatory B-cells in a subject of interest by at least about 30%, such as at least about: 30%, 40%, 50%, 60%, 70%, 80%, 90%, 100%, or 200%. In additional embodiments, the methods include measuring Breg cells in a sample from the subject.

In some cases, co-delivery of particles and ex vivo manipulated DCs may result from combining both into one injectable aliquot. In some cases, co-delivery of particles and ex vivo manipulated DCs may result from incomplete removal of non-endocytosed particles in particle-treated ex vivo DC populations. In some cases, co-delivery of particles and ex vivo manipulated DCs may result from incomplete intracellular degradation of particles in particle-treated ex vivo DCs.

In some cases, co-delivery may occur contemporaneously. In some cases, co-delivery may occur sequentially. In some cases, sequential co-delivery may span about: 1, 2, 3, 4, 5, 10, 20, 30, or 60 minutes. In some cases, sequential co-delivery may span more than about: 1, 2, 3, 4, 5, 10, 20, 30, or 60 minutes. In some cases, sequential co-delivery may span less than about: 1, 2, 3, 4, 5, 10, 20, 30, or 60 minutes.

In some cases, particles may be polymeric microspheres. In some cases, particles may be polymeric nanospheres. In some cases, particles may comprise polymeric monomers that may degrade upon exposure to aqueous solution. In some cases, particles may comprise polymeric monomers that may degrade upon exposure to acidic pH. In some cases, degradation may cause particles to release their contents (e.g. oligonucleotides).

In some cases, particles (e.g. nanospheres) may be endocytosed by ex vivo DCs, endogenous DCs, other endogenous cell types, or combinations thereof. In some cases, particles (e.g. microspheres) may not be endocytosed. In some cases, particles may be degradable. In some cases, degradable particles (e.g. microspheres) may release one or more oligonucleotides (e.g. antisense oligonucleotides) upon degradation, and such released oligonucleotides may be subsequently endocytosed by ex vivo DCs, endogenous DCs, other endogenous cell types, and combinations thereof.

Cells delivered to subjects (e.g. pediatric patients) with a condition (e.g. type 1 diabetes) may be manipulated ex vivo prior to delivery. Cells may be manipulated in a clinical setting. For example, manipulation of cells may include expanding cell number, freezing and thawing cells, aliquoting cells, contacting cells with particles, contacting cells with oligonucleotides, contacting cells with growth factors, serum, cytokines and the like, and purifying cells based on viability, endotoxin level, and/or marker expression. Cells may not be manipulated.

An acceptable level of cell viability within an injection volume may be about: 50%, 60%, 65%, 70%, 75%, 80%, 85%, 90%, 95%, 96%, 97%, 98%, or 99% of total cells within the volume. An acceptable level of cell viability within an injection volume may be more than about: 50%, 60%, 65%, 70%, 75%, 80%, 85%, 90%, 95%, 96%, 97%, 98%, 99% of total cells within the volume. An acceptable level of cell viability within an injection volume may be less than about: 50%, 60%, 65%, 70%, 75%, 80%, 85%, 90%, 95%, 96%, 97%, 98%, or 99% of total cells within the volume. In some cases, cell viability within an injection volume may be greater than about 70% of total cells within the volume. Cell viability may be unknown.

An acceptable level of endotoxin within a cellular injection volume may be about: 1, 2, 3, 4, 5, 6, 7, 8, 9, 10 EU/kg body weight. An acceptable level of endotoxin within a cellular injection volume may be less than about: 1, 2, 3, 4, 5, 6, 7, 8, 9, 10 EU/kg body weight. In some cases, endotoxin level may be less than about 5 EU/kg body weight. Endotoxin level may be unknown.

Purity of ex vivo manipulated DC populations injected into subjects may be based on marker expression. Marker expression may be confirmed by FACS analysis. In some cases, positive expression of the following markers may be used to define DC purity: CD19+, CD27+, CD38+, CD24+. In other cases, positive expression of the following markers may also be used to define DC purity: CD1B+, CD5+, CD19+, IL10+. Other marker combinations may be used to define DC purity, including for example MHCII+, CD11c+, CD80+, CD40+, CD86+. An acceptable purity of DCs injected into subjects may be about: 60%, 65%, 70%, 75%, 80%, 85%, 90%, 95%, 96%, 97%, 98%, 99% of total cells within the volume. An acceptable purity of DCs injected into subjects may be more than about: 60%, 65%, 70%, 75%, 80%, 85%, 90%, 95%, 96%, 97%, 98%, 99% of total cells within the volume. An acceptable purity of DCs injected into subjects may be less than about: 60%, 65%, 70%, 75%, 80%, 85%, 90%, 95%, 96%, 97%, 98%, or 99% of total cells within the volume. In some cases, purity of DCs injected into subjects may be greater than about 70% of total cells within the volume. Purity of DCs injected into a subject may be unknown.

In some cases, ex vivo manipulated dendritic cell populations injected into a subject may be expanded to about: 1, 2, 3, 4, 5, 6, 7, 8, 9, 10, 11, 12, 13, 14, 15, 16, 17, 18, 19, 20, 25, or 30 passage number before delivery to the subject. In some cases, ex vivo manipulated dendritic cell populations injected into a subject may be expanded to more than about: 1, 2, 3, 4, 5, 6, 7, 8, 9, 10, 11, 12, 13, 14, 15, 16, 17, 18, 19, 20, 25, 30 passage number, or more before delivery to the subject. In some cases, ex vivo manipulated dendritic cell populations injected into a subject may be expanded less than about: 1, 2, 3, 4, 5, 6, 7, 8, 9, 10, 11, 12, 13, 14, 15, 16, 17, 18, 19, 20, 25, or 30 passage number before delivery to the subject. In some cases, ex vivo dendritic cells may not be passaged. In some cases, ex vivo dendritic cells may be isolated and administered before one cell passage (e.g. in a cell culture or tissue dish). In some cases, ex vivo dendritic cells may be sorted, may be tagged with a marker, may be counted, may be contacted with a surface or another cell type, may be exposed to a stimuli, or manipulated in another manner.

In some cases, ex vivo manipulated dendritic cell populations injected into a subject may be freshly isolated. In some cases, ex vivo manipulated dendritic cell populations injected into a subject may be previously frozen. In some cases, ex vivo manipulated dendritic cell populations injected into a subject may be previous frozen for about: 1 day, 1 week, 1 month, 1 year, 2 years, or 3 years. In some cases, ex vivo manipulated dendritic cell populations injected into a subject may be previously frozen for more than about: 1 day, 1 week, 1 month, 1 year, 2 years, 3 years or more. In some cases, ex vivo manipulated dendritic cell populations injected into a subject may be previously frozen for less than about: 1 day, 1 week, 1 month, 1 year, 2 years, or 3 years.

In some cases, ex vivo manipulated dendritic cell populations are isolated from and injected back into the same recipient. In some cases, ex vivo manipulated dendritic cell populations are isolated from one individual and injected into a different individual. In some cases, ex vivo manipulated dendritic cell populations are isolated from one individual and injected into a different individual, wherein the two individuals are identically matched for alleles HLA-A, B, C and DR. In some cases, ex vivo manipulated dendritic cell populations are isolated from one individual and injected into a different individual, wherein the two individuals mismatch only one of the following alleles: HLA-A, B, C, and DR. In some cases, ex vivo manipulated dendritic cell populations are isolated from a family member (sibling, parent, grandparent, cousin, aunt, uncle). In some cases, ex vivo manipulated dendritic cell populations are isolated from an unrelated subject.

Multi-Injections

Nonfasting blood glucose levels in a subject with type 1 diabetes may be between about 180 mg/dL and about 650 mg/dL. Nonfasting blood glucose levels in a normal subject may be between about 80 mg/dL and about 120 mg/dL. In the methods and kits of this disclosure, restoring blood glucose levels to pre-diabetic levels may restore blood glucose levels to be about 80, 85, 90, 95, 100, 105, 110, 115, or 120 mg/dL. In some cases, restoring blood glucose levels to pre-diabetic levels may restore blood glucose levels to be less than about: 80, 85, 90, 95, 100, 105, 110, 115, or 120 mg/dL.

The two or more subcutaneous injections administered at one or more injection sites proximal to the pancreas, may bring blood glucose levels closer to a pre-diabetic level for about: 1 day, 7 days, 21 days, 30 days, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, or 20 months. In some embodiments, blood glucose levels may be brought closer to a pre-diabetic levels for at least about: 1 day, 7 days, 21 days, 30 days, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months or more. In some embodiments, blood glucose levels may be brought closer to a pre-diabetic levels for at most about: 1 day, 7 days, 21 days, 30 days, 1 month, 2 months, 3 months, or 4 months, 5 months, 6 months, 7 months, 8 months, 9 months, 10 months, 11 months, 12 months, 13 months, 14 months, 15 months, 16 months, 17 months, 18 months, 19 months, or 20 months. The two or more subcutaneous injections administered at one or more injection sites proximal to a pancreatic lymph node or the pancreas, may bring blood glucose levels closer to a pre-diabetic level for between about 25 to about 35 days. The two or more subcutaneous injections administered at one or more injection sites proximal to a pancreatic lymph node or the pancreas, may bring blood glucose levels closer to a pre-diabetic level for between about 28 to about 32 days. The two or more subcutaneous injections administered at one or more injection sites proximal to a pancreatic lymph node or the pancreas, may bring blood glucose levels closer to a pre-diabetic level for between about 20 to about 40 days. The two or more subcutaneous injections administered at one or more injection sites proximal to a pancreatic lymph node or the pancreas, may bring blood glucose levels closer to a pre-diabetic level for between about 65 to about 75 weeks. The two or more subcutaneous injections administered at one or more injection sites proximal to a pancreatic lymph node or the pancreas, may bring blood glucose levels closer to a pre-diabetic level for between about 68 to about 72 weeks. The two or more subcutaneous injections administered at one or more injection sites proximal to a pancreatic lymph node or the pancreas, may bring blood glucose levels closer to a pre-diabetic level for between about 60 to about 80 weeks. Four subcutaneous injections administered at 4 injection sites proximal to the pancreatic lymph node, may bring blood glucose levels closer to pre-diabetic levels for about 70 weeks or more. Bringing blood glucose levels closer to pre-diabetic levels can be restoring blood glucose levels to pre-diabetic levels.

The two or more subcutaneous injections administered at one or more injection sites proximal to a pancreatic lymph node or the pancreas, may preserve remaining pancreatic beta cell viability for about: 7 days, 21 days, 30 days, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, or 20 months. In some embodiments, remaining pancreatic beta cells may be preserved for at least about: 7 days, 21 days, 30 days, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months or more. In some embodiments, remaining pancreatic beta cells may be preserved for at most about: 7 days, 21 days, 30 days, 1 month, 2 months, 3 months, or 4 months, 5 months, 6 months, 7 months, 8 months, 9 months, 10 months, 11 months, 12 months, 13 months, 14 months, 15 months, 16 months, 17 months, 18 months, 19 months, or 20 months. The two or more subcutaneous injections administered at one or more injection sites proximal to a pancreatic lymph node or the pancreas, may preserve remaining pancreatic beta cell viability for between about 25 to about 35 days. The two or more subcutaneous injections administered at one or more injection sites proximal to a pancreatic lymph node or the pancreas, may preserve remaining pancreatic beta cell viability for between about 65 to about 75 weeks. Four subcutaneous injections administered at 4 injection sites proximal to the pancreatic lymph node, may preserve remaining pancreatic beta cell viability for about 70 weeks or more.

Altering Amounts of Cell Populations

The methods and kits of this disclosure comprise treating a subject (e.g. pediatric patient) to reverse or reduce a condition. In some cases, the condition may be an autoimmune disease. In some cases, the condition may be an inflammatory disease. An autoimmune disease may include type 1 diabetes, arthritis, asthma, septic shock, lung fibrosis, glomerulonephritis, AIDS, and the like. Inflammatory diseases may include inflammatory bowel disease (IBD). In some cases, the disease may be type 1 diabetes. Reversing or reducing type 1 diabetes may include reducing blood glucose levels to pre-diabetic levels, increasing suppressive B-cell populations, reducing T-cell populations, inducing RA production in DC populations, and the like.

In some cases, increasing suppressive B-cell populations may occur systemically throughout the subject. In some cases, increasing suppressive B-cell populations may occur within the circulating population. In some cases, increasing suppressive B-cell populations may occur selectively in one or more draining lymph nodes. In some cases, increasing suppressive B-cell populations may occur selectively in one or more pancreatic lymph nodes. In some cases, increasing suppressive B-cell population may occur relative to total B-cell populations within pancreatic lymph nodes.

In some cases, reducing T-cell populations may occur systemically throughout the subject. In some cases, reducing T-cell populations may occur within the circulating population. In some cases, reducing T-cell populations may occur selectively in one or more draining lymph nodes. In some cases, reducing T-cell populations may occur selectively in one or more pancreatic lymph nodes. In some cases, reducing T-cell populations may occur in splenic T-cell populations.

The methods and kits of this disclosure provide various methods by which a ratio of suppressive B-cells to T-cells may be altered to treat a condition such as inflammatory disease (e.g. IBD) or autoimmune disease (e.g. type 1 diabetes) in a subject. In some cases, the method may comprise in vivo delivery of ex vivo manipulated dendritic cells (e.g. tolerogenic DCs), antisense oligonucleotides, particles containing antisense oligonucleotides, co-delivery of particles containing antisense oligonucleotides with ex vivo manipulated dendritic cells (e.g. tolerogenic or immature DCs), or combinations thereof wherein said altered ratio may increase suppressive B-cells populations and decrease T-cells populations.

In some cases, an increase in suppressive B-cell populations may result in an altered ratio between suppressive B-cell and T-cell populations. In some cases, a decrease in T-cell populations may result in an altered ratio between suppressive B-cell and T-cell populations. In some cases, an increase in suppressive B-cell populations and a decrease in T-cell populations may result in an altered ratio between suppressive B-cell and T-cell populations.

In some cases, the increase in a suppressive B-cell population may result from selective proliferation of the suppressive B-cell population. In some cases, the increase in suppressive B-cell populations may result from differentiation of other B-cell populations to a suppressive B-cell type. In some cases, the increase in the suppressive B-cell population may result from pro-survival signals selective acting on the suppressive B-cell population. In some cases, the increase in the suppressive B-cell population may result from anti-apoptotic signals selectively acting on the suppressive B-cell population (e.g. Bcl-2, PI3K, CD40, and the like). In some cases, the increase in the suppressive B-cell population may result from pro-apoptotic signals in other cell populations (e.g. capases, Apaf complex, Fas ligation, and the like). In some cases, the expression of pro-survival signals on the surface of the suppressive B-cell population compared to a non-suppressive cell population may increase. In some cases, the increase in the suppressive B-cell populations may result from apoptosis in a non-suppressive B-cell population. In some cases, this apoptosis may be induced by administering at least one tolerogenic dendritic cells.

In some cases, the altered ratio may be about: 1:1, 1:2, 1:3, 1:4, 1:5, 1:6, 1:7, 1:8, 1:9, 1:10, 1:11, 1:12, 1:13, 1:14, 1:15, 1:20, or 1:25 of suppressive B-cells to T-cells. In some cases, the altered ratio may be more than about: 1:1, 1:2, 1:3, 1:4, 1:5, 1:6, 1:7, 1:8, 1:9, 1:10, 1:11, 1:12, 1:13, 1:14, 1:15, 1:20, or 1:25 of suppressive B-cells to T-cells. In some cases, the altered ratio may be less than about: 1:1, 1:2, 1:3, 1:4, 1:5, 1:6, 1:7, 1:8, 1:9, 1:10, 1:11, 1:12, 1:13, 1:14, 1:15, 1:20, or 1:25 of suppressive B-cells to T-cells.

In some cases, the decrease in T-cell populations may result from reductions in T-cell proliferation. In some cases, T-cell proliferation may be reduced by about: 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or 75%. In some cases, T-cell proliferation may be reduced by more than about: 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or 75%. In some cases, T-cell proliferation may be reduced by less than about: 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, or 75%. In some cases, T-cell proliferation may be reduced between about 50% and about 70%.

In some cases, altering the ratio of suppressive B-cells to T-cells may comprise contacting a suppressive B-cell with a T-cell. In some cases, altering the ratio of suppressive B-cells to T-cells may not comprise contacting a suppressive B-cell with a T-cell. In some cases, increasing suppressive B-cells populations may comprise contacting a suppressive B-cell with a T-cell. In some cases, decreasing T-cell populations may comprise contacting a suppressive B-cell with a T-cell.

Retinoic Acid-Mediated Treatment

Retinoic acid (RA) is a water soluble metabolite of vitamin A (retinol). RA is a molecule relevant in tolerance that may confer fitness, pro-survival, and stability to suppressive cell populations (e.g. suppressive B-cell populations). In the methods and kits of this disclosure, effective amounts of treatment resulting in increased suppressive B-cell populations may result from increases in local soluble RA production. Furthermore, in some cases, RA production in vivo may result in homing of cell populations (e.g. suppressive B-cells). Suppressive B-cells may express one or more retinoic acid receptors (RARs) and one or more retinoid X receptors (RXRs). Suppressive B-cells may express RARs at greater levels than other cell populations. Suppressive B-cells may express RXRs at greater levels than other cell populations.

Dendritic cell populations (e.g. cDCs, iDCs, tolerogenic DCs, endogenous DCs), may express rate-limiting enzymes for RA biosynthesis. Examples of such enzymes may include aldehyde dehydrogenease 1 (ALDH1) and aldehyde dehydrogenase 2 (ALDH2). Tolerogenic DCs may express greater amounts of specific enzyme isoforms compared with other cell populations. Tolerogenic DCs may express greater amounts of the 1A2 isoform compared with control dendritic populations.

Dendritic cell populations (e.g. cDCs, iDCs, tolerogenic DCs, endogenous DCs) may produce RA. In some cases, tolerogenic DCs may produce greater amounts of RA compared with other cell populations. In some cases, tolerogenic DCs may increase production of RA, after effective amounts of treatment may be delivered to a subject. In some cases, tolerogenic DCs may produce RA in specific locations, such as the pancreatic lymph node. In some cases, tolerogenic DCs may produce RA causing suppressive B-cell populations to migrate to the source of production (e.g. pancreatic lymph node).

In some cases, particles comprising RA may be delivered to dendritic cell populations (e.g. cDCs, iDCs, tolerogenic DCs, endogenous DCs). Particles comprising RA may be delivered to ex vivo DC populations, which may be subsequently delivered in vivo. Particles comprising RA may be delivered directly, via syringable injection, to various in vivo locations in a subject.

Tolerogenic DCs may have a greater amount of ALDH enzyme per cell compared with other populations (e.g. cDCs), a faster catalytic rate for RA biosynthesis compared with other populations (e.g. cDCs), or both. RA-producing DCs may be immunosuppressive. Tolerogenic DCs may be immunosuppressive. RA-producing DCs may be immunosuppressive such that an inflammatory or autoimmune disease is stopped, reversed, or diminished. Tolerogenic DCs may be immunosuppressive such that an inflammatory or autoimmune disease is stopped, reversed, or diminished. RA-producing DCs may be immunosuppressive by preventing co-stimulation of a T-cell that is within a radial distance of three cell lengths. Tolerogenic DCs may be immunosuppressive by preventing co-stimulation of a T-cell that is within a radial distance of three cell lengths. Tolerogenic DCs may be administered to the patient without immunosuppressive drugs (such as glucocorticoids, cytostatics, antibodies, or others) at the time of administering or at any later point in time. Tolerogenic DCs, microparticles, nanoparticles, or combinations thereof may be administered to the patient without immunosuppressive therapy at the time of administering or at any later point in time. RA-producing DCs may be therapeutic in inflammatory diseases and autoimmune diseases, by causing suppressive B-cell populations to increase in local areas of inflammation (e.g. pancreatic lymph nodes).

Kits

In some cases, this disclosure provides a kit comprising a plurality of particles (e.g. microspheres) and one or more entities (e.g. oligonucleotides, proteins, biomolecules), and instructions for attaching or encapsulating the one or more entities (e.g. oligonucleotides, proteins, biomolecules) onto or within the particles (e.g. microspheres). Also included may be instructions for contacting said particles (e.g. microspheres) with any suitable cell population. As specified throughout this disclosure, any suitable entity may be attached to or encapsulated within the particles (e.g. microspheres). As described through this disclosure, a particle may be formed from PEG and PVP polymers. In this case, the kit may or may not include PEG and PVP polymers.

In some cases, this disclosure provides a kit comprising a plurality of particles (e.g. nanospheres) and one or more entities (e.g. oligonucleotides, proteins, biomolecules), and instructions for attaching or encapsulating the one or more entities (e.g. oligonucleotides, proteins, biomolecules) onto or within the particles (e.g. nanospheres). Also include may be instructions for contacting said particles (e.g. nanospheres) with any suitable cell population. As specified throughout this disclosure, any suitable entity may be attached to or encapsulated within the particles (e.g. nanospheres). As described through this disclosure, a particle may be formed from PEG and PVP polymers. In this case, the kit may or may not include PEG and PVP polymers.

In some instances, a kit may comprise oligonucleotides for injection. Oligonucleotides may have any of the features described herewith. Oligonucleotides may be approved by FDA for use in human patients. Oligonucleotides may be approved by FDA for use in pediatric human patients. Oligonucleotides may be approved by FDA for preventing, treating, or reversing type 1 diabetes in a human patient. Oligonucleotides may be approved by FDA for injection proximal to the pancreas. The kit may include instructions for contacting one or more oligonucleotides with a suitable ex vivo cell population prior to injection. The kit may include instructions for creating a solution of oligonucleotides in a buffering liquid prior to injection. The kit may include instructions for the anatomical site to inject one or more oligonucleotides. The kit may include one or more injectable syringes as described herewith. The kit may include an amount of buffering liquid to create a oligonucleotide solution. The kit may not need to be refrigerated. The kit may be unrefrigerated for up to 24 hours. The kit may be used in a clinical setting. The kit may be used in a laboratory setting. In some instances, the oligonucleotides, buffering liquid, and syringe are sterile. In some instances, the oligonucleotides contain less than 5 EU/kg body weight of endotoxin.

In some instances, a kit may comprise particles for injection. Particles may have any of the features described herewith. Particles may comprise oligonucleotides. Particles may be approved by FDA for use in human patients. Particles may be approved by FDA for use in pediatric human patients. Particles may be approved by FDA for preventing, treating, or reversing type 1 diabetes in a human patient. Particles may be approved by FDA for injection proximal to the pancreas. The kit may include instructions for contacting one or more particles with a suitable ex vivo cell population prior to injection. The kit may include instructions for creating a particle suspension with a buffering liquid prior to injection. The kit may include instructions for the anatomical site to inject one or more particles. The kit may include one or more injectable syringes as described herewith. The kit may include an amount of buffering liquid to create a particle suspension. The kit may not need to be refrigerated. The kit may be unrefrigerated for up to 24 hours. The kit may be used in a clinical setting. The kit may be used in a laboratory setting. In some instances, the particles, buffering liquid, and syringe are sterile. In some instances, the particles contain less than 5 EU/kg body weight of endotoxin.

In some instances, a kit may comprise components for preparing ex vivo tolerogenic DCs for injection into a patient. The kit may comprise particles described herewith. The kit may comprise oligonucleotides described herewith. The kit may comprise one or more cytokines (e.g. GM-CSF, TGF-β, IL-4). The kit may comprise markers described herewith to label cells, oligonucleotides, particles, or combinations thereof. The markers may be fluorescent. One or more markers may be a cell surface marker. One or more markers may be a viability indicator. The kit may comprise a component for sorting cells based on the one or more markers attached (e.g. magnetic sorting column). The kit may comprise a component for sorting free particles from cells (e.g. size exclusion column). The ex vivo manipulated cells produced using the kit may be approved by FDA for use in human patients. The ex vivo manipulated cells produced using the kit may be approved by FDA for use in pediatric human patients. The ex vivo manipulated cells produced using the kit may be approved by FDA for preventing, treating, or reversing type 1 diabetes in a human patient. The ex vivo manipulated cells produced using the kit may be approved by FDA for injection proximal to the pancreas. The kit may include instructions for contacting one or more particles with a suitable ex vivo cell population prior to injection. The kit may include instructions for creating a cellular or cellular and particle suspension with a buffering liquid prior to injection. The kit may include instructions for the anatomical site to inject. The kit may include one or more injectable syringes as described herewith. The kit may include an amount of buffering liquid to create a cellular or cellular and particle suspension. The kit may not need to be refrigerated. The kit may be unrefrigerated for up to 24 hours. The kit may be used in a clinical setting. The kit may be used in a laboratory setting. In some instances, the cells, particles, buffering liquid, and syringe are sterile. In some instances, the cells contain less than 5 EU/kg body weight of endotoxin.

CLAUSES

In some aspects, provided herein, are methods for restoration of blood glucose to a pre-diabetic level in a pediatric mammal comprising: administering two or more subcutaneous injections of tolerogenic dendritic cells at one or more injection sites proximal to a pancreatic lymph node in a mammal, wherein said blood glucose may be restored to said pre-diabetic level for a period of at least twenty four hours. In some embodiments, said tolerogenic dendritic cells may be isolated from said mammal or from a different mammal. In some embodiments, said tolerogenic dendritic cells may be previously frozen.

This disclosure provides methods, compositions, and kits for treating a mammal with a disease. The methods, compositions, and kits are particularly useful for treating a mammal that has or is likely to have onset of diabetes.

In some embodiments, one of said one or more injection sites may be about 3.5 to about 2.25 inches lateral to said pancreatic lymph node and about 2 to about 1 inches superior to said pancreatic lymph node. In some embodiments, one of said one or more injection sites may be about 1.75 to about 0.75 inches lateral to said pancreatic lymph node and about 2 to about 1 inches superior to said pancreatic lymph node. In some embodiments, one of said one or more injection sites may be about 3.25 to about 2.25 inches lateral to said pancreatic lymph node and about 3 to about 2 inches superior to said pancreatic lymph node. In some embodiments, one of said one or more injection sites may be about 1.75 to about 0.75 inches lateral to said pancreatic lymph node and about 3 to about 2 inches superior to said pancreatic lymph node. In some embodiments, said administering may comprise at least four injection sites. In some embodiments, said first injection site may be about 3.25 to about 2.25 inches lateral to said pancreatic lymph node and about 2 to about 1 inches superior to said pancreatic lymph node, wherein said second injection site may be about 1.75 to about 0.75 inches lateral to said pancreatic lymph node and about 2 to about 1 inches superior to said pancreatic lymph node, wherein said third injection site may be about 3.25 to about 2.25 inches lateral to said pancreatic lymph node and about 3 to about 2 inches superior to said pancreatic lymph node, and wherein said fourth injection site may be about 1.75 to about 0.75 inches lateral to said pancreatic lymph node and about 3 to about 2 inches superior to said pancreatic lymph node.

Some embodiments may further comprise administering at least three, four or five of said subcutaneous injections of tolerogenic dendritic cells. In some embodiments, said blood glucose may be restored to said pre-diabetic level for between about 25 to about 35 days. In some embodiments, said blood glucose may be restored to said pre-diabetic level for between about 65 to about 75 weeks.

In some embodiments, said mammal may be a human, a mouse, or a non-human primate.

In some embodiments, said administering may not comprise immunosuppressive therapies. In some embodiments, said administering may prevent co-stimulation of a T-cell that is within a radial distance of three cell lengths to said injection site. In some embodiments, said tolerogenic dendritic cells may be labeled with at least one marker. In some embodiments, said marker may be a fluorescent marker. In some embodiments, said fluorescent marker may be a viability indicator. In some embodiments, not all of said tolerogenic dendritic cells may be labeled with a marker.

In some embodiments, said two or more subcutaneous injections of tolerogenic dendritic cells may comprise at least one particle, wherein said particle may comprise oligonucleotides including the nucleic acid sequence set forth as SEQ ID NOs: 4, 5, 6, or 7, or combinations thereof. In some embodiments, said particle may labeled with at least one marker. In some embodiments, not all of said particles may be labeled with a marker. In some embodiments, said marker may be a fluorescent marker. In some embodiments, said fluorescent marker may be a pH indicator.

Some embodiments may further comprise tracking said marker after administering. Some embodiments may further comprise quantifying accumulation of one or more markers at pre-determined anatomical locations.

In some embodiments, said mammal may have clinical onset of type 1 diabetes for at least 1 month. In some embodiments, said mammal may have clinical onset of type 1 diabetes for at least 1 year. In some embodiments, said mammal may have clinical onset of type 1 diabetes for at least 5 years. In some embodiments, said mammal may be a human. In some embodiments, said mammal may be a mouse or a non-human primate. In some embodiments, said human may be between about 1 to about 5 years of age, between about 6 to about 10 years of age, or between about 11 to about 18 years of age. In some embodiments, said human may have pediatric onset of diabetes.

In some aspects, provided herein, are methods for treating type 1 diabetes in said pediatric mammal comprising: expanding a suppressive B-cell population in a mammal, wherein a greater expansion of said suppressive B-cell population may occur near said pancreatic lymph node compared to a systemic suppressive B-cell population. In some embodiments, no additional immunosuppressive therapies may be administered. In some embodiments, said pediatric mammal may be a human. In some embodiments, said pediatric mammal may be a mouse or a non-human primate. In some embodiments, said human may be between about 1 to about 5 years of age, between about 6 to about 10 years or age, or between about 11 to about 18 years of age.

In some embodiments, said pediatric mammal may have clinical onset of type 1 diabetes for at most 1 month. In some embodiments, said pediatric mammal may have clinical onset of type 1 diabetes for at most 1 year. In some embodiments, said pediatric mammal may have clinical onset of type 1 diabetes for at most 5 years.

In some embodiments, said suppressive B-cell population may express the following markers: CD19, IgD, IgM, CD10, CD21, CD27, CD38, IL-10, and/or CD40. In some embodiments, said suppressive B-cell population may express the following markers: CD19, CD27, CD38, and CD24. In some embodiments, said suppressive B-cell population may express the following markers: CD1B, CD5, CD19, and IL10. In some embodiments, said suppressive B-cell population may not express a CD11c marker. In some embodiments, said suppressive B-cell population may comprise a memory B-cell population. In some embodiments, said memory B-cell population may express the following markers: CD27, CD38, and CD40. In some embodiments, said suppressive B-cell population may proliferate. In some embodiments, said suppressive B-cell population may differentiate. Some embodiments may further comprise suppressing proliferation of a T-cell population. Some embodiments may further comprise contacting a suppressive B-cell from said suppressive B-cell population with a T-cell from said T-cell population.

In some embodiments, said suppressive B-cell population may be induced by administering two or more subcutaneous injections comprising tolerogenic dendritic cells, nanoparticles, microparticles, or combinations thereof. In some embodiments, said two or more subcutaneous injections may be administered at one or more injection sites proximal to said pancreatic lymph node. In some embodiments, said two or more subcutaneous injections may comprise four injection sites. In some embodiments, said nanoparticles may comprise oligonucleotides. In some embodiments, said microparticles may comprise oligonucleotides.

Some embodiments may further comprise conferring increased survival to said suppressive B-cell population by administering at least one tolerogenic dendritic cell. Some embodiments may further comprise increasing expression of pro-survival signals on the surface of said suppressive B-cell population compared to a non-suppressive cell population. Some embodiments may further comprise inducing apoptosis in a non-suppressive B-cell population by administering at least one tolerogenic dendritic cell.

In some aspects, provided herein, are methods for altering a ratio of suppressive B-cells to T-cells to treat type 1 diabetes in a mammal comprising: delivering tolerogenic dendritic cells to the mammal, wherein said altering may comprise increasing said suppressive B-cells and decreasing said T-cells. Some embodiments may further comprise injecting said tolerogenic dendritic cells at a site proximal to a pancreatic lymph node or the pancreas in said mammal. Some embodiments may further comprise expanding said suppressive B-cells. Some embodiments may further comprise suppressing proliferation of said T-cells. In some embodiments, said suppressive B-cells may express the following markers: B220, CD19, and IL10. In some embodiments, said suppressive B-cells may not express a CD11c marker. In some embodiments, said ratio of suppressive B-cells to T-cells may be about 1:10. In some embodiments, said ratio may be altered by reducing said proliferation of said T-cells by between about 40% to about 55%, such as about 50%. In some embodiments, said ratio of suppressive B-cells to T-cells may be about 1:1. In some embodiments, said ratio may be altered by reducing said proliferation of said T-cells by between about 65% to about 80%, such as about 67%. Some embodiments may further comprise contacting at least one of said suppressive B-cells with at least one of said T-cells.

In some aspects, provided herein, are methods for reducing an inflammatory response in a mammal comprising: producing bioactive retinoic acid in a mammal, wherein said bioactive retinoic acid may be produced by introducing tolerogenic dendritic cells in or near a pancreatic lymph node or the pancreas of said mammal, and wherein said bioactive retinoic acid may cause an increase in a suppressive B-cell population expressing at least one retinoic acid receptor (RAR) and at least one retinoid X receptor (RXR). In some embodiments, said mammal may be a human. In some embodiments, said mammal may be a mouse or a non-human primate. In some embodiments, said human may be an adolescent, a child, or a human less than 18 years of age. In some embodiments, said mammal may have irritable bowel disease (IBD). In some embodiments, said mammal may have type 1 diabetes (T1D).

In some aspects, provided herein, are methods for restoration of blood glucose to a pre-diabetic level in a pediatric mammal comprising: administering two or more subcutaneous injections of tolerogenic dendritic cells at one or more injection sites proximal to a pancreas in said pediatric mammal, wherein said blood glucose may be restored to said pre-diabetic level for a period of at least twenty four hours. In some embodiments, said tolerogenic dendritic cells may be isolated from said pediatric mammal or from a different mammal of the same species. In some embodiments, said tolerogenic dendritic cells may have been previously frozen.

In some embodiments, said one or more injection sites may be about 3.25 to about 2.25 inches left and lateral to said pancreas and about 2 to about 1 inches superior to said pancreas. In some embodiments, one of said one or more injection sites may be about 1.75 to about 0.75 inches left and lateral to said pancreas and about 2 to about 1 inches superior to said pancreas. In some embodiments, one of said one or more injection sites may be about 3.25 to about 2.25 inches left and lateral to said pancreas and about 3 to about 2 inches superior to said pancreas. In some embodiments, one of said one or more injection sites may be about 1.75 to about 0.75 inches left and lateral to said pancreas and about 3 to about 2 inches superior to said pancreas. In some embodiments, said administering may comprise at least four injection sites. In some embodiments, said first injection site may be about 3.25 to about 2.25 inches left and lateral to said pancreas and about 2 to about 1 inches superior to said pancreas, wherein said second injection site may be about 1.75 to about 0.75 inches left and lateral to said pancreas and about 2 to about 1 inches superior to said pancreas, wherein said third injection site may be about 3.25 to about 2.25 inches left and lateral to said pancreas and about 3 to about 2 inches superior to said pancreas, and wherein said fourth injection site may be about 1.75 to about 0.75 inches left and lateral to said pancreas and about 3 to about 2 inches superior to said pancreas.

Some embodiments may further comprise administering at least three, four or five of said subcutaneous injections of tolerogenic dendritic cells. In some embodiments, said blood glucose may be restored to said pre-diabetic level for between about 25 to about 35 days. In some embodiments, said blood glucose may be restored to said pre-diabetic level for between about 65 to about 75 weeks.

In some embodiments, said pediatric mammal may be a human. In some embodiments, said administering may not comprise administering additional immunosuppressive therapies. In some embodiments, said administering may prevent co-stimulation of a T-cell that is within a radial distance of three cell lengths to said injection site. In some embodiments, said tolerogenic dendritic cells may be labeled with at least one marker. In some embodiments, said marker may be a fluorescent marker. In some embodiments, said fluorescent marker may be a viability indicator. In some embodiments, not all of said tolerogenic dendritic cells may be labeled with a marker.

In some embodiments, said two or more subcutaneous injections of tolerogenic dendritic cells may comprise at least one particle, wherein said particle may comprise oligonucleotides comprising the nucleic acid sequence set forth as SEQ ID NO: 4, SEQ ID NO: 5, SEQ ID NO: 6, or SEQ ID NO: 7, or combinations thereof. In some embodiments, said particle may be labeled with at least one marker. In some embodiments, not all of said particles may be labeled with a marker. In some embodiments, said marker may be a fluorescent marker. In some embodiments, said fluorescent marker may be a pH indicator.

Some embodiments may further comprise tracker said marker after administering said tolerogenic dendritic cells. Some embodiments may further comprise quantifying accumulation of said at least one marker at pre-determined anatomical locations.

In some embodiments, said pediatric mammal may have clinical onset of type 1 diabetes for at most 1 month. In some embodiments, said pediatric mammal may have clinical onset of type 1 diabetes for at most 1 year. In some embodiments, said pediatric mammal may have clinical onset of type 1 diabetes for at most 5 years. In some embodiments, said pediatric mammal may be a human. In some embodiments, said pediatric mammal may be a mouse or a non-human primate. In some embodiments, said human may be between about 1 to about 5 years of age, between about 6 to about 10 years of age, or between about 11 to about 18 years of age. In some embodiments, said human may have pediatric onset of diabetes.

Some embodiments may further comprise: expanding a suppressive B-cell population in said pediatric mammal, wherein a greater local expansion of suppressive B-cells may occur near said pancreas as compared to a systemic suppressive B-cell expansion. In some embodiments, no additional immunosuppressive therapies may be administered. In some embodiments, said pediatric mammal may be a human. In some embodiments, said pediatric mammal may be a mouse or a non-human primate. In some embodiments, said human may be between about 1 to about 5 years of age, between about 6 to about 10 years of age, or between about 11 to about 18 years of age.

In some embodiments, said pediatric mammal may have clinical onset of type 1 diabetes for at most 1 month. In some embodiments, said pediatric mammal may have clinical onset of type 1 diabetes for at most 1 year. In some embodiments, said pediatric mammal may have clinical onset of type 1 diabetes for at most 5 years.

In some embodiments, said suppressive B-cell population may express the following markers: CD19, IgD, IgM, CD10, CD21, CD27, CD38, IL-10, and CD40. In some embodiments, said suppressive B-cell population may express the following markers: CD19, CD27, CD38, and CD24. In some embodiments, said suppressive B-cell population may express the following markers: CD1B, CD5, CD19, and IL10. In some embodiments, said suppressive B-cell population may not express a CD11c marker. In some embodiments, said suppressive B-cell population may comprise a memory B-cell population. In some embodiments, said memory B-cell population may express the following markers: CD27, CD38, and CD40. In some embodiments, said suppressive B-cell population may proliferate. In some embodiments, said suppressive B-cell population may differentiate. Some embodiments may further comprise suppressing proliferation of a T-cell population. Some embodiments may further comprise contacting a suppressive B-cell from said suppressive B-cell population with a T-cell from said T-cell population.

In some embodiments, said suppressive B-cell population may be induced by administering two or more subcutaneous injections comprising tolerogenic dendritic cells, nanoparticles, microparticles, or combinations thereof. In some embodiments, said two or more subcutaneous injections may be administered at one or more injection sites proximal to said pancreas. In some embodiments, said two or more subcutaneous injections may comprise four injection sites. In some embodiments, said nanoparticles may comprise oligonucleotides. In some embodiments, said microparticles may comprise oligonucleotides. Some embodiments may further comprise conferring increased survival to said suppressive B-cell population by administering at least one tolerogenic dendritic cell. Some embodiments may further comprise increasing expression of pro-survival signals on the surface of said suppressive B-cell population compared to a non-suppressive cell population. Some embodiments may further comprise inducing apoptosis in a non-suppressive B-cell population by administering at least one tolerogenic dendritic cell.

In some aspects, provided herein, are methods for altering a ratio of suppressive B-cells to T-cells to treat type 1 diabetes in a pediatric mammal comprising: injecting tolerogenic dendritic cells at a site proximal to a pancreas in said pediatric mammal, wherein said altering may comprise increasing said suppressive B-cells and decreasing said T-cells. Some embodiments may further comprise expanding said suppressive B-cells. Some embodiments may further comprise suppressing proliferation of said T-cells. In some embodiments, said suppressive B-cells may express the following markers: B220, CD19, and IL10. In some embodiments, said suppressive B-cells may not express a CD11c marker. In some embodiments, said ratio of suppressive B-cells to T-cells may be about 1:10. In some embodiments, said ratio may be altered by reducing said proliferation of said T-cells by between about 40% to about 55%. In some embodiments, said ratio may be altered by reducing said proliferation of said T-cells by between about 65% to about 80%. In some embodiments, said ratio of suppressive B-cells to T-cells may be about 1:1. Some embodiments may further comprise contacting at least one of said suppressive B-cells with at least one of said T-cells.

In some aspects, provided herein, are methods for reducing an inflammatory response in a mammal comprising: introducing tolerogenic dendritic cells in or near a pancreas of said mammal thereby producing retinoic acid in said mammal, wherein production of said retinoic acid may result in an increase in a suppressive B-cell population expressing at least one retinoic acid receptor and at least one retinoid X receptor. In some embodiments, said mammal may be a human. In some embodiments, said mammal may be a mouse or a non-human primate. In some embodiments, said human may be between about 1 to about 5 years of age, between about 6 to about 19 years of age, or between about 11 to about 18 years of age. In some embodiments, said mammal may have irritable bowel disease (IBD). In some embodiments, said mammal may have type 1 diabetes (T1D).

EXAMPLES

Example 1

Microspheres Loaded with Antisense Oligonucleotides

The AS-oligonucleotide sequences targeted to the CD40, CD80, and CD86 transcripts used in this Example are, with asterisks indicating sites of thioation in the backbone:

```
SEQ ID NO: 8:
CD40-AS: 5' C*AC* AG*C C*GA* GG*C* AA*A

GA*C* AC*C A*T*G C*AG* GG*C* A -3'

SEQ ID NO: 9:
CD80-AS: 5' -G*GG* AA*A G*CC* AG*G A*AT*

CT*A G*AG* CC*A A*TG G*A -3'

SEQ ID NO: 10:
CD86-AS: 5' -T*GG* GT*G C*TT* CC*G T*AA*

GT*T C*TG* GA*A C*AC* G*T*C -3'
```

An aqueous solution of the oligonucleotide mixture was prepared by combining aliquots of three oligonucleotide solutions, each of which contains one type of oligonucleotide, to form a 10 mg/ml solution of the three types of oligonucleotides. A 10 mg/ml solution of poly-L-lysine.HBr in deionized water (poly-L-lysine.HBr up to 70,000 Daltons) was prepared. The poly-L-lysine.HBr was added to the oligonucleotides solution at a volumetric ratio of 1:1. The mixture was vortexed gently. A 25% polymer solution containing 12.5% PVP (polyvinyl pyrrolidone, 40,000 Daltons) and 12.5% PEG (polyethylene glycol, 3, 350 Daltons) in 1M sodium acetate at pH5.5 was added in a 2:1 50 volumetric ratio as follows: 0.75 ml of AS-oligonucleotides, 0.75 ml of poly-L-lysine.HBr, 3.0 ml of PEG/PVP, and a total volume of 4.50 ml.

The batch was incubated for 30 minutes at 70° C. and then cooled to 23° C. Upon cooling, the solution became turbid and microspheres were formed. The suspension was then centrifuged, and the excess PEG/PVP was removed. The resulting pellet was washed by resuspending the pellet in deionized water, followed by centrifugation and removal of the supernatant. The washing process was repeated three times. The aqueous suspension was frozen and lyophilized to form a dry powder of microspheres comprising oligonucleotide and poly-L-lysine.

Figure 1A:
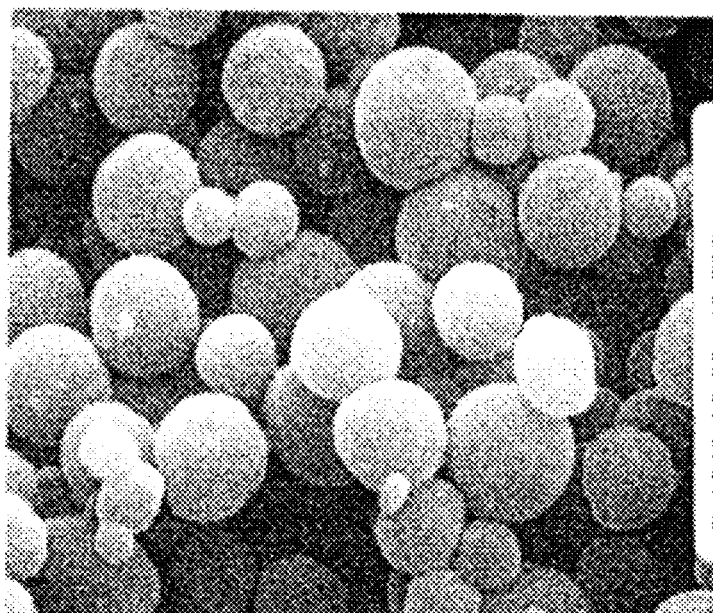
Figure 2A:
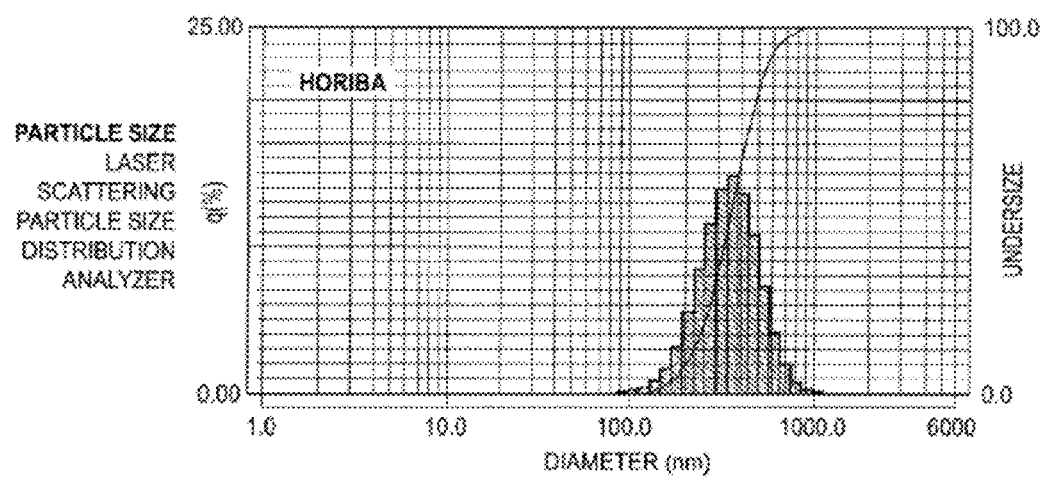
FIG. 2A is a graph summarizing the size distribution of a preparation of microspheres.
Figure 2B:
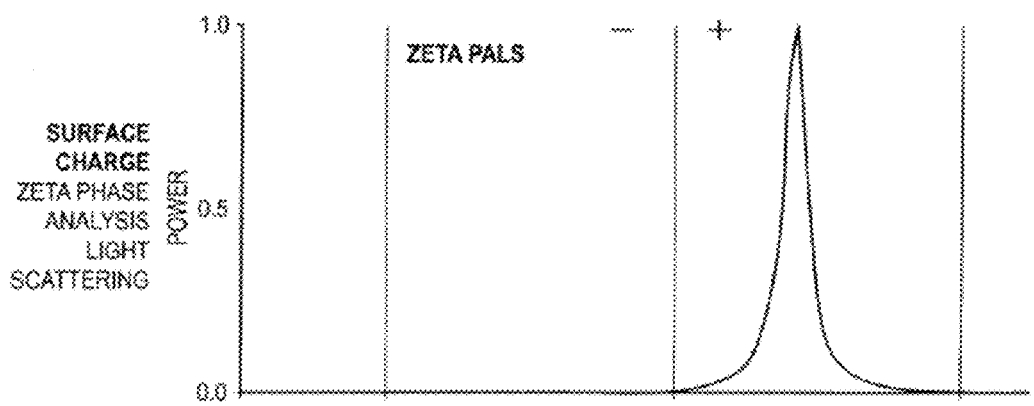
FIG. 2B is a graph summarizing the surface charge of a preparation of microspheres.
Figure 3:
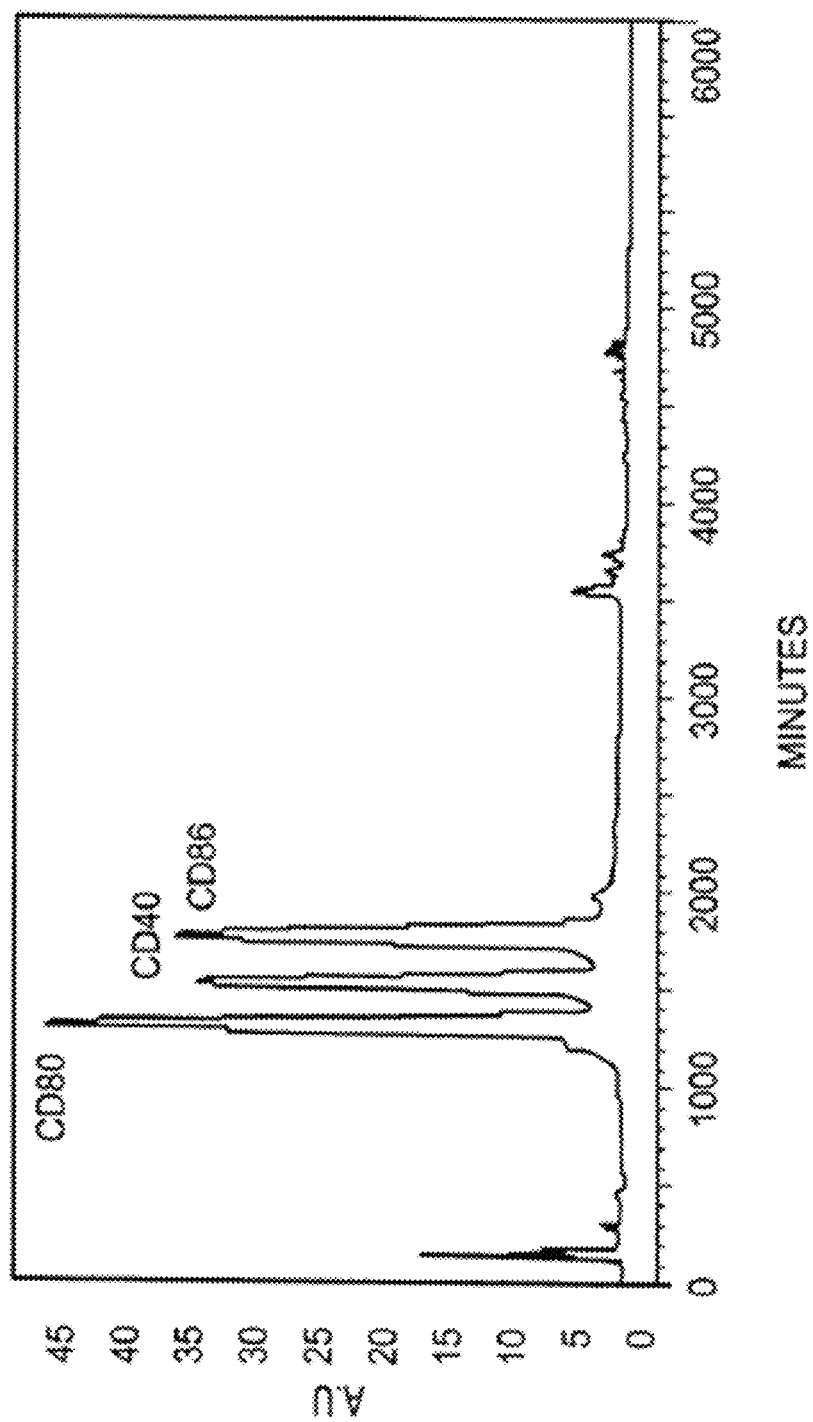
FIG. 3 is a RP-HPLC chromatogram of the oligonucleotides after deformulation of microspheres.

FIGS. 1A and 1B present representative scanning electron micrographs (SEM) of 1:1 poly-L-lysine:oligonucleotide ratio microspheres at two different magnifications. Microspheres, 0.5-4 microns in size, with an average particle size of approximately 2.5 microns were fabricated. FIG. 2A shows the size distribution of one preparation of microspheres made according to the disclosure as revealed by laser light scattering. FIG. 2B shows the determination of the surface charge of a microsphere preparation (Zeta potential) by light scattering. FIG. 3 shows a reverse phase (RP) HPLC method used to quantitate the loading and assess the integrity of the antisense oligonucleotide components of the microspheres after deformulation. Microspheres were formulated using CD86, CD40, CD80 oligonucleotides and poly-L-lysine (PLL; MW 30-70 kD). The microspheres were then deformulated using competitive displacement of the DNA oligonucleotides from the PLL by poly-L-aspartic acid (PAA). PAA was selected as a polyamino acid reagent that does not absorb at 260 nm and does not interfere with quantification of oligonucleotides at 260 nm. In RP-HPLC profiles such as FIG. 3, the area under each peak was proportional to amount of each oligonucleotide loaded into the microsphere. As shown in FIG. 3, the peak heights indicated approximately equal loading of each oligonucleotide into microspheres. The loading of oligonucleotides into micro spheres was calculated to be from about 65% to about 80% by weight. FIG. 3 also showed that the integrity of the oligonucleotides was not affected by the microsphere formulation process, as indicated by the narrow distribution of the peaks after deformulation.

Example 2

Microspheres Coated with Antisense Oligonucleotides

Carboxylate polystyrene microspheres coated with peptide $O_{10}H_6$. The microspheres have an average diameter of 0.1 µm with less than 10% variance.

Three microliters of carboxylate polystyrene microspheres, having an average diameter of 0.1 µm with less than 10% variance, were first coated with 200 µg of peptide $O_{10}H_6$ by gentle shaking for 2 hours at room temperature in 300 µL of ddH$_2$O (2.5% w/v of microspheres to ddH$_2$O; $4.55 \times 10^{13}$ particles ml$^{-1}$). The resulting positively charged particles were then equilibrated with antisense oligonucleotides (18.7 ng total weight) for 30 minutes at room temperature. Unbound antisense oligonucleotides and $O_{10}H_6$ peptides were removed by membrane filtration with a Nanosep device with a 10K molecule weight cutoff and subsequently centrifuged at 500 g for 5 minutes at room temperature. Antisense oligonucleotide-coated microspheres were recovered following centrifugation and added to $3.0 \times 10^6$ ex vivo dendritic cells, isolated from mouse splenic populations, in 1.5 mL OptiMEM media, resulting in a final antisense oligonucleotide concentration of 1.55 nM for dendritic cell uptake.

Figure 4A:
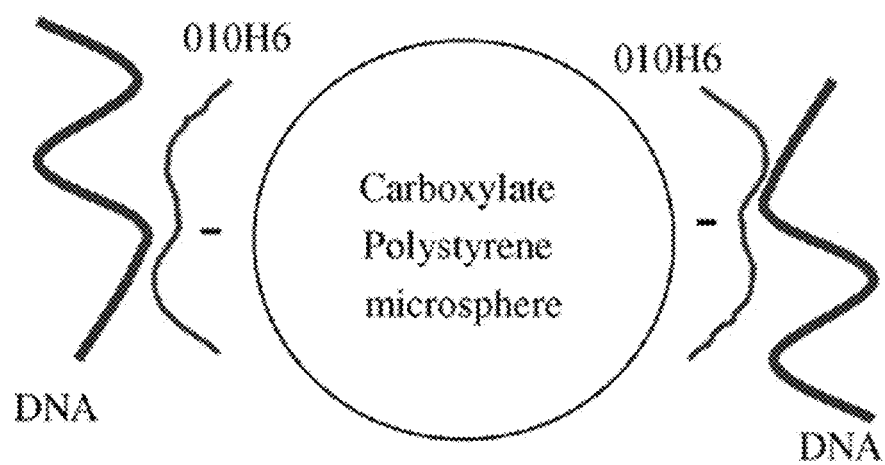
FIG. 4A is a schematic diagram of the self assembly system of microspheres coated with antisense oligonucleotides.
Figure 4B:
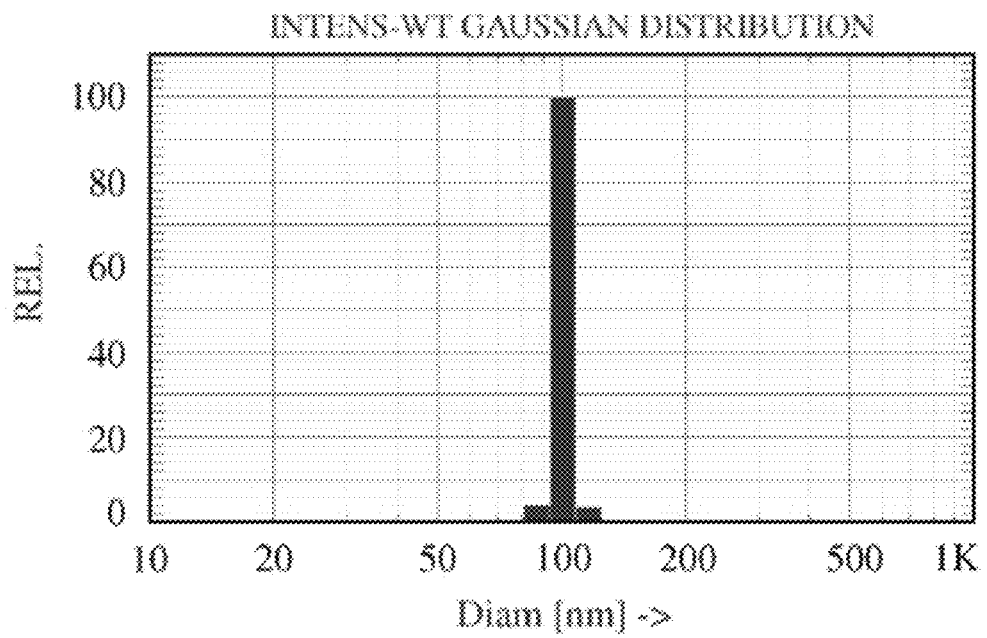
FIG. 4B is a graph summarizing the average particle size distribution of uncoated microspheres.
Figure 4C:
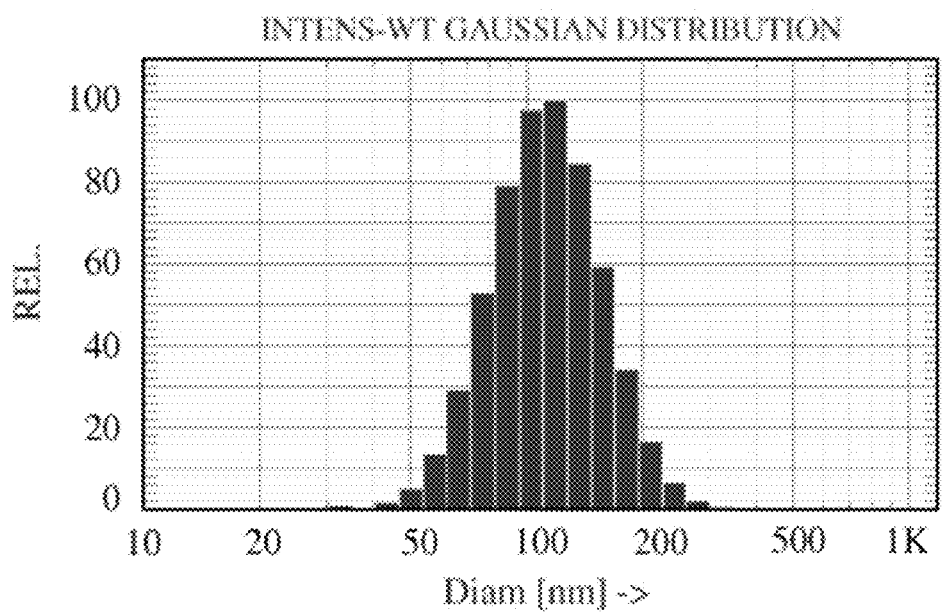
FIG. 4C is a graph summarizing the average particle size distribution of antisense oligonucleotide coated microspheres.

A schematic diagram depicts the self assembly system of carboxylate polystyrene microspheres coated with $O_{10}H_6$ and antisense oligonucleotides, FIG. 4A. Uncoated microspheres, FIG. 4B, and microspheres coated with $O_{10}H_6$ and antisense oligonucleotides, FIG. 4C, were analyzed for average microsphere size using a Nicomp 380 ZLS instrument. Coated microsphere samples contained $1.37 \times 10^{11}$ microspheres, 200 g of $O_{10}H_6$, and 18.7 ng of antisense oligonucleotides in 300 µl of ddH$_2$O. Average particle size of antisense oligonucleotide coated microspheres was determined to be 118 nm with a standard deviation of 38.7.

Example 3

Making Ex Vivo Tolerogenic DCs with Antisense Oligonucleotides

Sense oligonucleotide sequence with NF-KB binding sites:

SEQ ID NO: 11:
5' AGGGACTTTCCGCTGGGGACTTTCC 3'

Antisense oligonucleotide sequence with NF-KB binding sites:

SEQ ID NO: 12:
5' GGAAAGTCCCCAGCGGAAAGTCCCT 3'

As a control for non-specific sequence effects as well as aptameric effects that might have been induced by the GGGG quartet in the specific decoy, a double-stranded oligonucleotide consisting of a random sequence was used and designated ODN1 herein.

Sense oligonucleotide sequence for ODN1:

SEQ ID NO: 13:
5' ACCAGTCCCTAGCTACCAGTCCCTA 3'

Antisense oligonucleotide sequence for ODN1:

SEQ ID NO: 14:
5' TAGGGACTGGTAGCTAGGGACTGGT 5'

In addition, a control sequence designated ODN2 herein containing an incomplete NF-KB consensus sequence was used.

Sense oligonucleotide sequence for ODN2 with incomplete NF-KB sites:

SEQ ID NO: 15:
5' AGGTACTGTCCGCGTTAGACGTGCC 3'

Antisense oligonucleotide sequence for ODN2 with incomplete NF-KB sites:

SEQ ID NO: 16:
5' GGCACGTCTAACGCGGACAGTACCT 3'

Sense and antisense strands of each oligonucleotide were mixed in the presence of 150 mM NaCl, heated to 100° C. and allowed to cool to room temperature to obtain double-stranded DNA. FITC-conjugated double-stranded decoys were prepared in a similar fashion.

Male C57BL/10J (B10; H2b; Iab) and C3H/HeJ (C3H; H2k; Iak; Iek) mice and Female NOD mice were maintained in a specific pathogen-free facility. Animals were fed standard chow ad libitum and used at 8-12 weeks of age.

Bone marrow (BM) cells were harvested from femurs of normal B10 or NOD mice and cultured in 24 well plates ($2\times10^6$ per well) in 2 ml of RPMI-1640 media supplemented with antibiotics and 10% fetal calf serum (FCS). 4 ng/ml recombinant mouse granulocyte-macrophage colony-stimulating factor (GM-CSF) was added to propagate immature DCs. In addition to GM-CSF, 1000 units/ml recombinant IL-4 was added at the initiation of culture of the DCs. Cytokine-enriched medium was refreshed every 2 days; after gentle swirling of the plates, half of the old medium was aspirated and an equivalent volume of fresh, cytokine-supplemented medium was added as well as IL-4. Thus, nonadherent granulocytes were depleted without dislodging clusters of developing DCs attached loosely to a monolayer of plastic adherent-macrophages. Nonadherent cells release spontaneously from the clusters and were harvested after 5-7 days.

Figure 5:
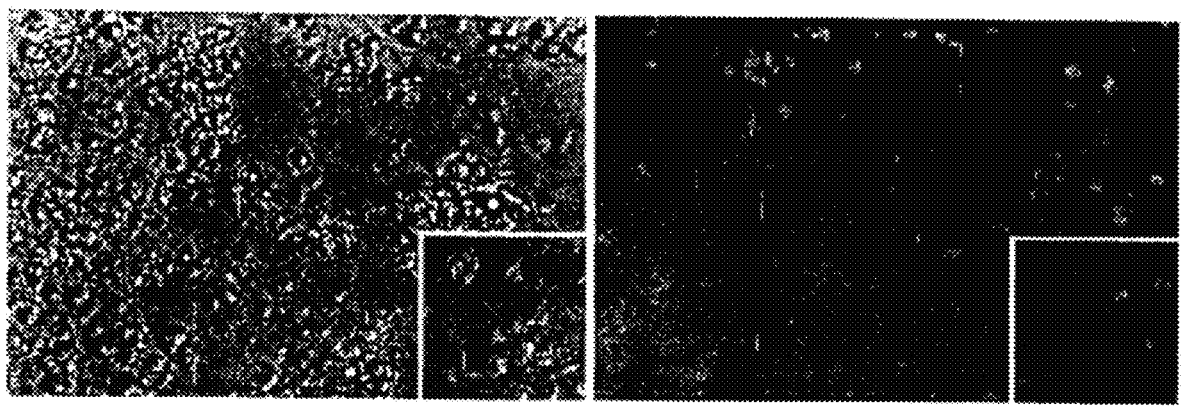
FIG. 5 contains two microscopy images of dendritic cells (DCs) comprising FITC-conjugated NF-kB ODN; left panel is a phase contrast image and right panel is a fluorescence image.

To demonstrate that DCs can take up double-stranded ODN efficiently, mouse bone marrow (BM)-derived DCs were propagated in GM-CSF+IL-4 (IL-4 DC) for 4-5 days and exposed to FITC-conjugated NF-KB ODN for time periods ranging from 2-36 hours. As shown in FIG. 5, the majority of DCs (>80%) exhibited fluorescence, indicating the presence of NF-KB ODN. Intracellular ODN was detected for at least 14 days in culture. During this time, DCs remained viable without evidence of toxicity. Peak fluorescence was noted after an 18 hour exposure of the DCs to NF-KB ODN. DCs cultured with GM-CSF+IL-4 for 6-7 days developed to fully mature cells that lose their phagocytic capacity. When fully mature DCs (CD40+, CD80+, CD86+, MHC class and MHC class III) were exposed to NF-KB ODN, no fluorescence was observed in the cells indicating an inability to take up the FITC-conjugated oligonucleotide, consistent with the inability of these cells to process exogenous antigen.

Example 4

Treatment of Type 1 Diabetes with NF-KB ODN Treated Ex Viveo DCs

To determine whether NF-KB ODN DCs were capable of inhibiting type 1 diabetes development, non-obese diabetic (NOD) mice were used, which is an art recognized model for diabetes development. At age 7 weeks, female NOD mice were treated with DCs. The DCs were isolated from NOD mice in accordance with the methods described in Example 3 above. The DCs were then propagated in the presence of either NF-KB ODN or IL-4 for 5 days and then pulsed with islet antigen (AG) where indicated. The mice were injected with $2\times10^6$ DCs and diabetes development was monitored by electronic glucometer. A glucose serum level of >350 mg/ml indicated diabetes development.

Intact islets from NOD mice (between 4-5 weeks old) were isolated by controlled collagenase digestion of perfused pancreas. The islets were handpicked to ensure purity from any non-endocrine tissue and collected in phosphate-buffered saline subjected to five cycles of freeze-thawing (37° C. for 5 minutes, −80° C. for 5 minutes). The lysate was then adjusted with PBS to provide 1 islet cell per 10 DCs. DCs were then pulsed overnight with the appropriate volume of islet lysate, washed extensively and injected into the NOD mice.

Figure 6A:
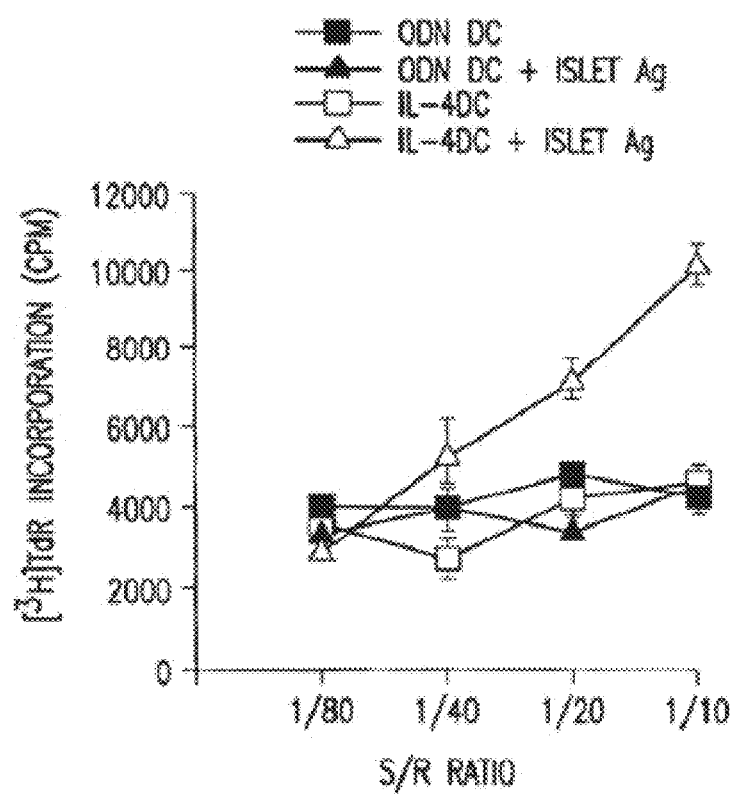
FIGS. 6A-6D is a multi-graph panel showing that the immunostimulatory capacity of DC from NOD mice is significantly inhibited by NF-k ODN as measured by T cell proliferation in FIG. 6A, CD80 marker expression in FIG. 6B, CD86 marker expression in FIG. 6C, and MHC Class I marker expression in FIG. 6D.
Figure 6B:
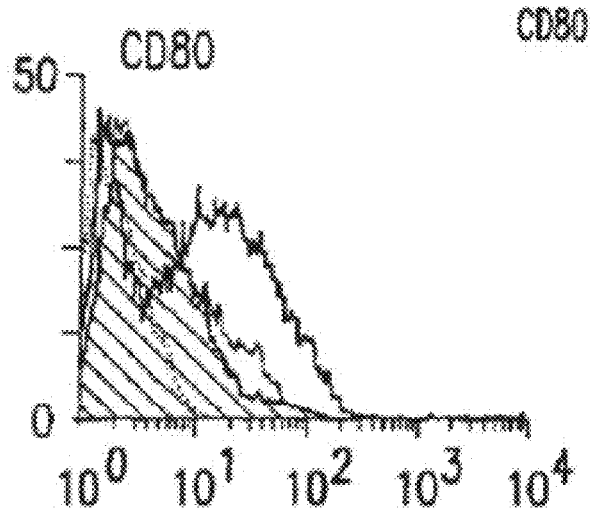
Figure 6C:
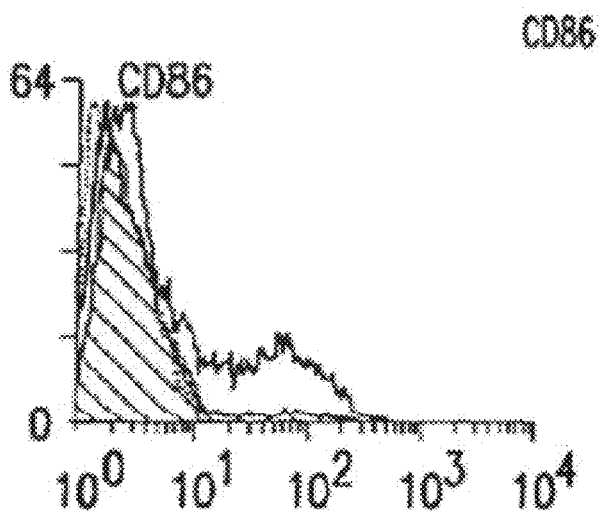
Figure 6D:
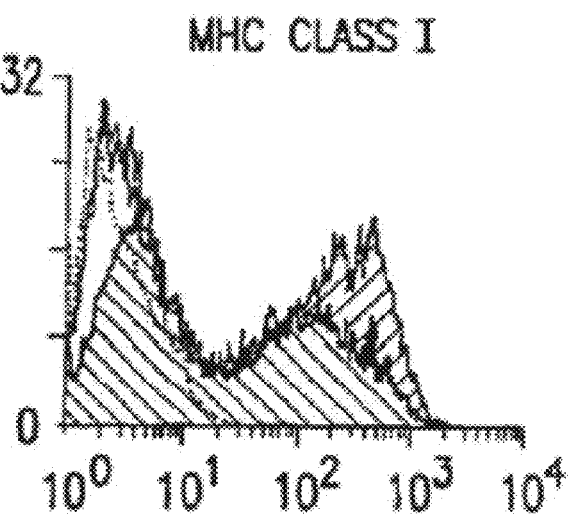
Figure 7:
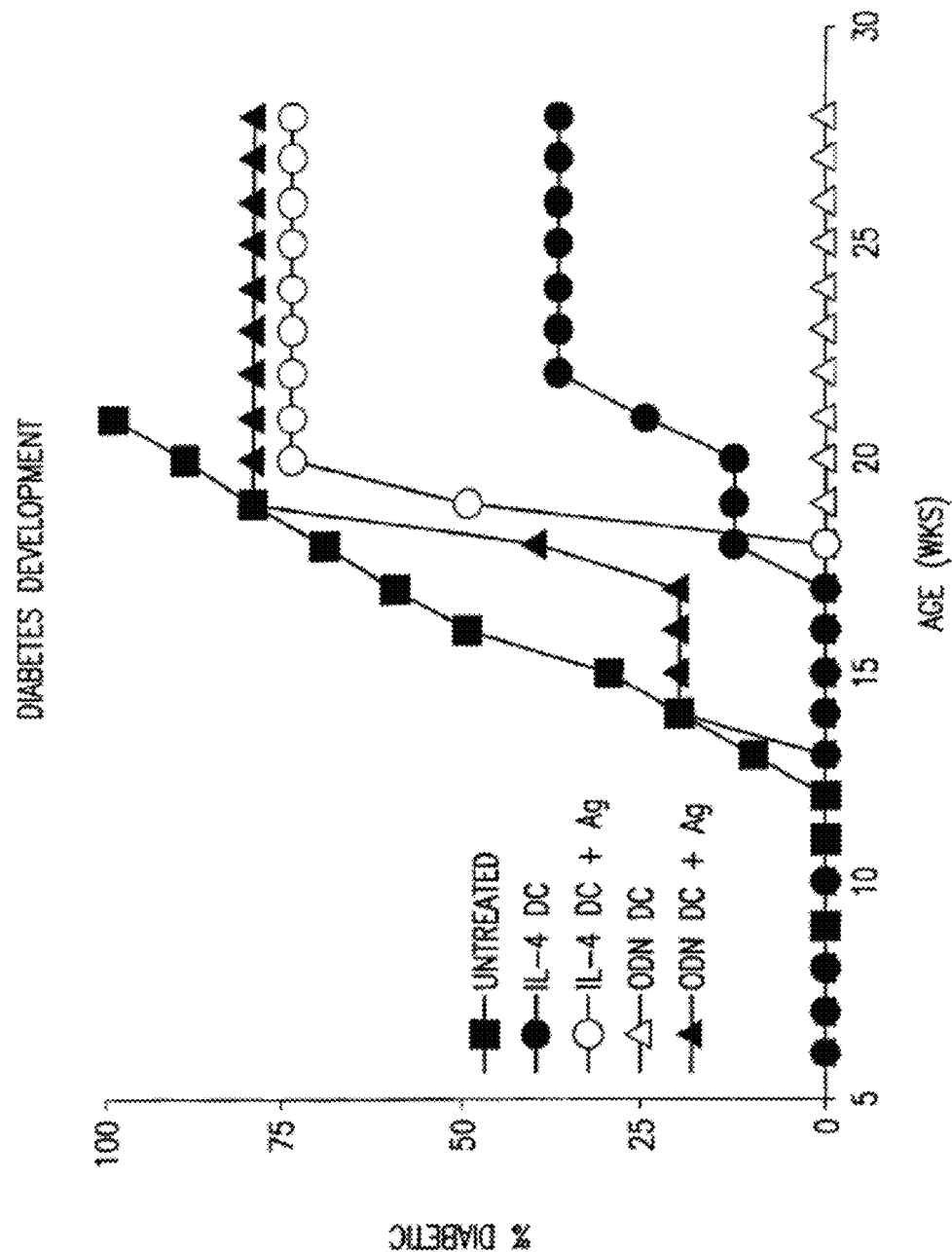
FIG. 7 is a graph showing that NF-kB ODN DC administration prevents the onset of type 1 diabetes development in NOD mice.

FIG. 6A indicated that NOD bone marrow-derived IL-4 DC, but not NF-KB ODN DC, pulsed with islet antigen lysate, strongly induced T-cell proliferation. In addition, NOD bone marrow-derived NF-KB ODN significantly inhibited CD80 and CD86 compared to NOD bone marrow-derived IL-4 DCs which expressed high levels of costimulatory molecules on their surface (see FIG. 6B). Furthermore, NF-KB ODN DCs inhibited diabetes development in NOD mice dramatically. FIG. 7 shows 100% of NOD mice treated with NF-KB ODN DCs had normal levels of serum glucose at the age of 32 weeks whereas 100% of untreated mice developed diabetes before the age of 17 weeks.

Example 5

Treatment of Type 1 Diabetes with Antisense Oligonucleotide-Loaded Microspheres

Figure 8A:
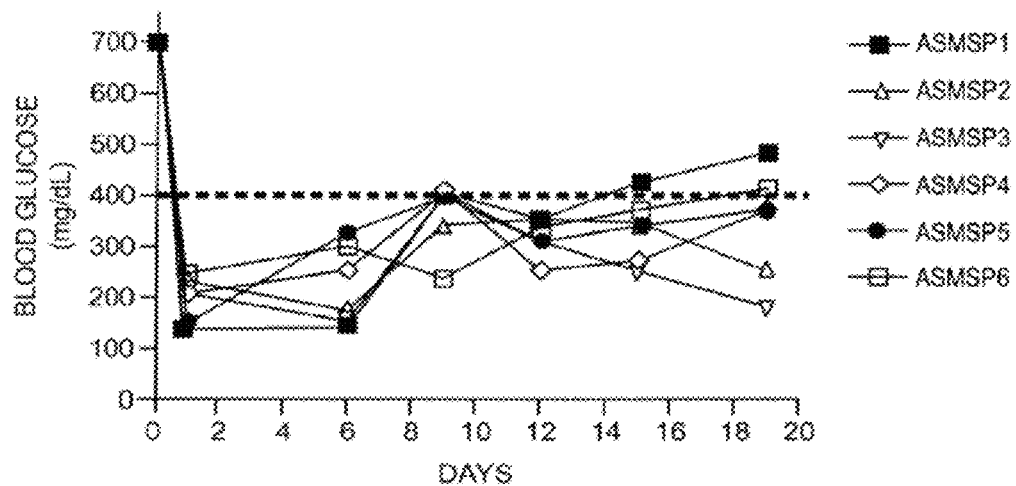
FIG. 8A is a graph summarizing the blood glucose levels from new-onset diabetic mice treated with microspheres containing antisense oligonucleotides.
Figure 8B:
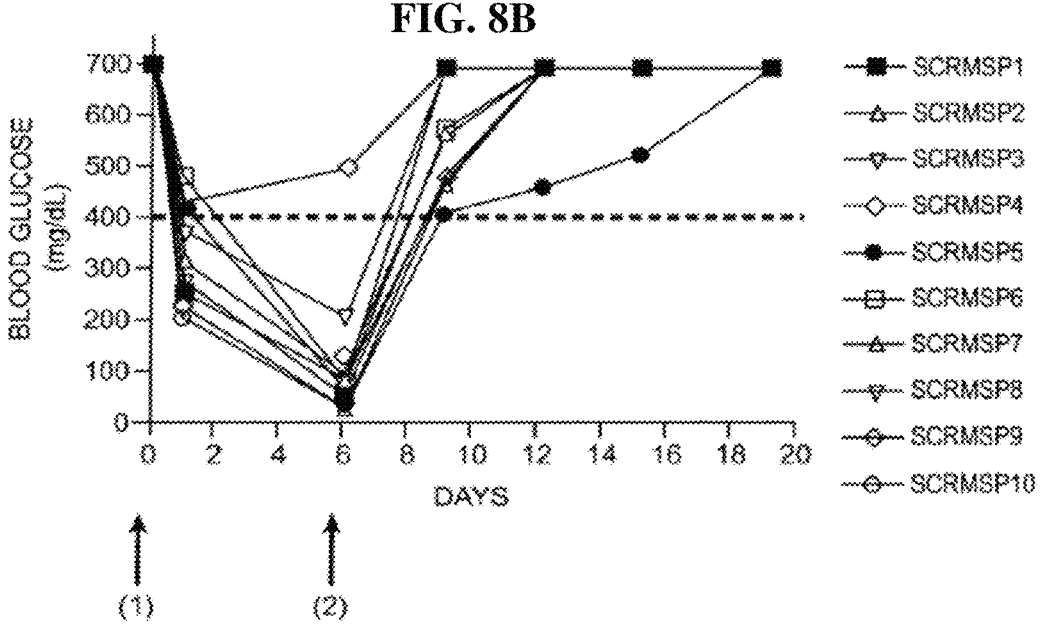
FIG. 8B is a graph summarizing the blood glucose levels from new-onset diabetic mice treated with microspheres containing scrambled oligonucleotides.

The ability of antisense oligonucleotide microspheres to reverse the symptoms of diabetes in early onset NOD mice was tested and a timeline for these experiments is shown in FIG. 9A. NOD mice with early onset diabetes were selected by testing blood glucose levels and identifying animals that have a blood glucose level greater than 400 mg/dL. The selected animals were given insulin pellets to normalize blood glucose levels to below 300 mg/dL. The insulin was withdrawn and a series of parenteral injections of microspheres was then started. Six animals were injected twice weekly with microspheres containing the CD40, CD80 and CD86 antisense oligonucleotides. A further ten animals were injected with microspheres containing a mixture of oligonucleotides with scrambled sequences that were not directed against CD40, CD80 and/or CD86. Each injection for both groups of animals comprises oligonucleotide-loaded microspheres in 100 µL of injection volume. After the commencement of the injection protocol, blood glucose levels were sampled twice weekly and animals are non-fasting during the experiment. The results were plotted in FIG. 8A, wherein the indicator (1) signified insulin pellet installation and indicator (2) signified insulin pellet removal and initiation of MSP injections twice weekly. It is noted that the maximum blood glucose value reported in FIG. 8B was 700 mg/dL, which corresponds to the maximum reading of the meter used. Thus, a 700 mg/dL data point indicated in a blood glucose reading of 700 mg/dL or higher. All animals in the group that received the microspheres containing the mixture of CD40, CD80, CD86 antisense oligonucleotides (AS-MSP1 through AS-MSP6) showed significantly lower glucose levels than the animals that received the microspheres with scrambled oligonucleotides (SCR-MSP1 through SCR-MSP10). Furthermore, four of six animals in this AS-MSP group showed a blood glucose level below 400 mg/dL, typically considered to be a threshold indicator of diabetes onset.

In FIG. 9A, the timeline for the experiments is shown. The mean non-fasting blood glucose (FIG. 9B) and the mean fasting blood glucose levels for each group were plotted (FIG. 9C) (+/−SEM). Insulin was administered daily until blood glucose fell below 300 mg/dL. Insulin then was stopped whereupon AS-MSP were administered subcutaneously. Animals received 2 mg AS-MSP per kg body weight two times a week for 3-4 weeks. In some mice, AS-MSP administration was withdrawn as shown in FIG. 9A. Multiple rounds of AS-MSP administration in new-onset diabetic NOD female mice, FIGS. 9B and 9C, improved blood glucose levels and resulted in stable fasting euglycemia, even after AS-MSP withdrawal relative to untreated animals (control), animals treated with PBS or animals treated with scrambled oligonucleotides (SCR-MSP) microspheres.

Figure 10C:
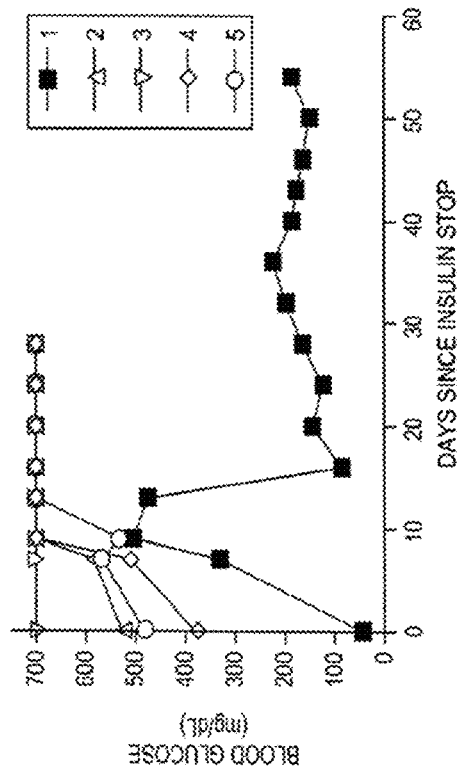
FIGS. 10A-10C are graphs showing the reversal of the type 1 diabetes phenotype in NOD mice within 15 days after administration of AS-MSP.
Figure 10A:
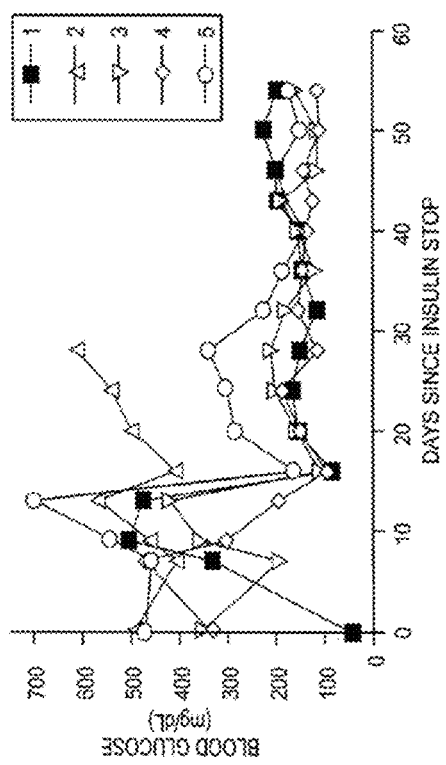
Figure 10B:
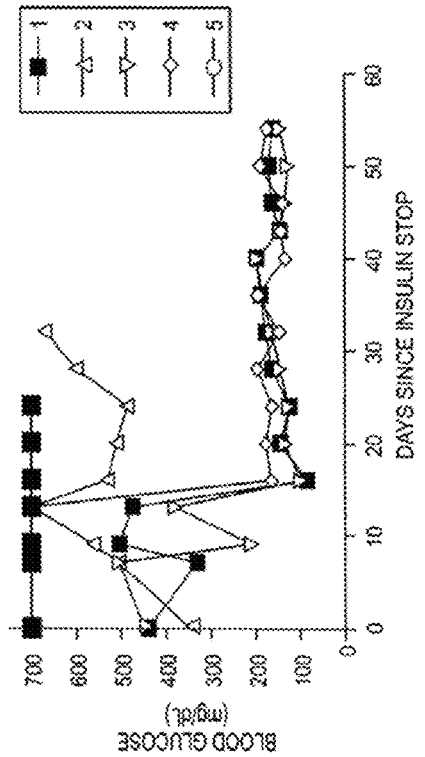
Figure 11:
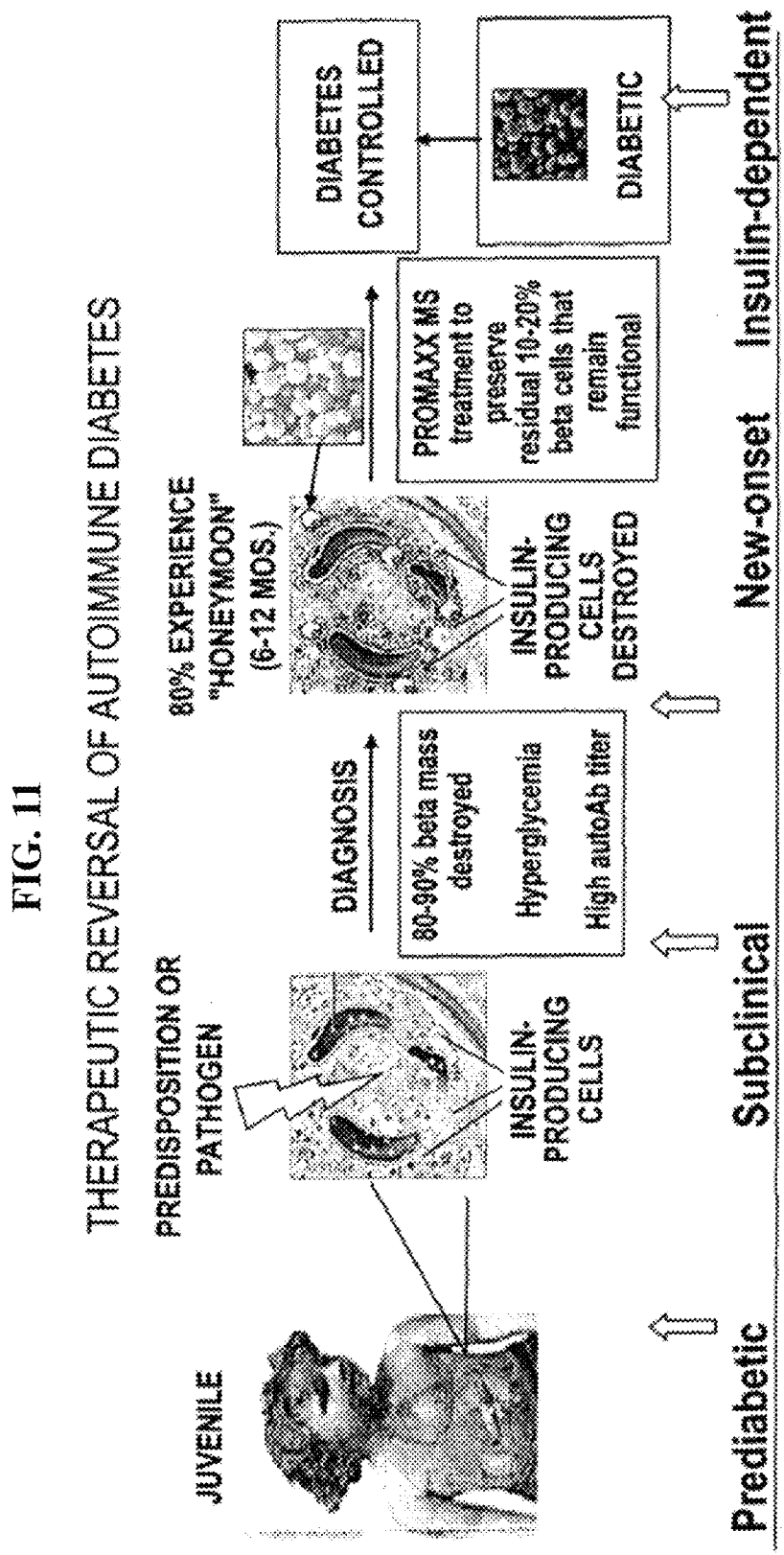
FIG. 11 is a flow diagram depicting therapeutic reversal of autoimmune diabetes.

Administration of AS-MSP to NOD mice, FIG. 10A-C, returned the blood glucose levels of said mice to normal levels and the normalization of said blood glucose level was maintained for an extended period of time. As shown in FIGS. 10B and 10C, AS-MSP were administered between days 0-30 after insulin administration was stopped. The blood glucose level returned to normal by day 15 post insulin stop and remained at a normal level until the end of the monitoring period (day 55). A diagram showing the impact of therapeutic reversal of autoimmune diabetes is shown in FIG. 11.

Example 6

Microspheres Loaded with Human Antisense Oligonucleotides

The following human antisense sequences are used in the Example described below:

```
SEQ ID NO; 17:
h-CD40 AS: 5' ACTGGGCGCCCGAGCGAGGCCTCTGCTGAC 3'

SEQ ID NO; 18:
h-CD86 AS: 5' AAGGAGTATTTGCGAGCTCCCCGTACCTCC 3'

SEQ ID NO: 19:
h-CD80 AS: 5' TTGCTCACGTAGAAGACCCTCCAGTGATG 3'
```

Approximately 6.0 mg of poly-L-lysine in aqueous solution was heated to 70° C. in a water bath into a 15 ml conical tube. 6.9 mg of a mixture of CD40, CD80 and CD86 antisense oligonucleotides (SEQ ID NOs. 17, 18 and 19 as described above) in aqueous solution was heated to 70° C. in a water bath into a 15 ml conical tube. A 12.5% PEG/12.5% PVP solution was also heated to 70° C. in a water bath. The poly-L-lysine was pipetted into the antisense oligonucleotides solution and the resulting suspension was mixed by briefly swirling with the pipette tip. Next, the tube was quickly returned to 70° C. water bath and incubated for 5 minutes. The PEG/PVP solution was then added to the ASO/PLL solution and mixed briefly by swirling with the pipette tip.

The tube was then quickly returned to 70° C. water bath and incubated for 5 to 10 minutes. Next, the formulation was cooled to 4° C. using at a rate of 1° C./minute cooling. The samples were then water washed on ice.

The samples were then centrifuged at 4750 rpm for 10-30 minutes at 4° C. The supernatant was then removed and the microspheres were resuspended with an equal volume of $H_2O$ at 4° C. The microspheres were then washed 3 additional times by centrifugation, washing and resuspension at 4750 rpm for 5-10 minutes at 4° C. by removing the supernatant, resuspending the microspheres and resuspending with an equal volume of $H_2O$ at 4° C.

After the fourth centrifugation step, the microspheres were resuspended to a concentration of approximately 10 mg/ml. The samples were then frozen on dry ice or in a −80° C. freezer for 30 minutes and lyophilized to dryness over approximately a 24 hour period.

Example 7

Accumulation of Microspheres into Pancreatic Lymph Nodes

Figure 12A:
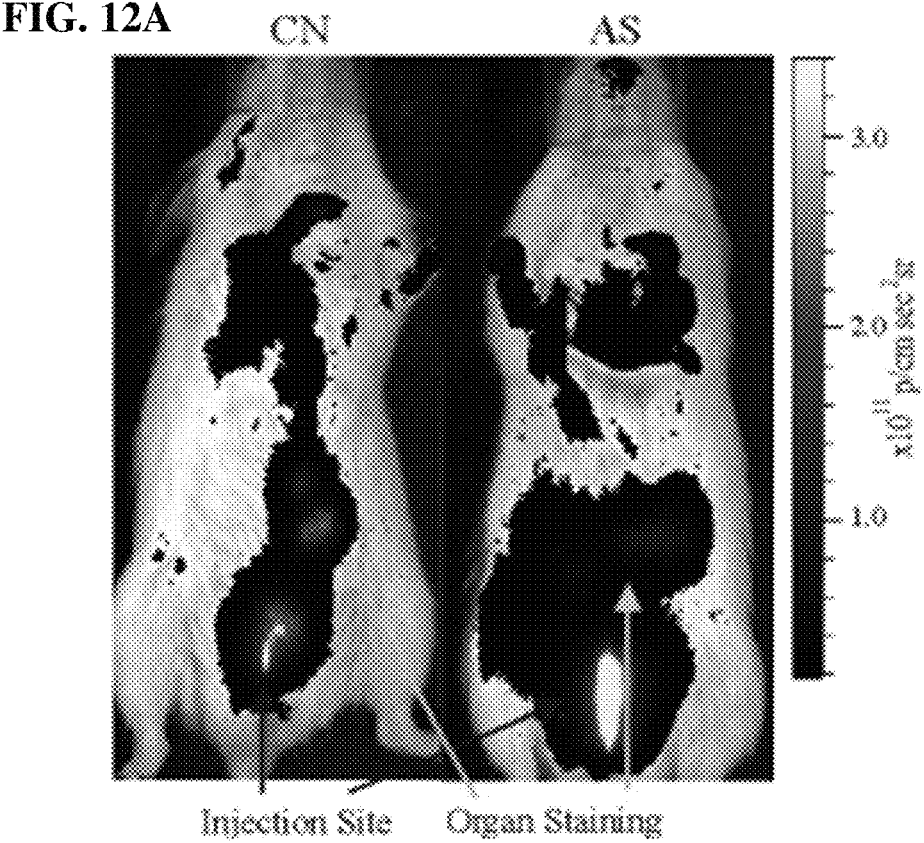
FIG. 12A is a figure summarizing live animal imaging in an IVIS Lumina workstation.
Figure 12B:
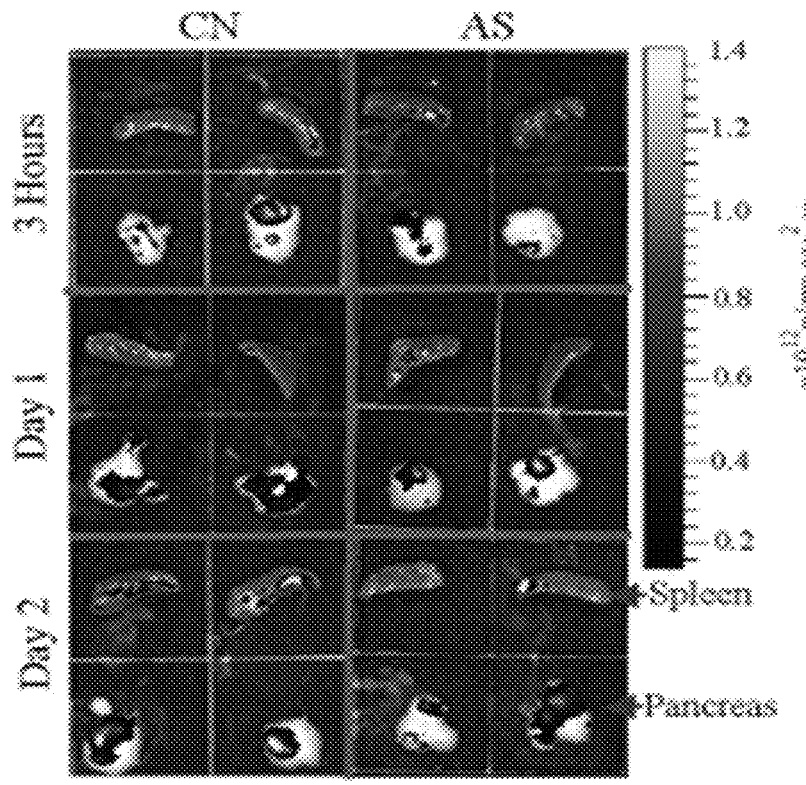
FIG. 12B is a figure summarizing localized accumulation of fluorescence-labeled microspheres following injection overlying the pancreas into a mouse.
Figure 12C:
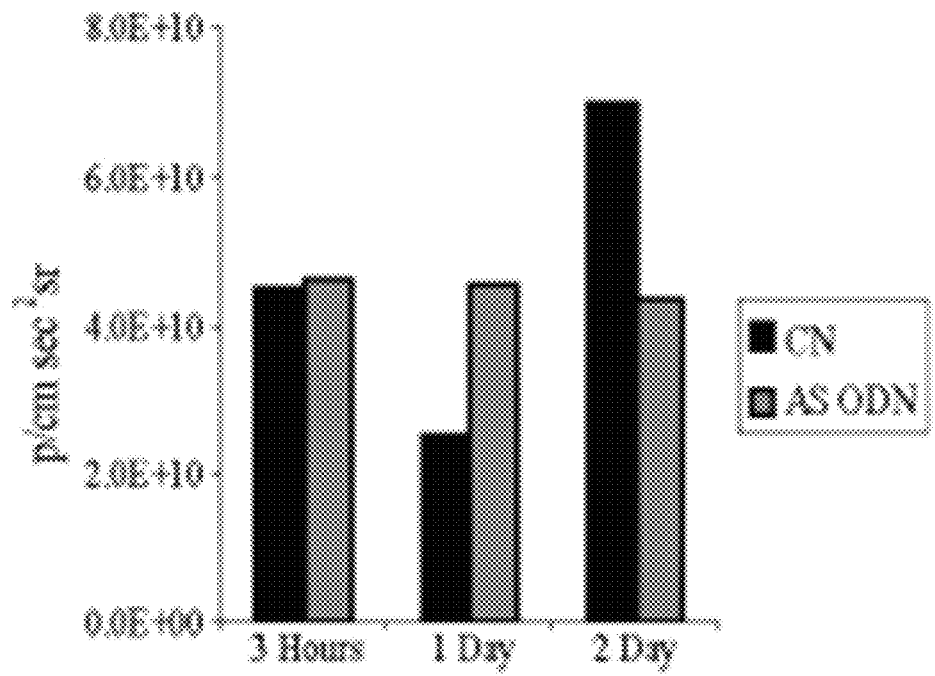
FIG. 12C is a graph summarizing fluorescence accumulation of fluorescence-labeled microspheres in a mouse for two days.
Figure 12D:
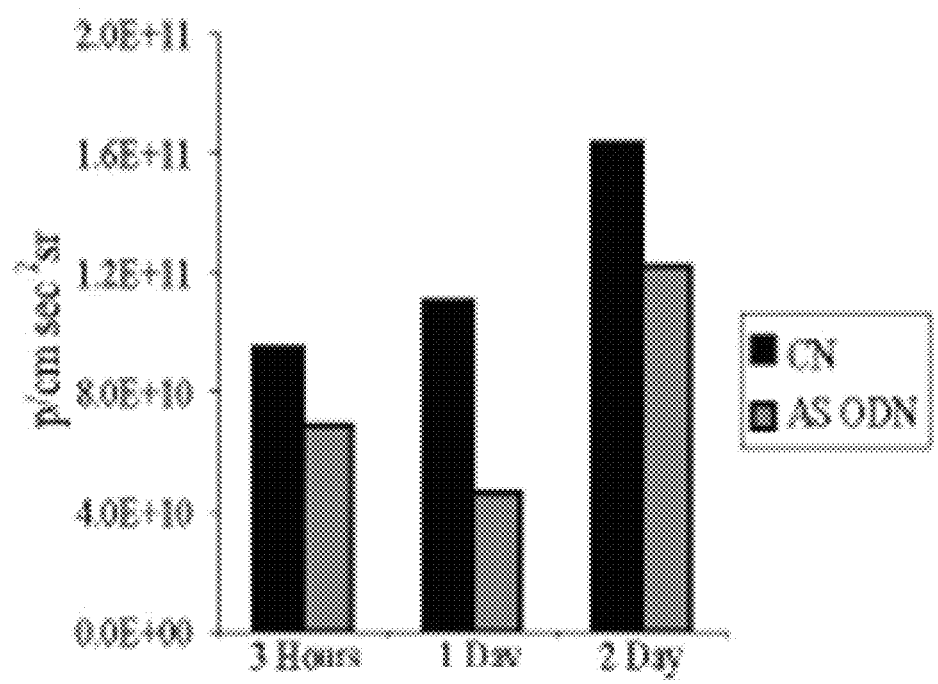
FIG. 12D is a graph summarizing fluorescence accumulation of fluorescence-labeled microspheres in a different mouse for two days.
Figure 13:
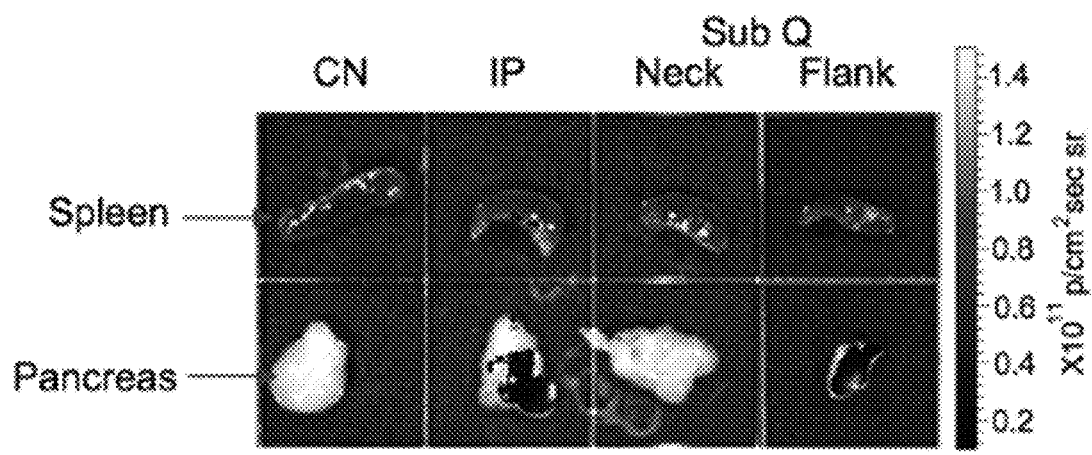
FIG. 13 is a figure summarizing localized accumulation of fluorescence-labeled microspheres following injection distal to the pancreas into a mouse.

Following the injection of 2 mg/kg of microspheres loaded with fluorescence-tagged oligonucleotides into mice, live animal imaging in an IVIS Lumina workstation was collected (FIG. 12A; CN refers to control microspheres without the antisense oligonucleotides, AS refers to the specific diabetes-suppressive microsphere with the antisense oligonucleotides). Following euthanasia of the mice, various organs and lymph nodes were collected and visualized separately (FIG. 12B). As shown, the fluorescence was concentrated inside the pancreas and to a very small degree the spleen. FIGS. 12C and 12D summarized the fluorescence accumulation in the pancreas of two different mouse recipients over two days. When the microspheres were injected at a site distal to the pancreas, there was no accumulation inside the pancreas or the pancreatic lymph nodes (FIG. 13; IP refers to intraperitoneal injection, Sub Q refers to subcutaneous injection at the indicated site).

Figure 14:
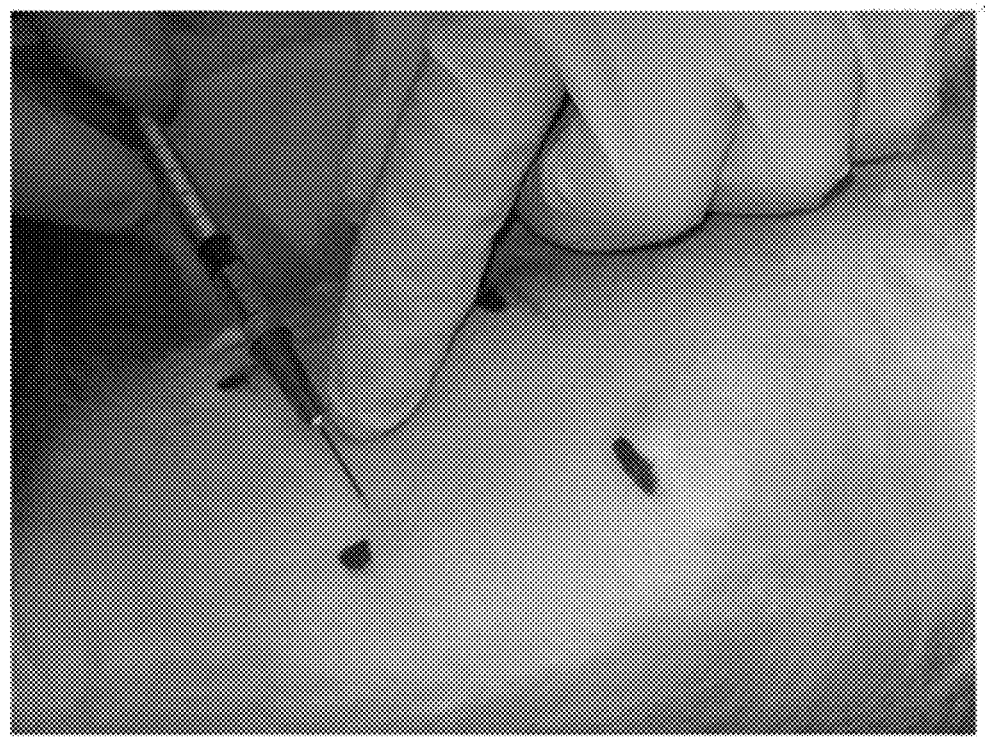
FIG. 14 is a figure summarizing the location of injection sites of fluorescence-labeled microspheres in a non-human primate.
Figure 15C:
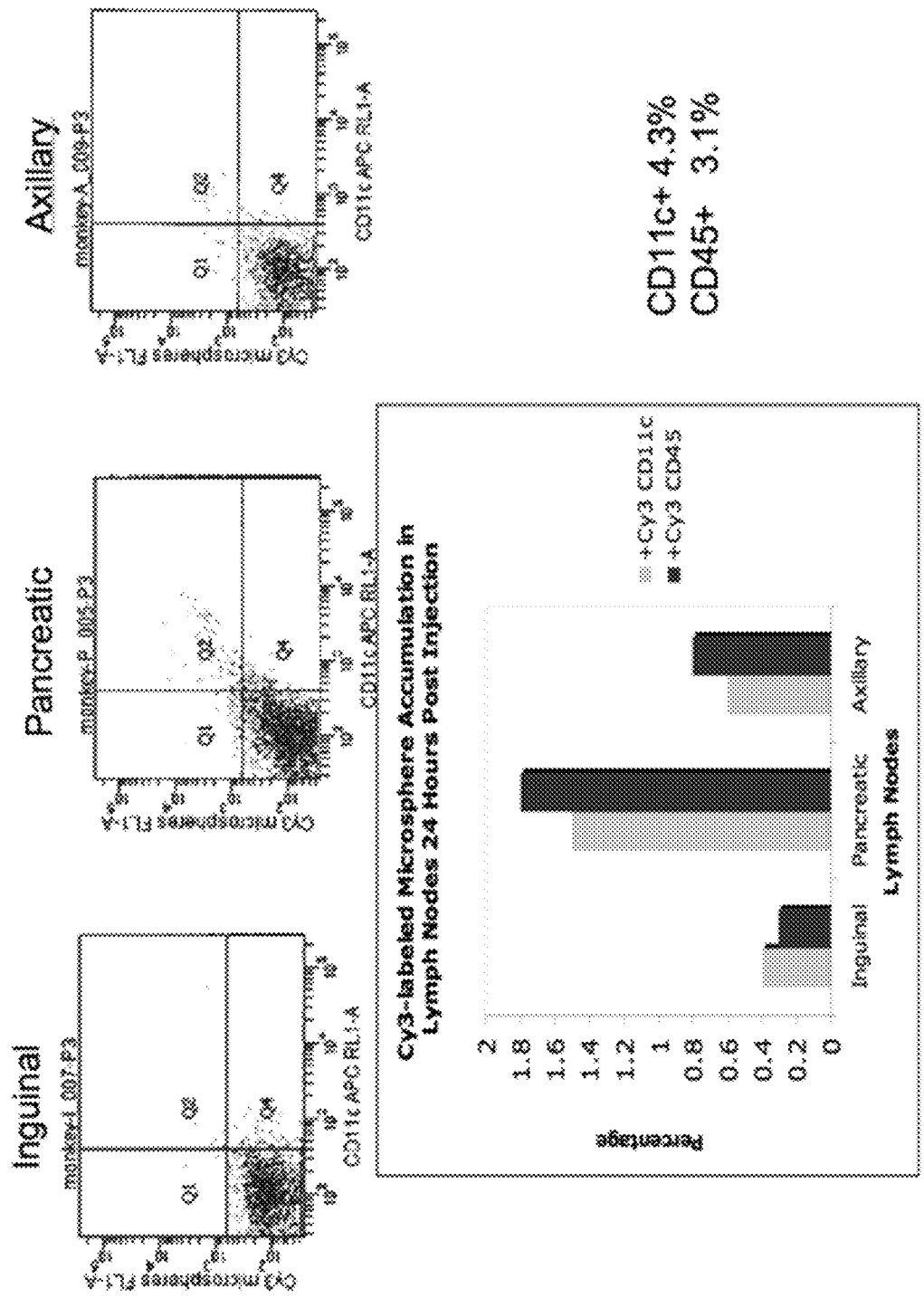

Following the injection of 2 mg/kg of microspheres loaded with fluorescence-tagged oligonucleotides into non-human primates at the location shown in FIG. 14. Accumulation of these microspheres was preferentially inside the pancreatic lymph nodes with very slight accumulation inside the liver, but not in other organs, FIG. 15A-C. The fluorescence was concentrated inside CD11c+ CD45+ cells from the pancreatic lymph nodes which were by definition dendritic cells.

Example 8

Accumulation of Tolerogenic DCs into Pancreatic Lymph Nodes

Figure 16:
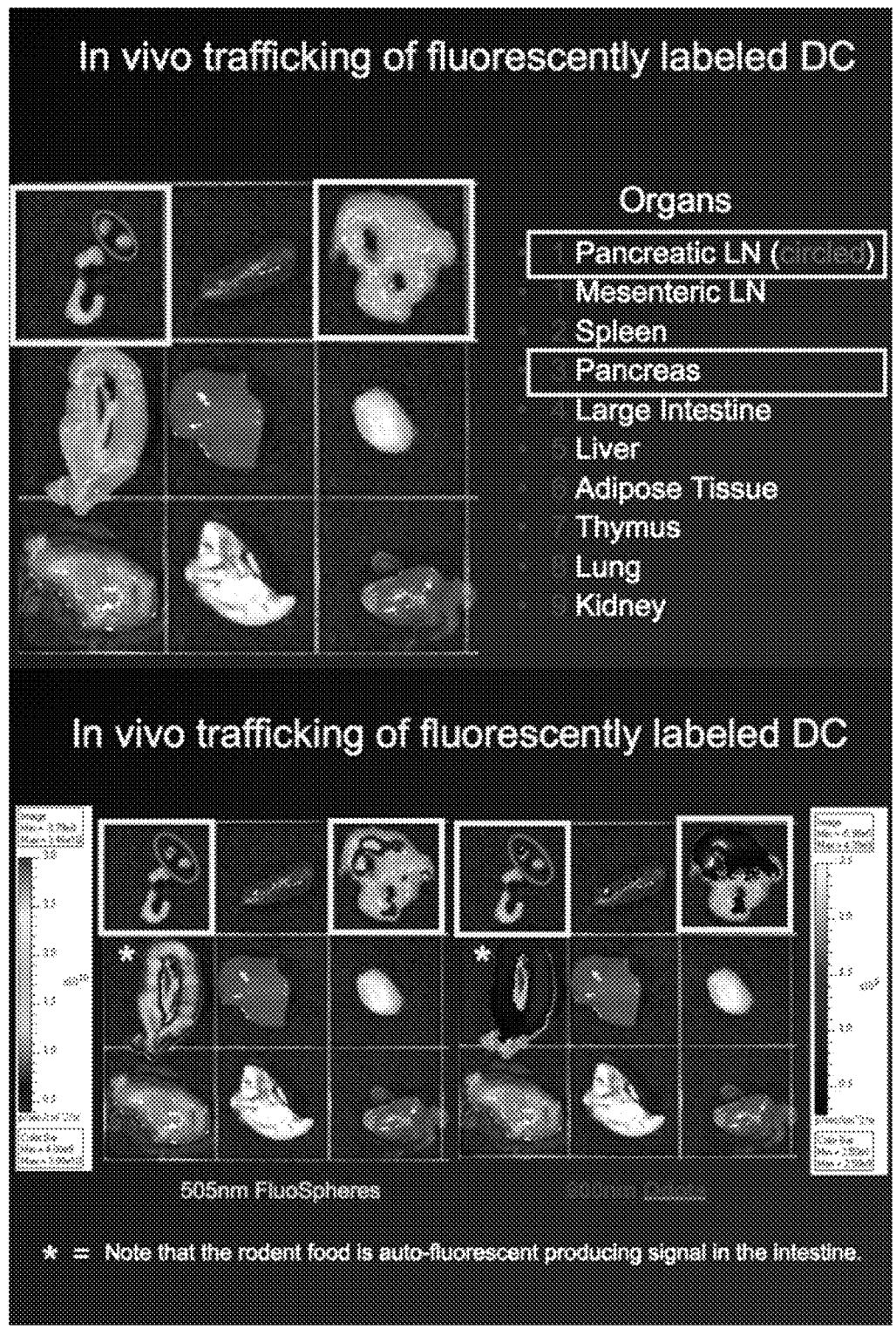
FIG. 16 is a figure summarizing localized accumulation of fluorescence-labeled tolerogenic dendritic cells (iDC) following injection in a mouse.

Following the injection of $2 \times 10^6$ cells generated ex vivo from bone marrow progenitors with fluorescence-tagged spheres, mice were euthanized and various organs including lymph nodes were collected. The organs were visualized under the IVIS Lumina Workstation (FIG. 16), showing accumulation of the ex vivo tolerogenic dendritic cells preferentially in the pancreas and the pancreatic lymph nodes.

Figure 17:
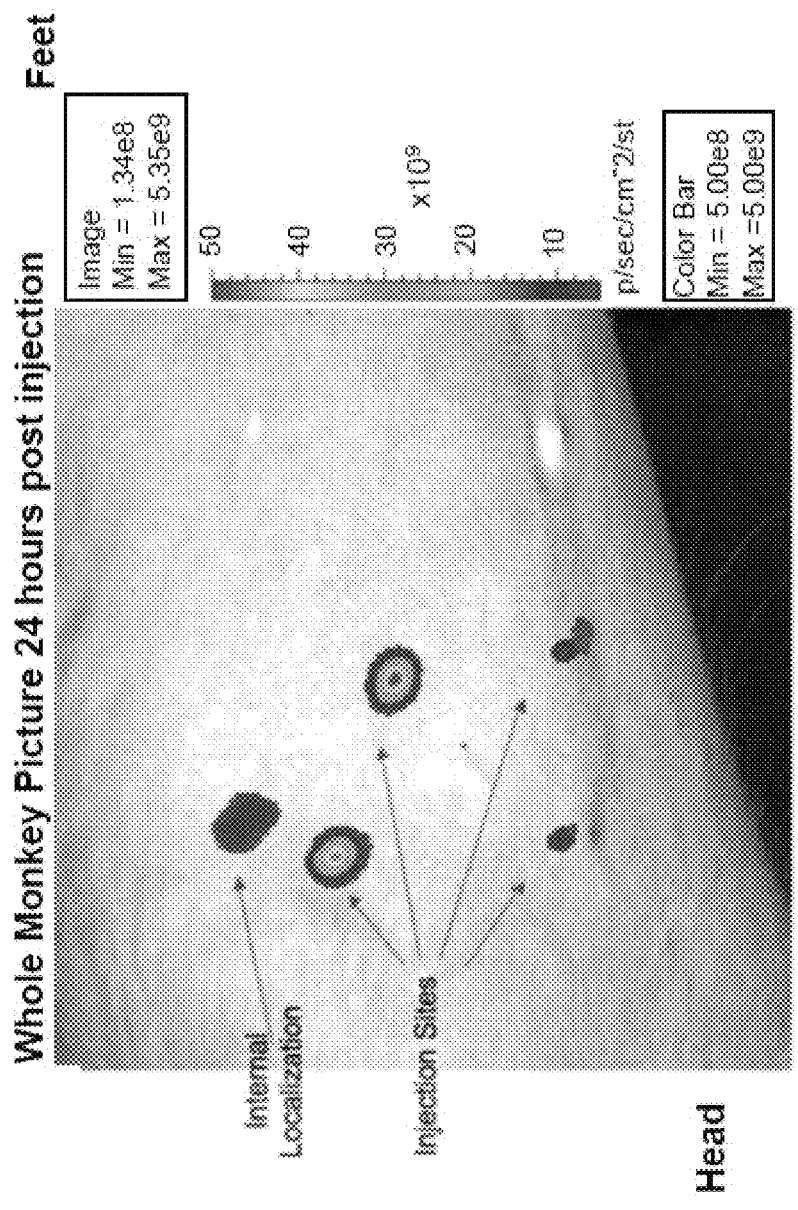
FIG. 17 is a figure summarizing the location of the injection sites of fluorescence-labeled iDC in a non-human primate.
Figure 18:
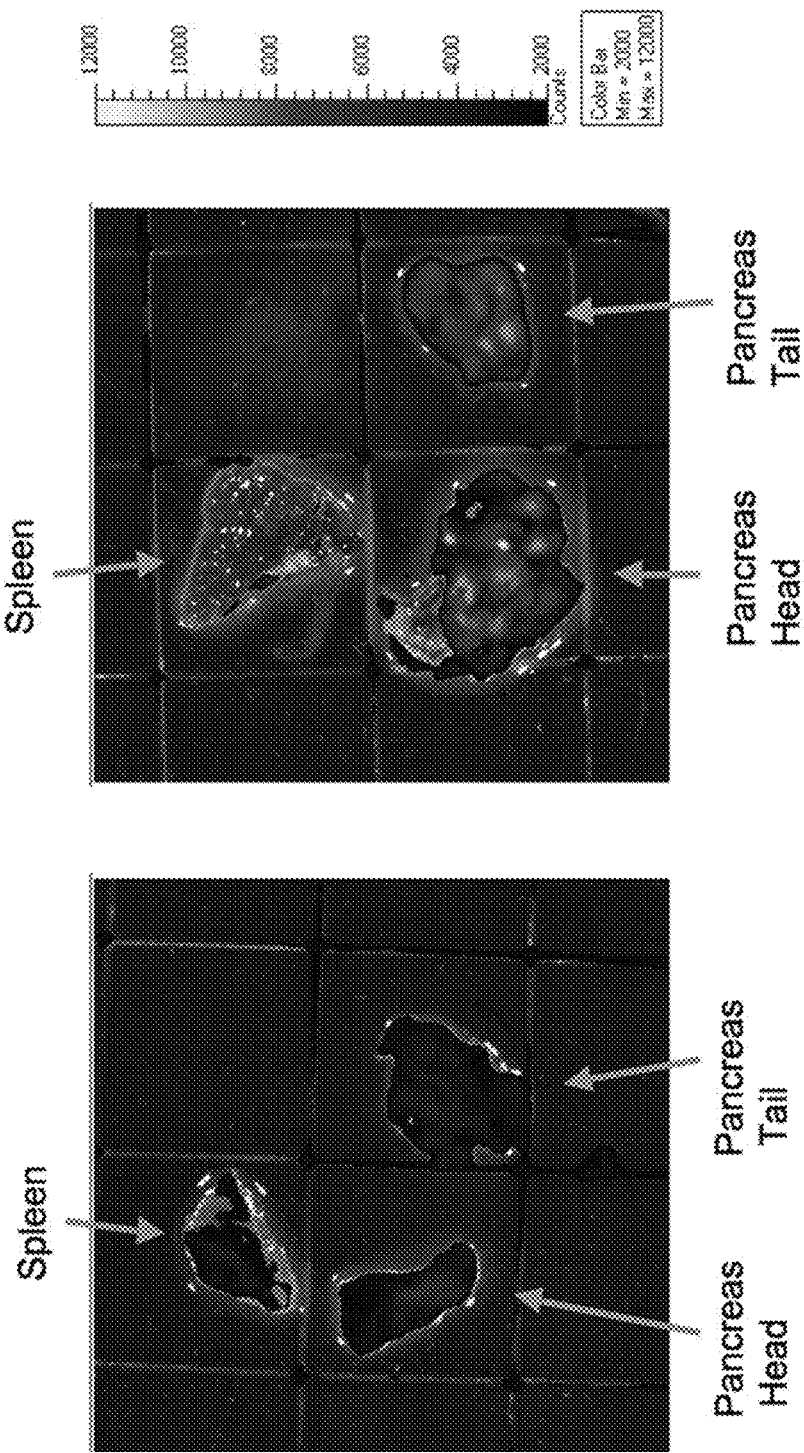
FIG. 18 is a figure summarizing localized accumulation of fluorescence-labeled iDC following injection in a non-human primate.

Following the injection of $2 \times 10^6$ cells generated ex vivo from peripheral blood mononuclear progenitors with fluorescence-tagged spheres, non-human primates were euthanized and various organs including lymph nodes were collected. Accumulation of the ex vivo tolerogenic dendritic cells occurred preferentially inside the pancreas and the pancreatic lymph nodes but not in other organs, FIG. 16. The results were comparable in two non-related non-human primates, FIG. 18. The injection was conducted at the edges of a rectangle that overlies the expected location of the pancreas, FIG. 17.

Example 9

Preparation, Dosage and Administration of Tolerogenic Human DCs

After receiving confirmation of absence of microbial infection/contamination, endotoxin <5 EU/kg body weight, viability>70% and confirmation of DC purity (by flow cytometry), cells were centrifuged at 380×g for 10 minutes and then resuspended in a volume of 0.5 mL-1.0 mL of sterile 5% human serum albumin and were aspirated into a sterile 3 mL syringe. The needle was recapped replaced by a 27 gauge ⅝" needle. The syringe was labeled with coded information about the human subject and delivered for administration to where the subject was located within 24 hours. For subsequent injections, as well as for delivery of cells off-site, $2.5 \times 10^6$ cells were aliquoted per cryopreservation tube and the tubes were stored under liquid nitrogen conditions. The cells used as the first dose were injected within 2 hours.

The dosing plan is shown in FIG. 19. The maximum total amount of cells administered to a subject was $2.5 \times 10^6$ on each of the four treatment times (once every two weeks) for a total no more than $40 \times 10^6$ cells. Subjects received $1 \times 10^5$-$4 \times 10^7$ dendritic cells subcutaneously (four injections of equal numbers of cells that together amount to the desired total dose at four distinct sites anatomically-proximal to the pancreas). Per administration, four unique injection sites were designated inside the anterior abdominal wall perpendicularly-above the physical location of the stomach/pancreas. These four sites were within a quadrant of 3-4 square-inches.

The cells were delivered by a tuberculin syringe attached to a 27 g-½" needle underneath a raised "bleb" of skin at each of the four individual injection sites. The injection occurred slowly over a 20 second period in each of the physical abdominal sites.

Example 10

Figure 20A:
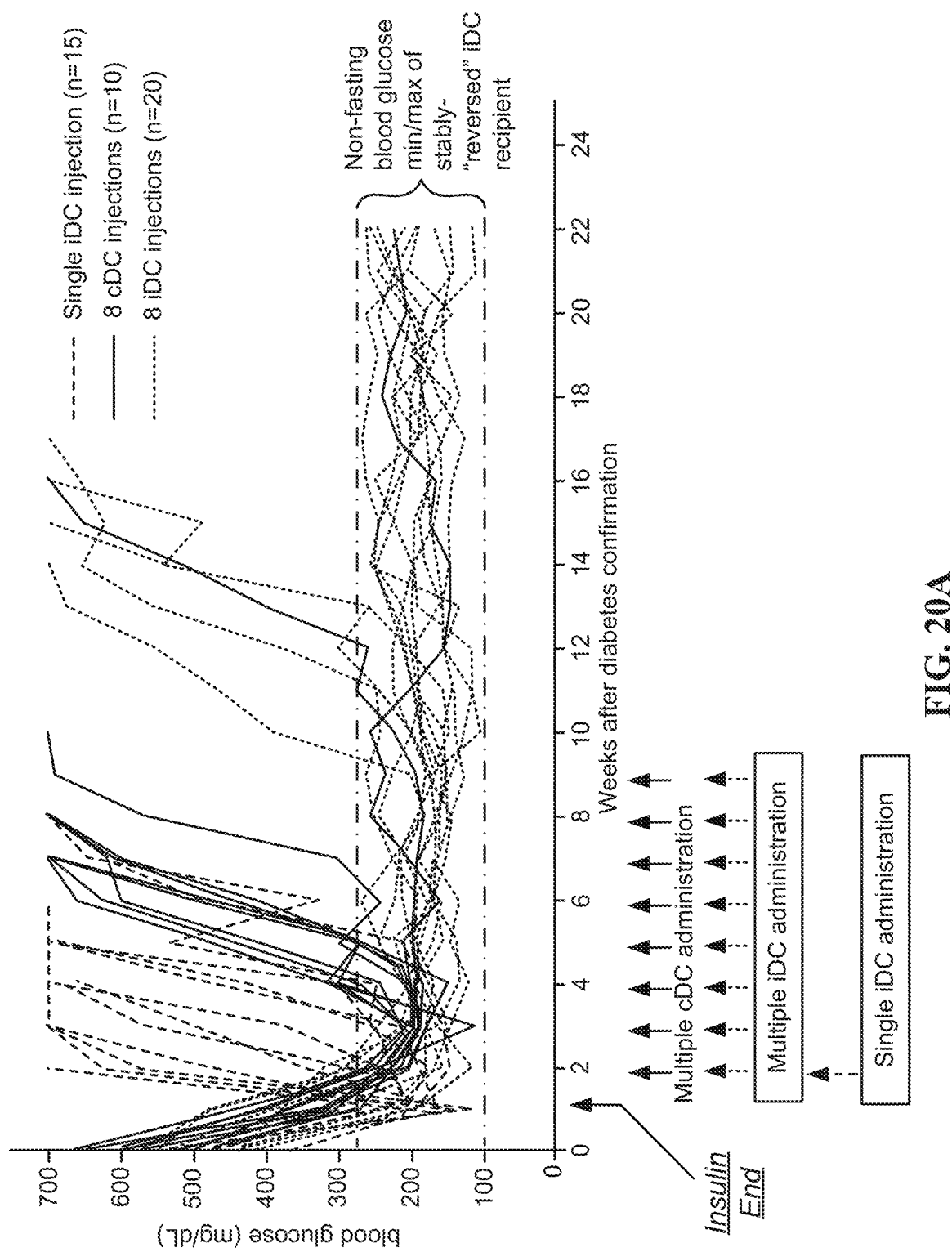
FIG. 20A is a graph summarizing blood glucose levels during the weeks following new-onset type 1 diabetes mice.
Figure 20B:
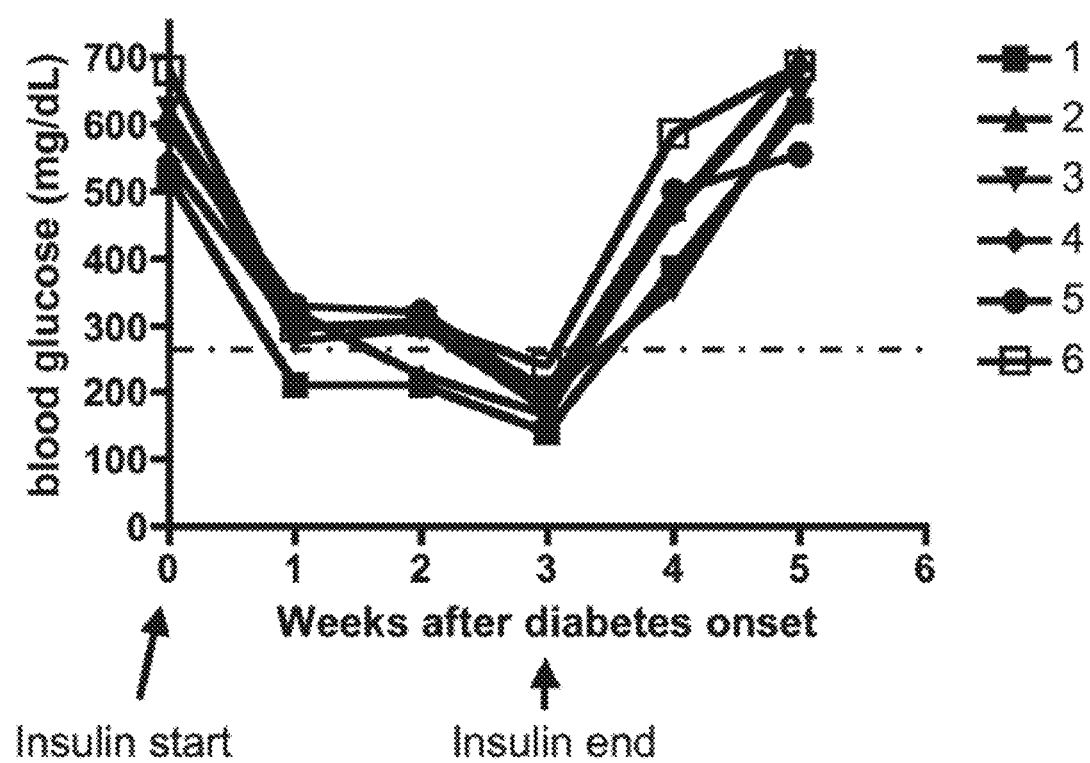
FIG. 20B is a graph summarizing blood glucose levels following insulin withdraw in new-onset diabetic mice.

Stable Treatment of Type 1 Diabetes is Achieved by Multiple Injections of Tolerogenic DCs Multiple tolerogenic DC injections (n=8) stably maintained glucose levels within a range between 100-280 mg/dL in most new-onset diabetic NOD mice, FIG. 20A. Multiple control DC injections (n=8) transiently reversed type 1 diabetes in a few recipients, albeit transiently. Single tolerogenic DC injections, compared to multiple injections were ineffective in restoration of blood glucose stability. The lines represented non-fasting blood glucose levels in individual NOD mice. Mice were administered insulin once diabetic hyperglycemia was confirmed up until the time glucose levels drop to below 280 mg/dL (5-8 days on average). At this point, insulin was withdrawn. Then, $2 \times 10^6$ DCs (control or tolerogenic) were injected subcutaneously at the abdominal flank overlying the gastrointestinal organs. Time 0 represented the time of diabetes confirmation. The black arrow below the x-axis showed the time of insulin withdrawal concomitant with the first DC injection. The gray arrows showed the times at which DC were administered (single or multiple). The dashed lines in the graph indicated the minimum and maximum non-fasting blood glucose levels measured in the reversed iDC treatment group. Blood glucose crossed the 280 mg/dL threshold within a day of insulin withdrawal, FIG. 20B, when new-onset diabetic NOD mice were not subjected to any other treatment.

Example 11

Tolerogenic DCs Delivery Promotes Increased Frequency of Suppressive B-Cells In Vivo $2 \times 10^6$ DCs (control or tolerogenic) were injected subcutaneously into the abdominal flank overlying the gastrointestinal organs in NOD female mice. Three days later, the spleens were collected and the frequency of the CD19+ B220+ CD11c− IL-10+ B-cells as well as B10 Bregs was measured by flow cytometry. Absolute numbers were calculated based on hematocrit measurements of total viable single cells recovered from the tissue.

Figure 21A:
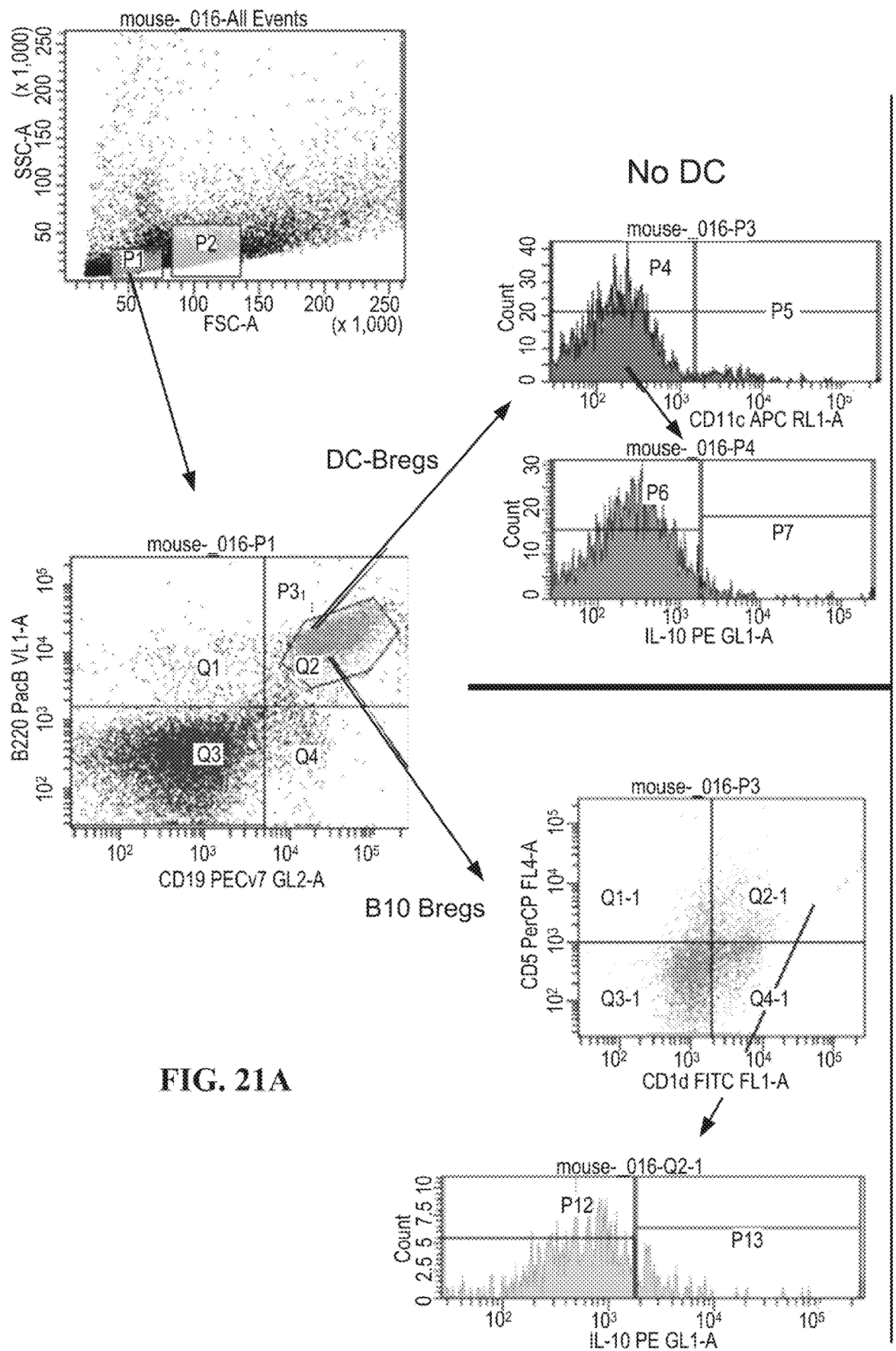
FIGS. 21A-21C is the flow cytometric approach used to identify and measure the frequency of B-cell populations.
Figure 21B:
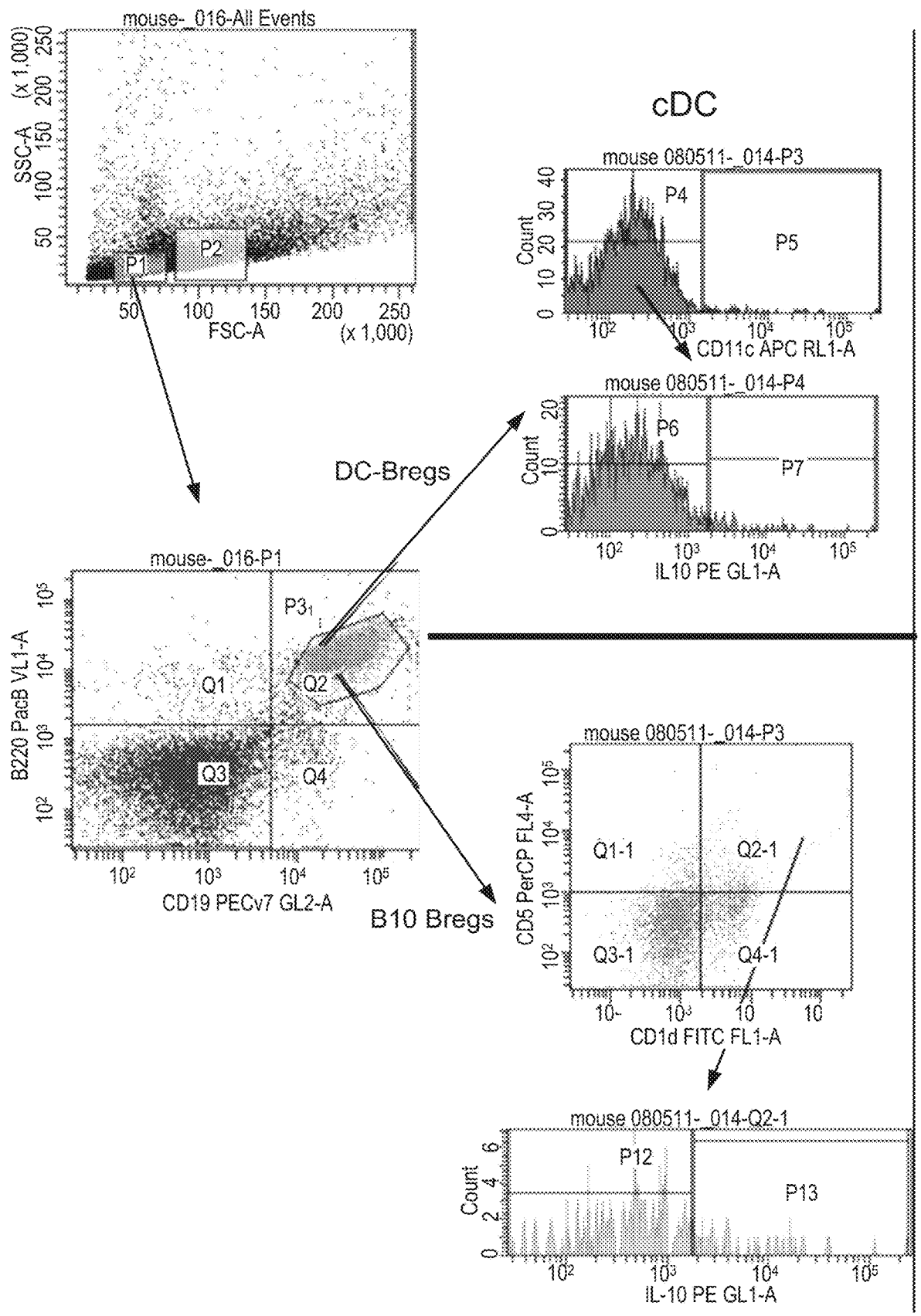

The flow cytometry approach used to identify and measure the frequency of the CD19+B220+ CD11c− IL-10+ cells (DC-Bregs; top two histograms) and B10 Bregs (bottom two histograms) was shown, in freshly-collected splenocytes of at least four different NOD recipients of each type of DC population (and PBS vehicle control), FIG. 21A, and in freshly-collected pancreatic lymph node single cells acquired from the same mice, FIG. 21B.

Figure 21C:
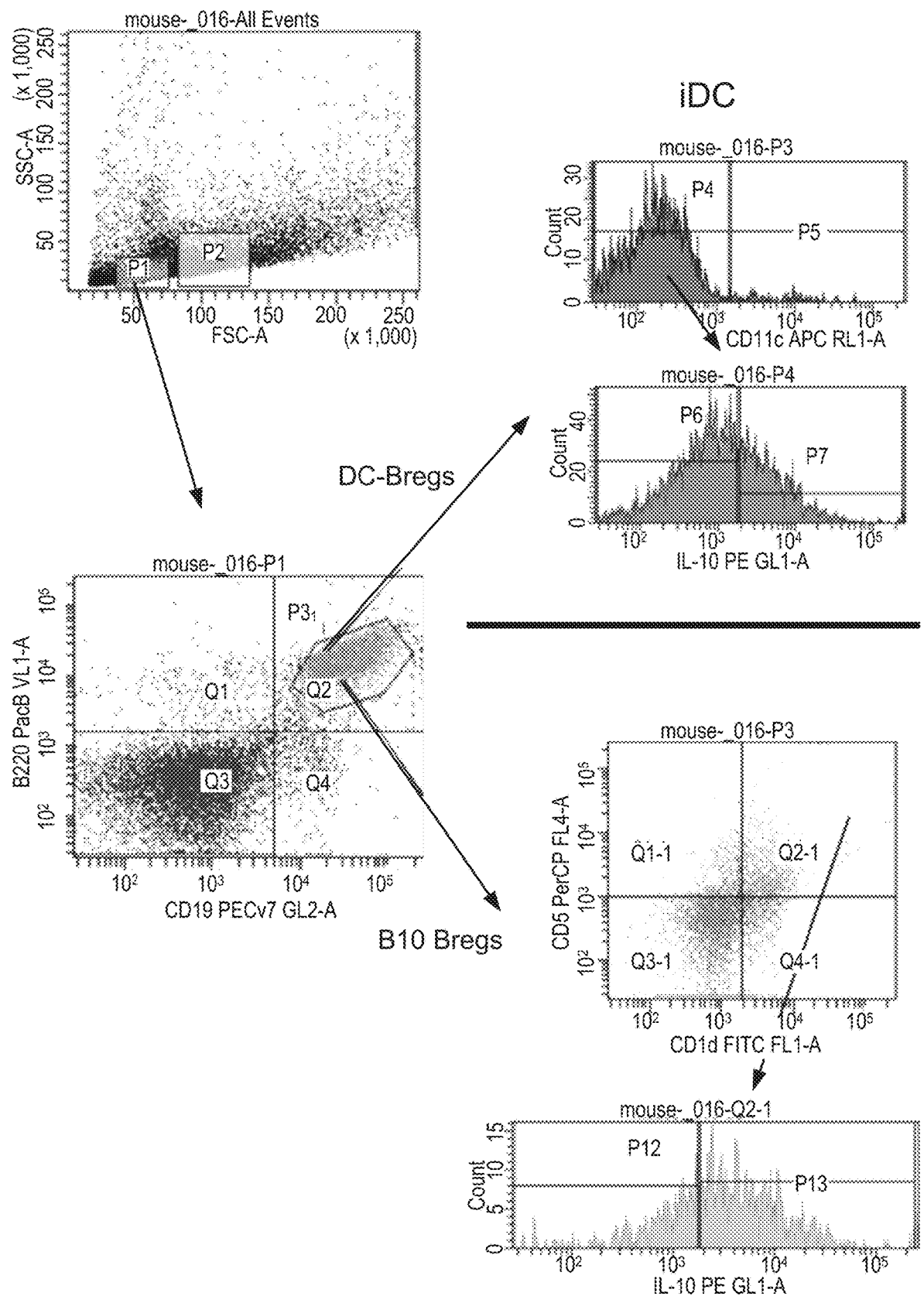

A graphic summary of the frequency of CD19+ B220+ CD11c− IL-10+ B-cells (DC-Bregs) measured by flow cytometry as a % of total splenocytes was shown in FIG. 21C. The number of mice from which tissue was collected per treatment type was shown at the top of the bars which represent the median value. The error bars reflected the standard deviation. The differences between iDC and cDC/ control untreated were statistically-significant (p<0.005, Kruskal-Wallis test of variance).

Figure 21D:
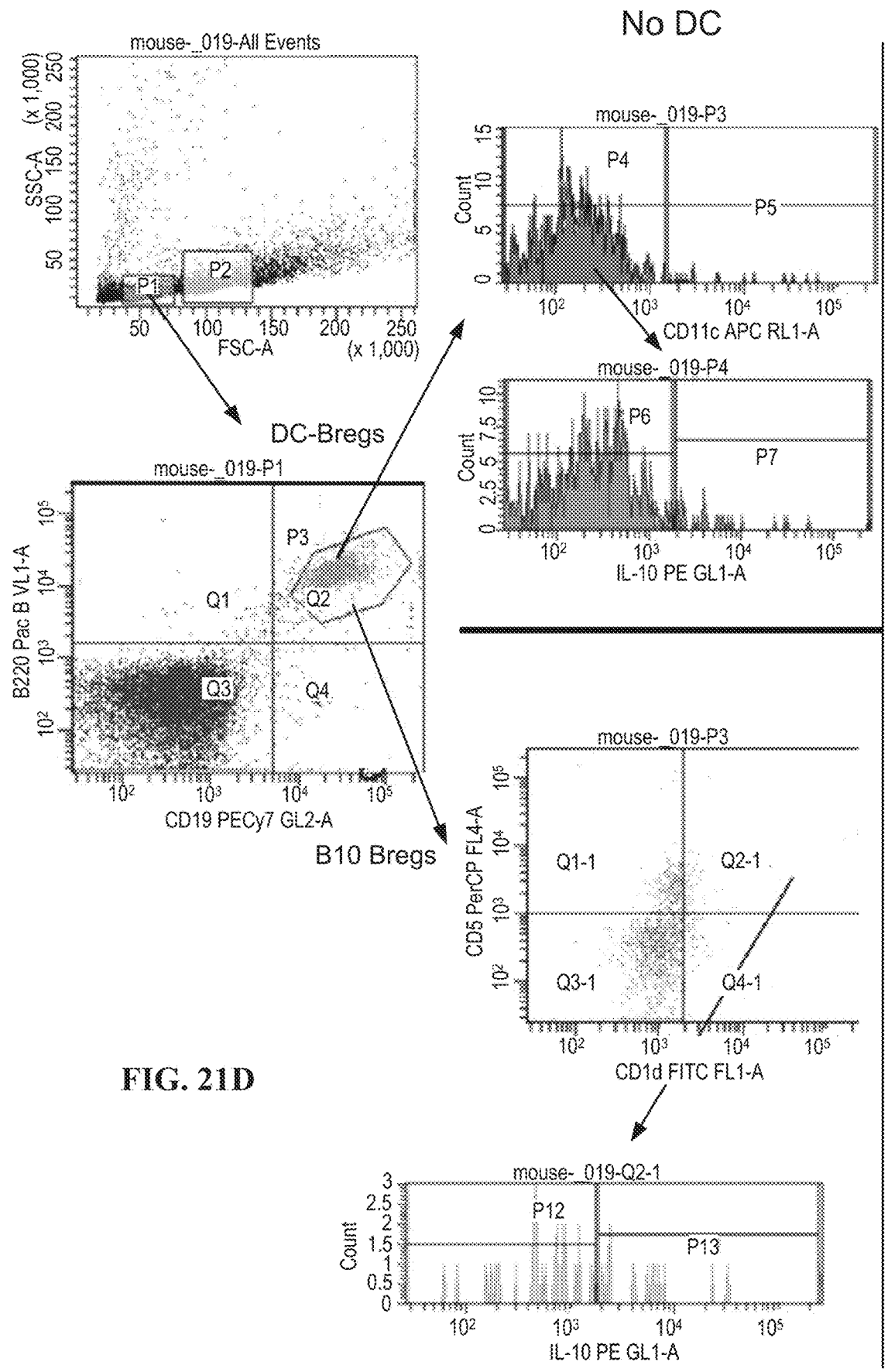
FIGS. 21D-21F is flow cytometric data of freshly-collected pancreatic lymph node cells.

A graphic summary of the absolute number of DC-Bregs measured by flow cytometry in the freshly-collected spleens of the untreated, cDC and iDC-injected NOD mice was shown in FIG. 21D. The bars represented the medians and the error bars represented the standard deviation. The differences among the medians was statistically-significant (Kruskal-Wallis test of variance).

Figure 21E:
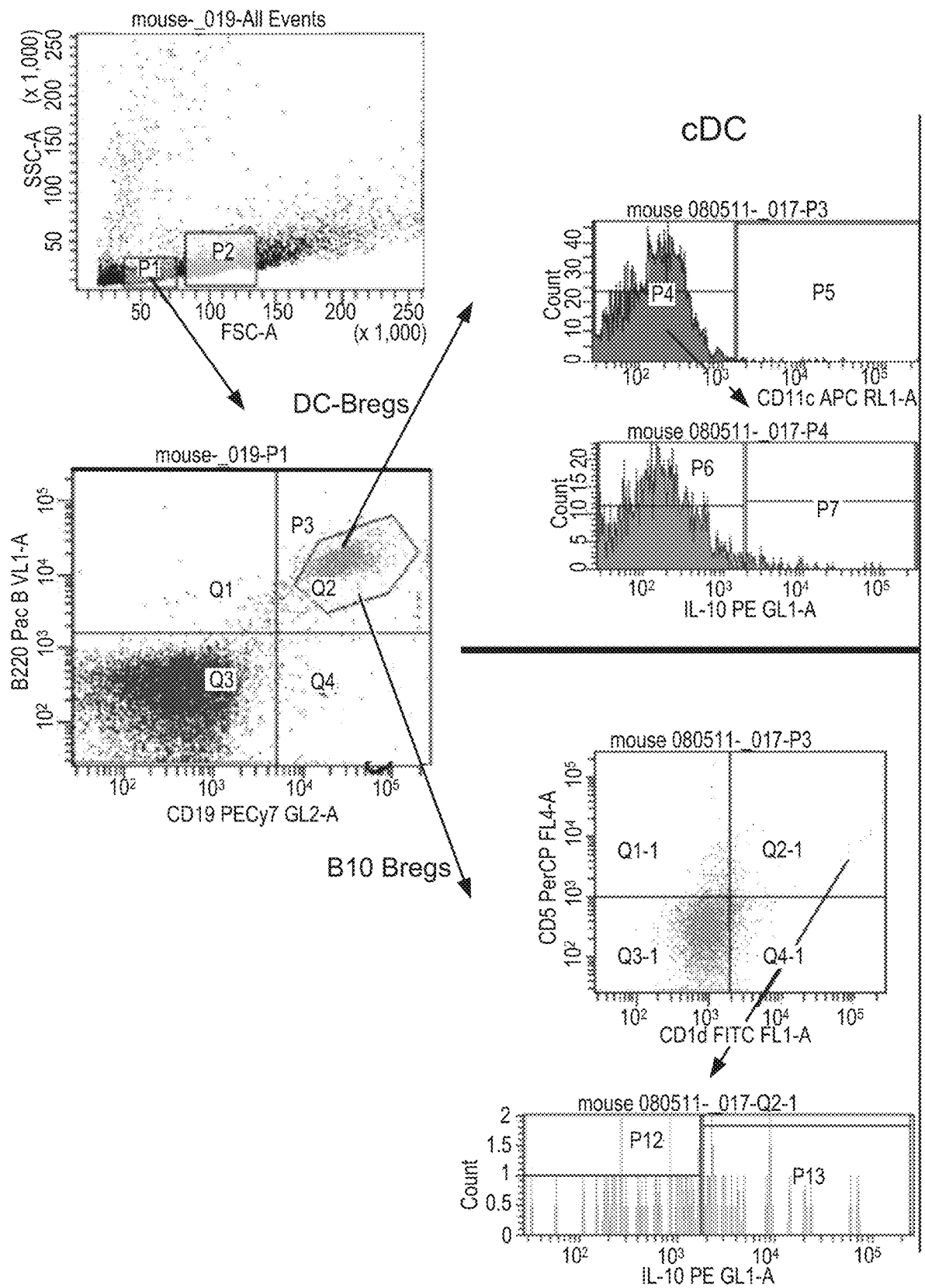

A graphic summary of the frequency of B10 Bregs (CD19+ CD1 d+ CD5+ Il-10+ cells) was measured by flow cytometry as a % of total splenocytes as shown in FIG. 21E. The number of mice from which tissue was collected per treatment type was shown at the top of the bars which represent the median value. The error bars reflected the standard deviation. The differences between iDC and cDC/control untreated were statistically-significant (p<0.05, Kruskal-Wallis test of variance).

Figure 21F:
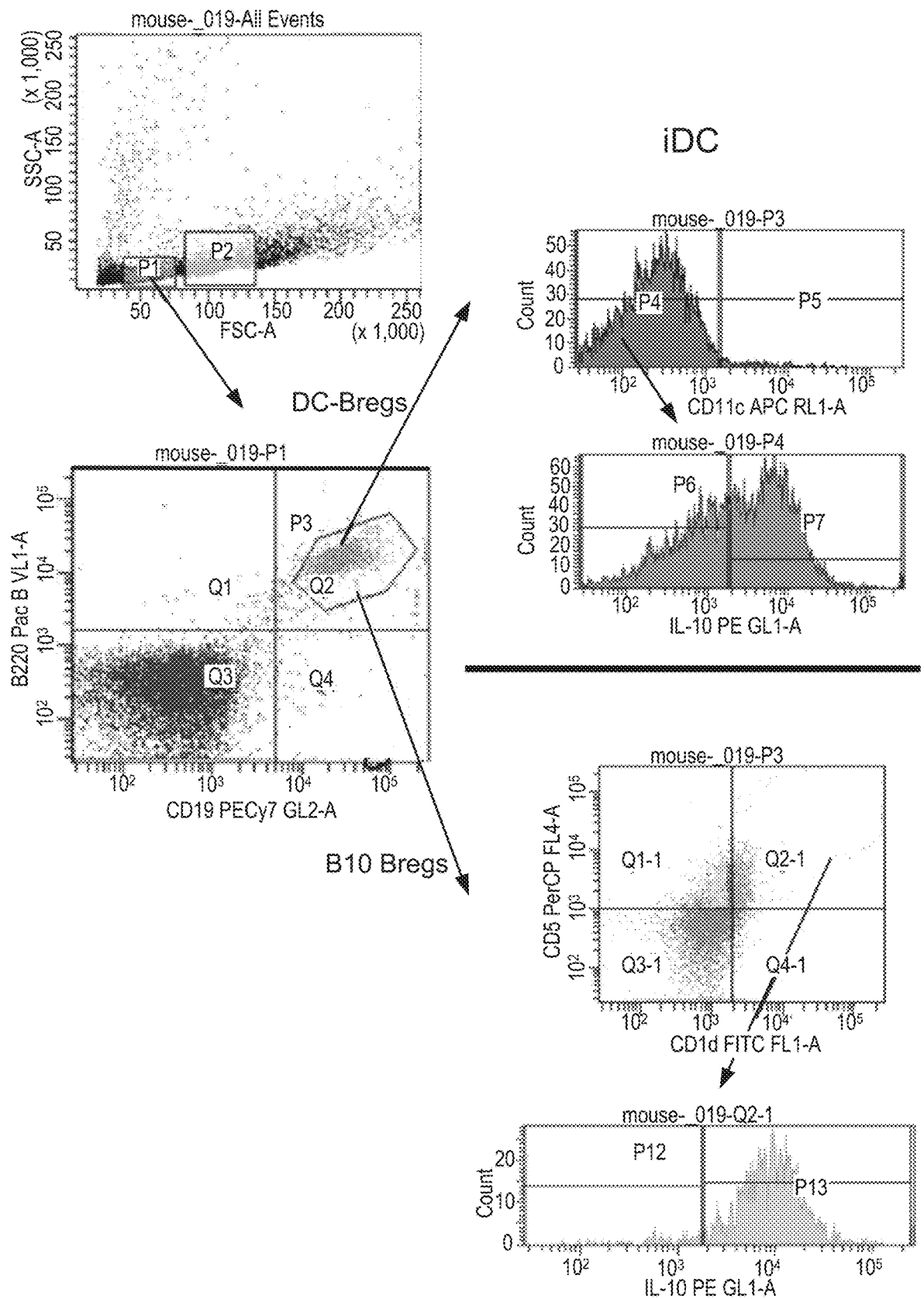

A graphic summary of the absolute number of B10 Bregs measured by flow cytometry in the freshly-collected spleens of the untreated, cDC and iDC-injected NOD mice was shown in FIG. 21F. The bars represented the medians and the error bars represented the standard deviation. The differences among the medians was statistically-significant (p<0.005, Kruskal-Wallis test of variance).

Figure 21G:
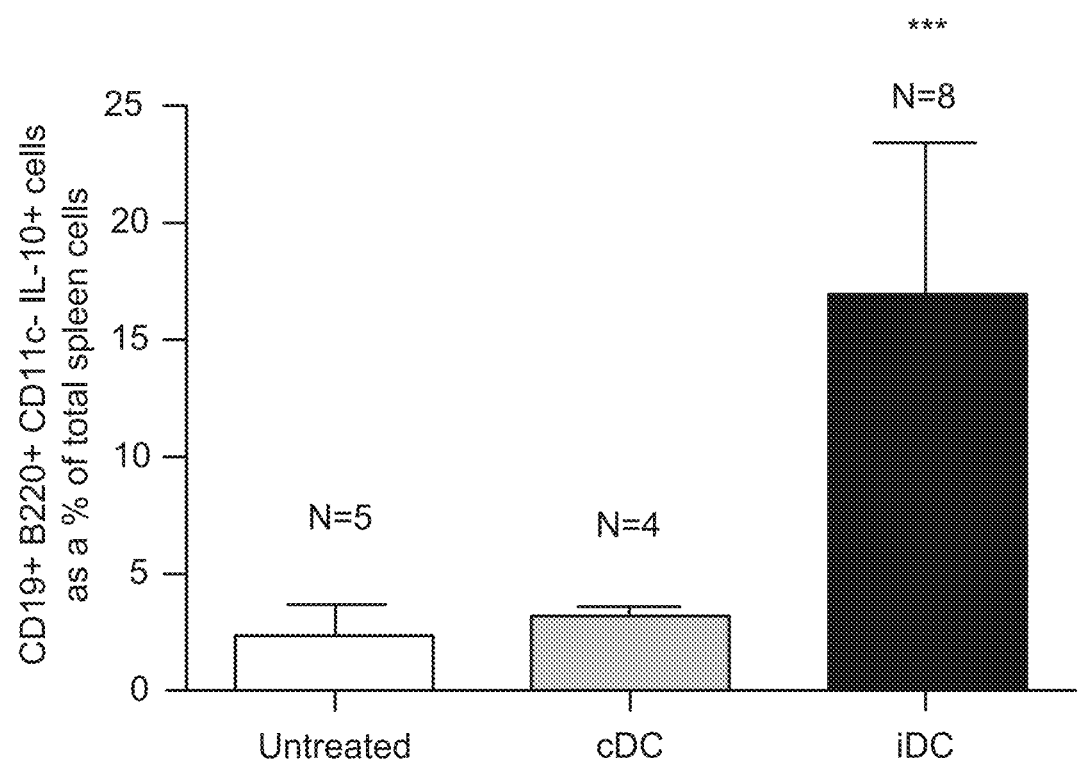
FIG. 21G is a graph summarizing the frequency of DC-Bregs by flow cytometry as a % of total splenocytes.
Figure 21H:
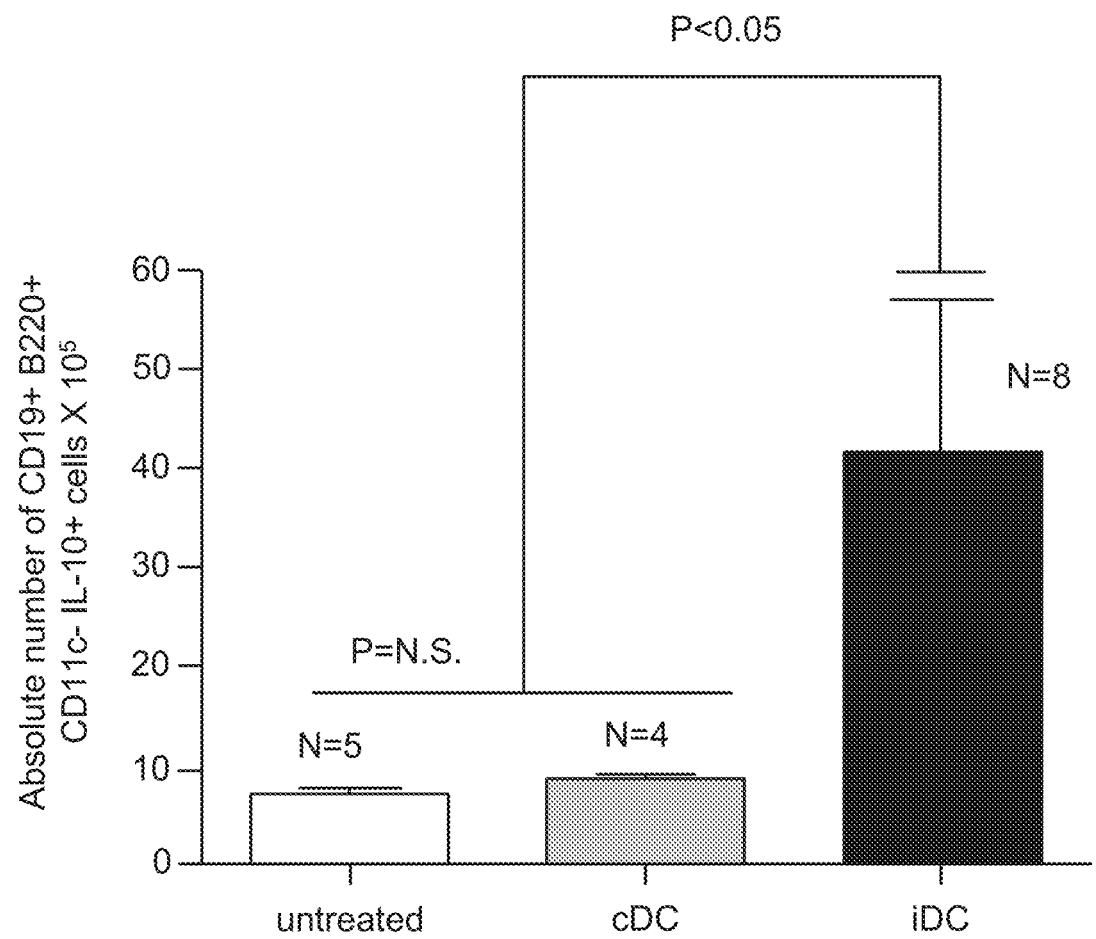
FIG. 21H is a graph summarizing the absolute number of DC-Bregs measured by flow cytometry in spleens of untreated, control dendritic cells (cDC) and iDC-injected mice.
Figure 21I:
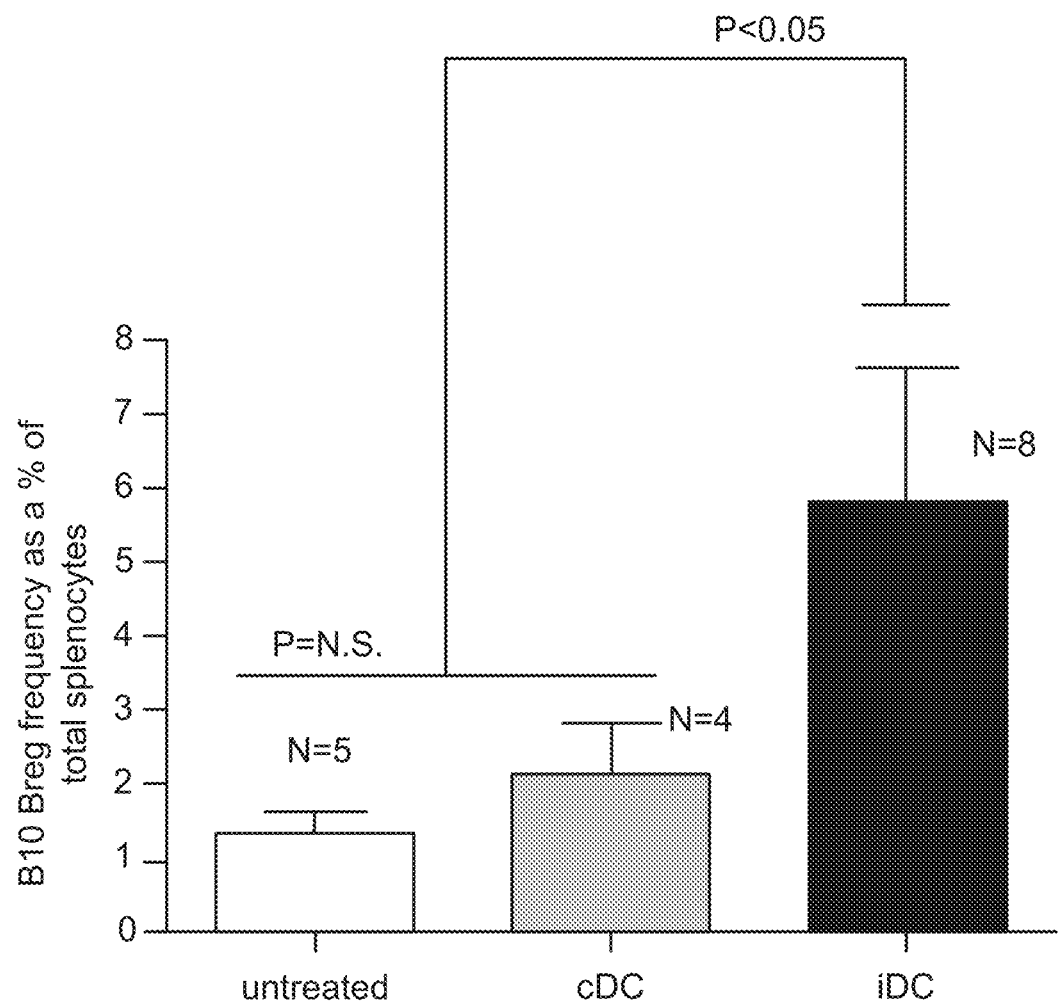
FIG. 21I is a graph summarizing the frequency of B10 Bregs measured by flow cytometry as a % of total splenocytes.
Figure 21J:
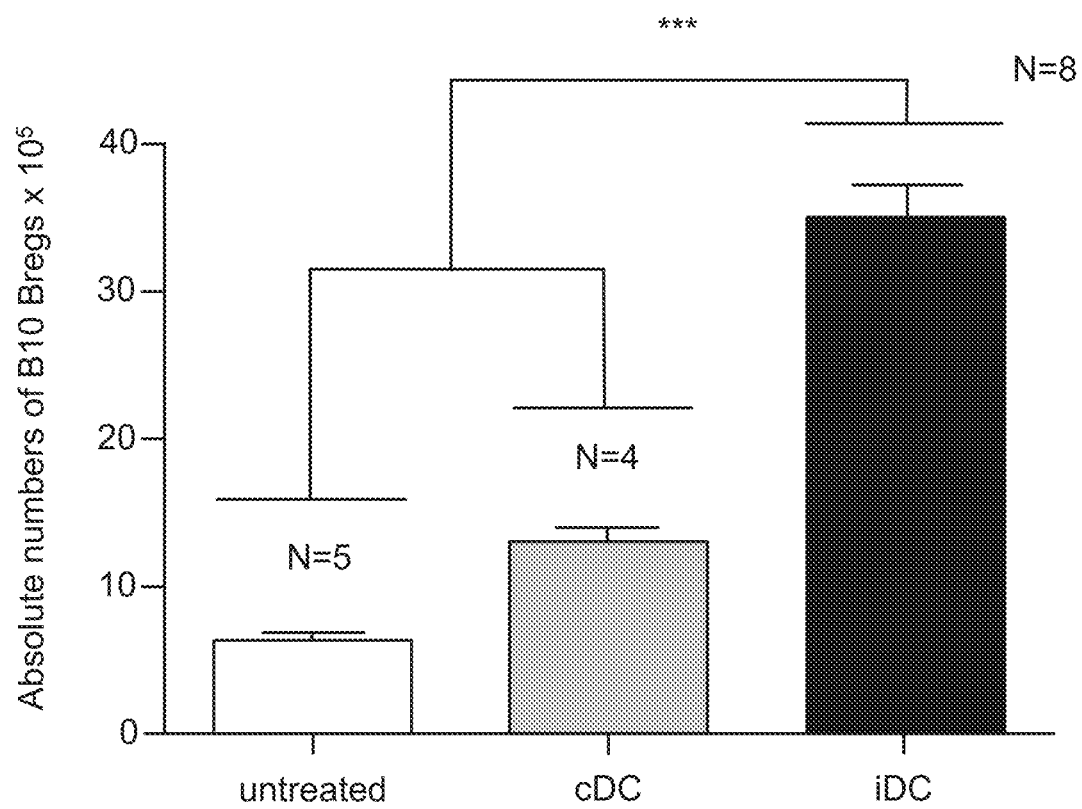
FIG. 21J is a graph summarizing the absolute number of B10 Bregs measured by flow cytometry in spleens of the untreated, cDC and iDC-injected mice.
Figure 21K:
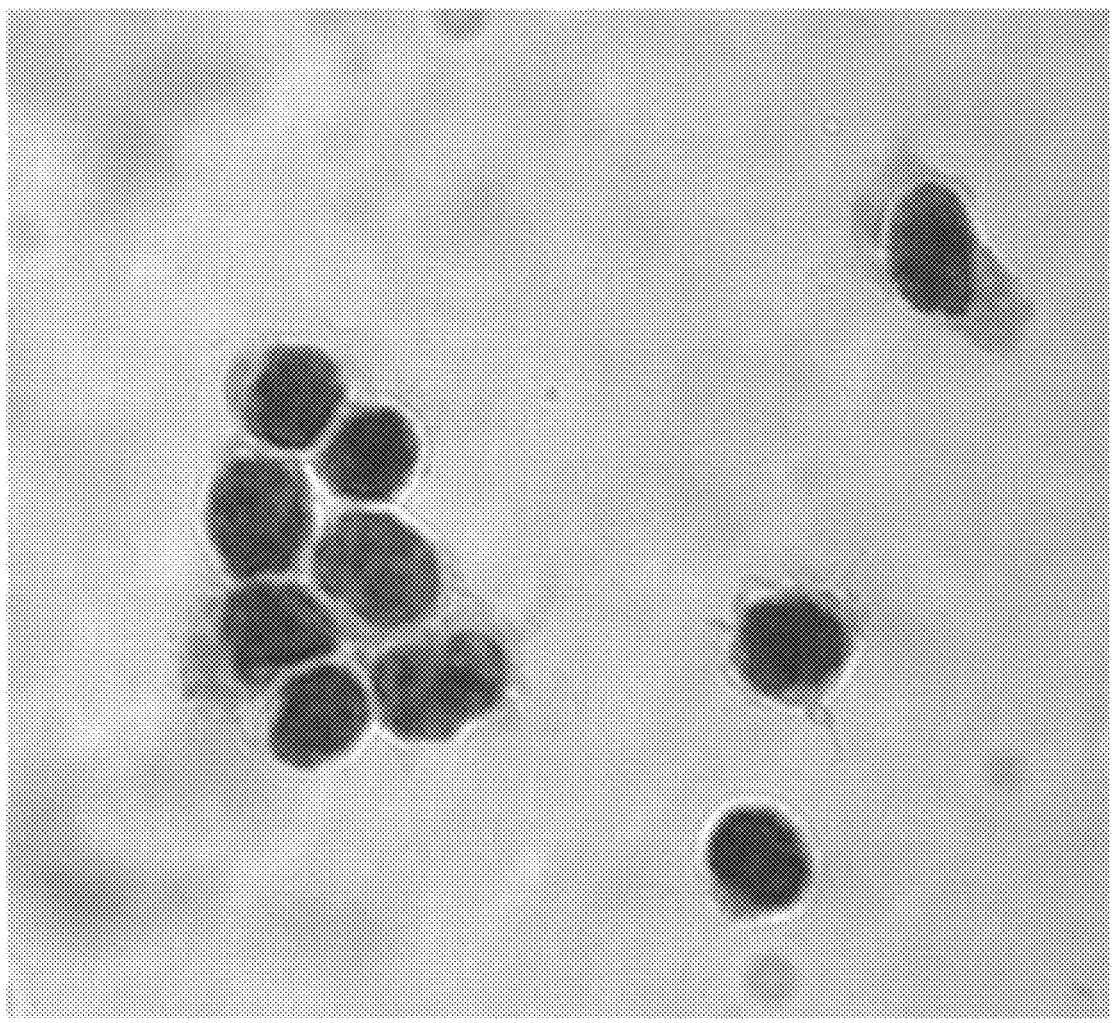
FIG. 21K is a microscopy image of hematoxylin/eosin-stained B10 Bregs.

Hematoxylin/Eosin-stained cytospin of B10 Bregs sorted from freshly-isolated splenocytes of a 10 week-old female non-diabetic NOD mouse was shown in FIG. 21G. The morphology was identical among cytospins from another 5 age-matched female NOD mice.

Example 12

Figure 22A:
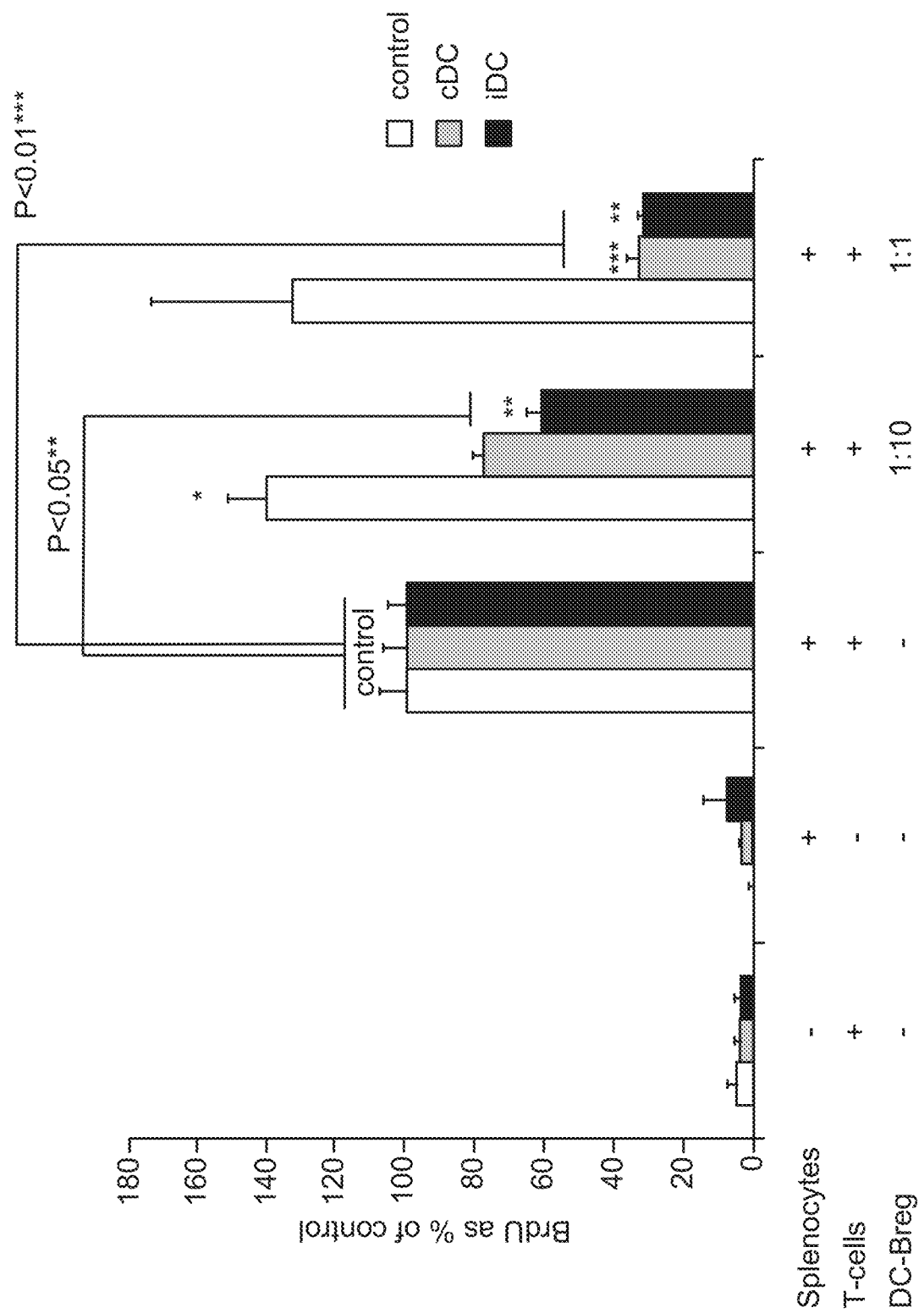
FIG. 22A is a graph summarizing the frequency of BrdU-positive T-cells co-cultured in the absence or presence of suppressive B-cell populations.

Suppressive B-Cells are Functionally-Suppressive in Allogeneic Mixed-Lymphocyte-Reactions In Vitro Quintuplicate wells of splenic T-cells, irradiated splenocytes (alone, together, or in the presence of CD19+ B220+ CD11c– IL-10+ B-cells) were incubated for 5 days, FIG. 22A. On the last day, BrdU was added. The number of BrdU+ cells was measured by flow cytometry on day 6. Cultures consisted of 1×10$^5$ T-cells from the spleen of NOD female mice (8 weeks), irradiated allogeneic splenocytes (C57BL/6 males, 8 weeks) and purified B220+CD19+ CD11c– IL-10+ B-cells. Proliferation of only T-cells or splenocytes was taken to represent 100% proliferation in these analyses. The bars represented the mean of n=5 wells and the error bars represented the SEM. The differences in proliferation in co-cultures of CD19+ B220+ CD11c– IL-10+ B-cells in the absence of cDC or iDC compared to those in the presence of the DC were statistically-significant (p values shown in graph on top of bars as single, double (p<0.05, ANOVA) or triple asterisks (p<0.01, ANOVA). The last two sets of bars compared the proliferation of the T-cells at a 1:10 and a 1:1 ratio of DC-Breg:T-cell numbers.

Figure 22B:
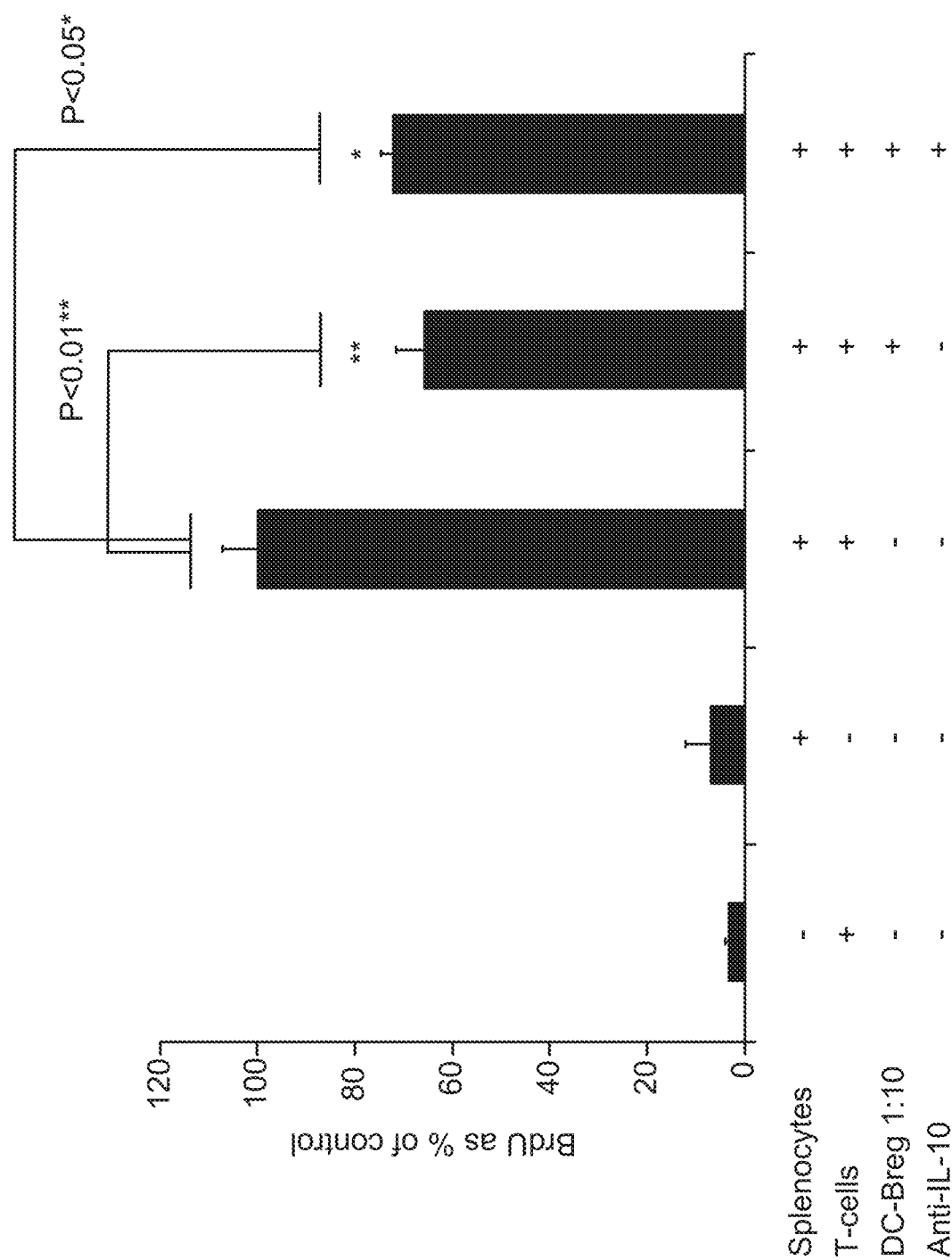
FIG. 22B is a graph summarizing the frequency of BrdU-positive T-cells co-cultured in allogeneic mixed-lymphocyte-reactions (MLR) with suppressive B-cell populations, with and without neutralizing IL-10 antibody.

Quintuplicate wells of splenic T-cells, irradiated splenocytes (alone, together, or in the presence of DC-Bregs) were incubated for 5 days, FIG. 22B. The ratio of DC-Breg:T-cell numbers was 1:10 in all co-cultures. On the last day, BrdU was added. Anti-IL-10 antibody was added at 1 µg/mL where shown. Proliferation of T-cells in the presence of irradiated splenocytes was taken to represent 100% proliferation. The bars represented the means of BrdU+ cells as a % of BrdU+ in the control T-cells:splenocyte co-cultures (n=5 wells) and the error bars represented the SEM. The differences in T-cell proliferation in co-cultures in the absence of DC-Bregs and those in the presence of DC were statistically-significant (p values shown in graph, ANOVA).

Figure 22C:
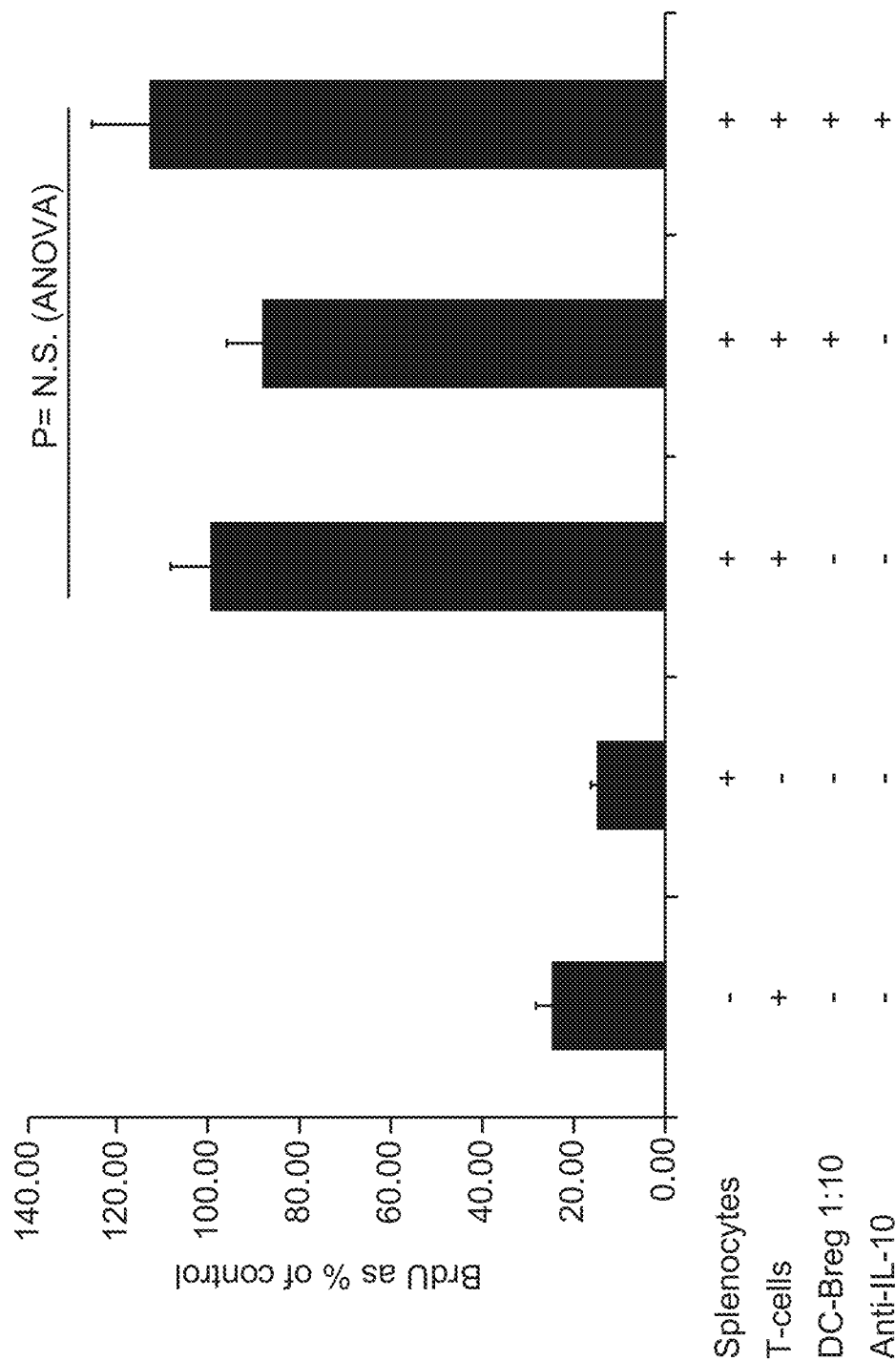
FIG. 22C is a graph summarizing the frequency of BrdU-positive T-cells co-cultured in allogeneic MLR with suppressive B-cell populations physically separated by a Transwell insert.

Mixed-lymphocyte reactions were conducted with DC-Bregs added on top of a Transwell insert separating co-cultures of T-cells and allogeneic irradiated splenocytes, FIG. 22C. The ratio of DC-Breg:T-cell numbers was 1:10 in all co-cultures. Anti-IL-10 antibody is added at 1 µg/mL where shown on top of the Transwell insert (with the DC-Bregs). Proliferation of cells in the bottom of the dish (T-cells:splenocyte co-cultures) in the absence of DC-Bregs was taken to represent 100% proliferation in these analyses. N.S.=differences among means were not significant (p>0.05).

Example 13

Tolerogenic DCs Promote Proliferation of Suppressive B-Cells

Figure 23A:
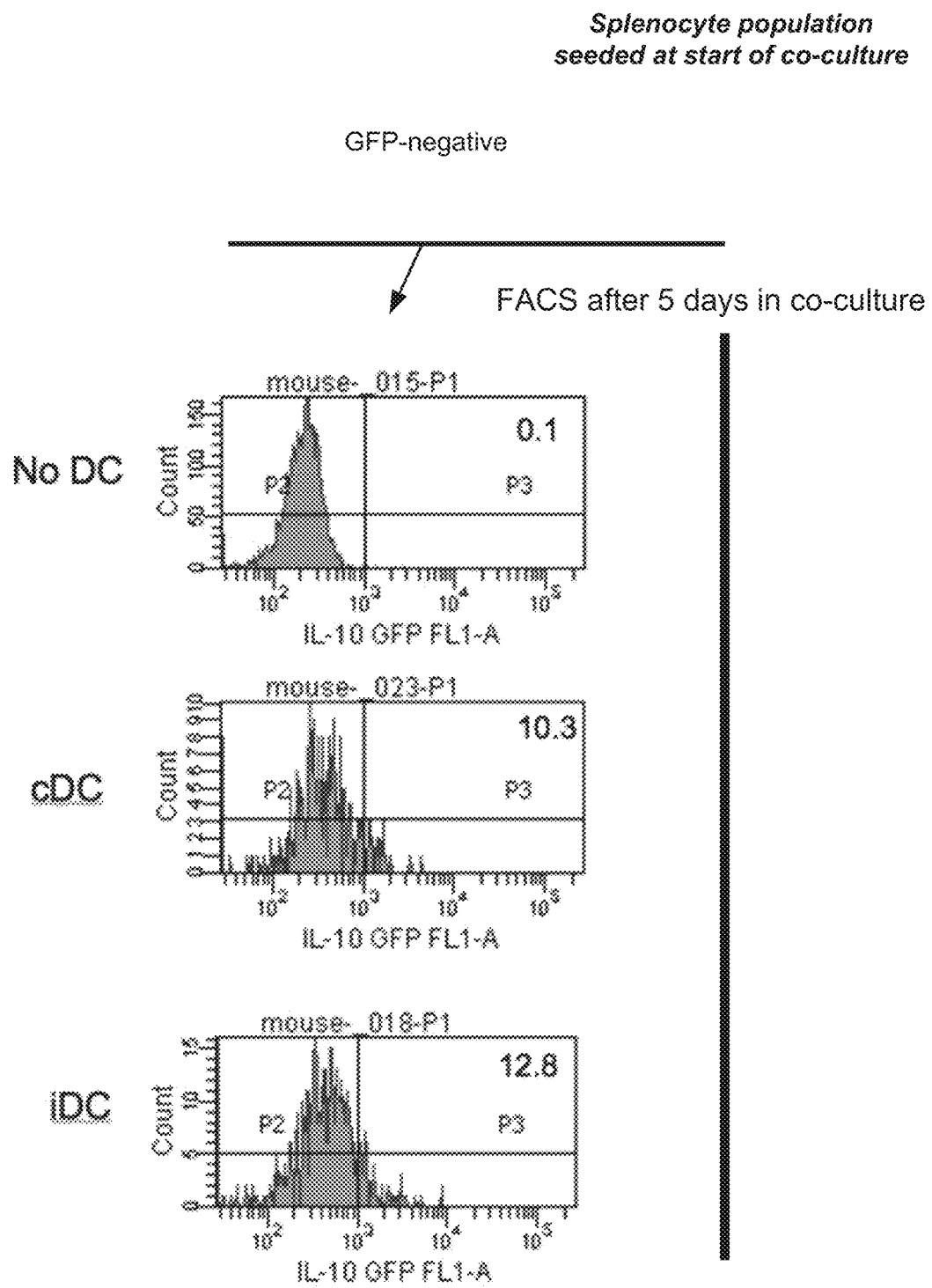

Freshly-collected splenocytes from IL10$^{gfp}$ transgenic mice were flow sorted into CD19+B220+ CD11c– GFP+ or CD19+ B220+ CD11c– GFP-populations with very stringent gating to exclude autofluorescent cells based on the fluorescence characteristics of flow-sorted CD19+B220+ CD11c– cells from freshly-collected splenocytes of the wild-type mouse strain (far right panel inset), FIG. 23A. Purity of the GFP+ after sorting (indicated as IL-10 versus FSC in the top most quadrant plot) as well as cell viability (Live/Dead staining in the histogram adjacent to the top most quadrant plot), representative of all the sorting outcomes performed in this experiment was shown, 5×10$^4$ sorted cells (GFP+ or GFP–) were placed into co-culture with PBS, or an equal number of cDC or iDC. Representative GFP fluorescence of the B-cells after 5 days in co-culture with cDC, iDC and media was shown in the histograms with the GFP+ cells represented as a % of total cells in culture (values of this specific experiment, representative of three separately-conducted experiments, are shown inside the histograms).

Figure 23B:
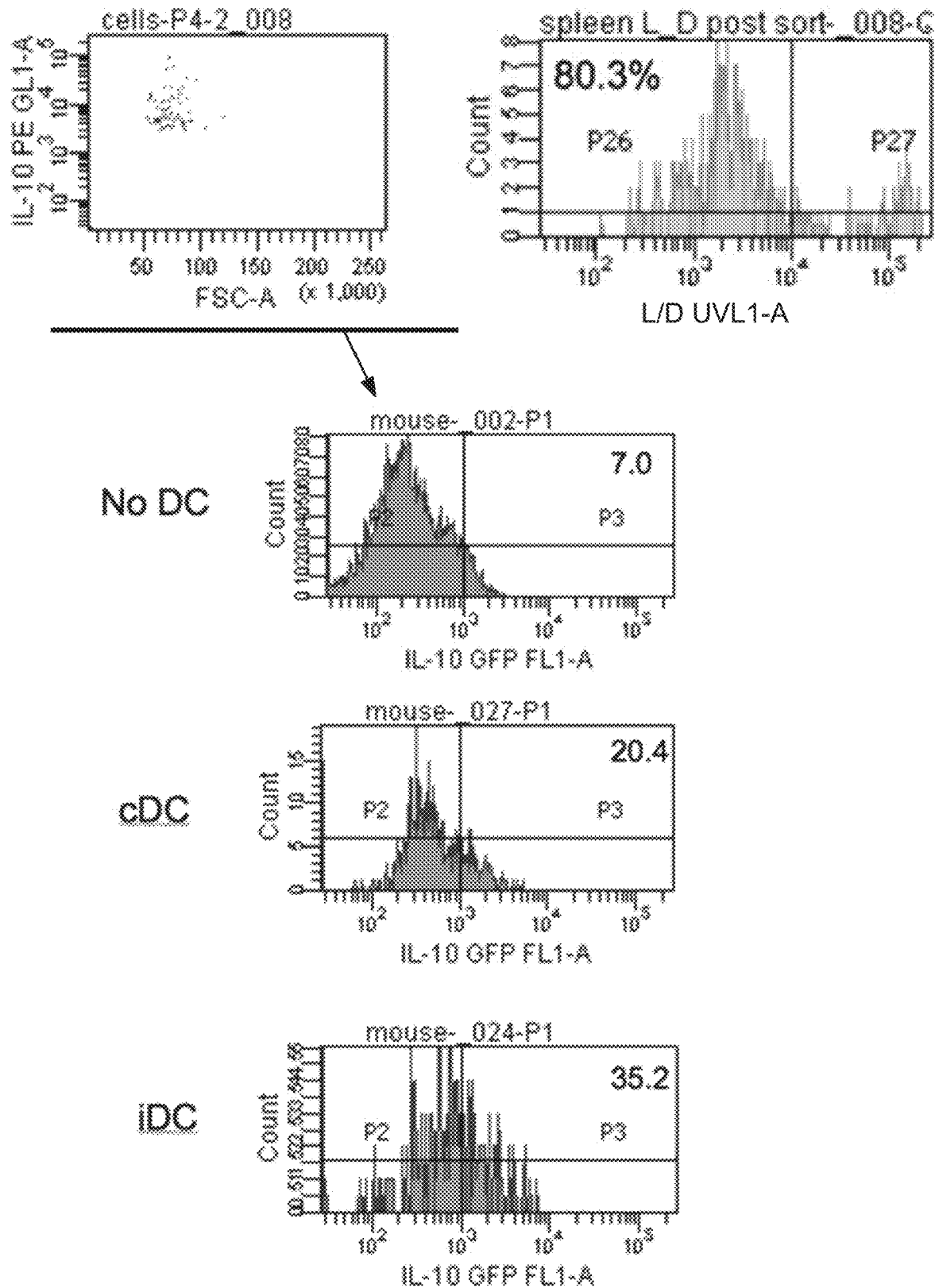
Figure 23D:
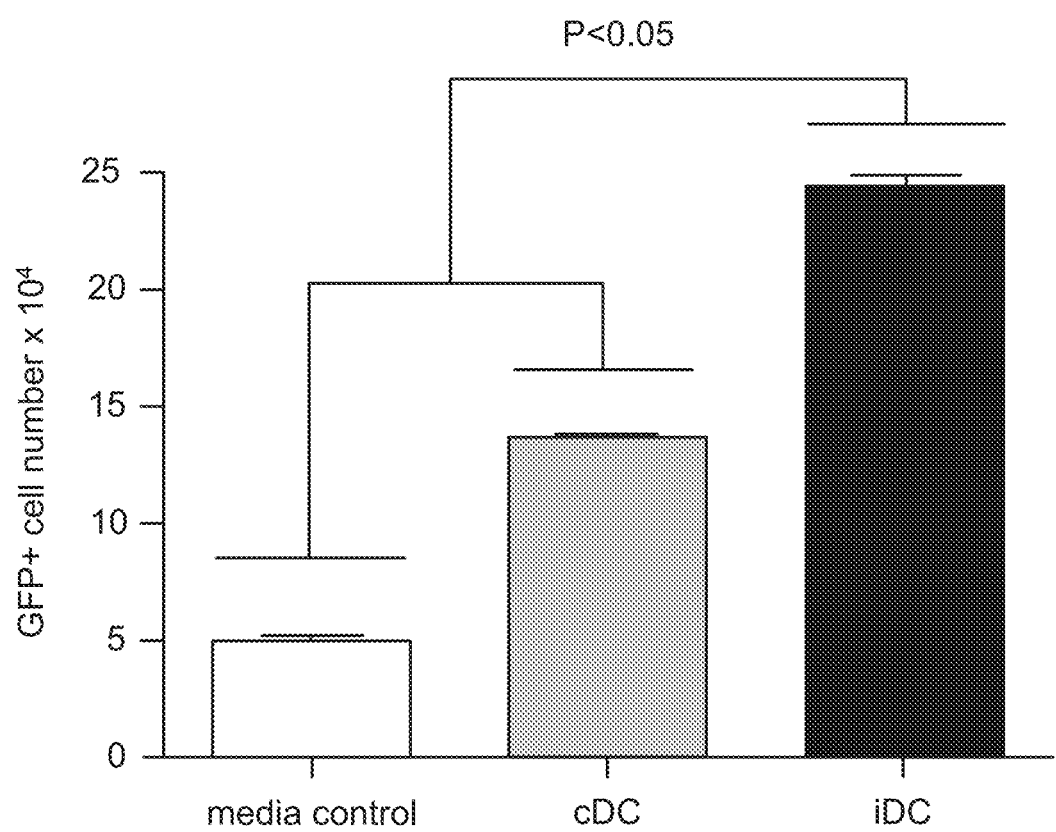
FIG. 23D is a graph summarizing the actual number of GFP+ DC-Bregs in vitro after co-culture of a highly-purified GFP− starting population with media, cDC, or iDC.
Figure 23E:
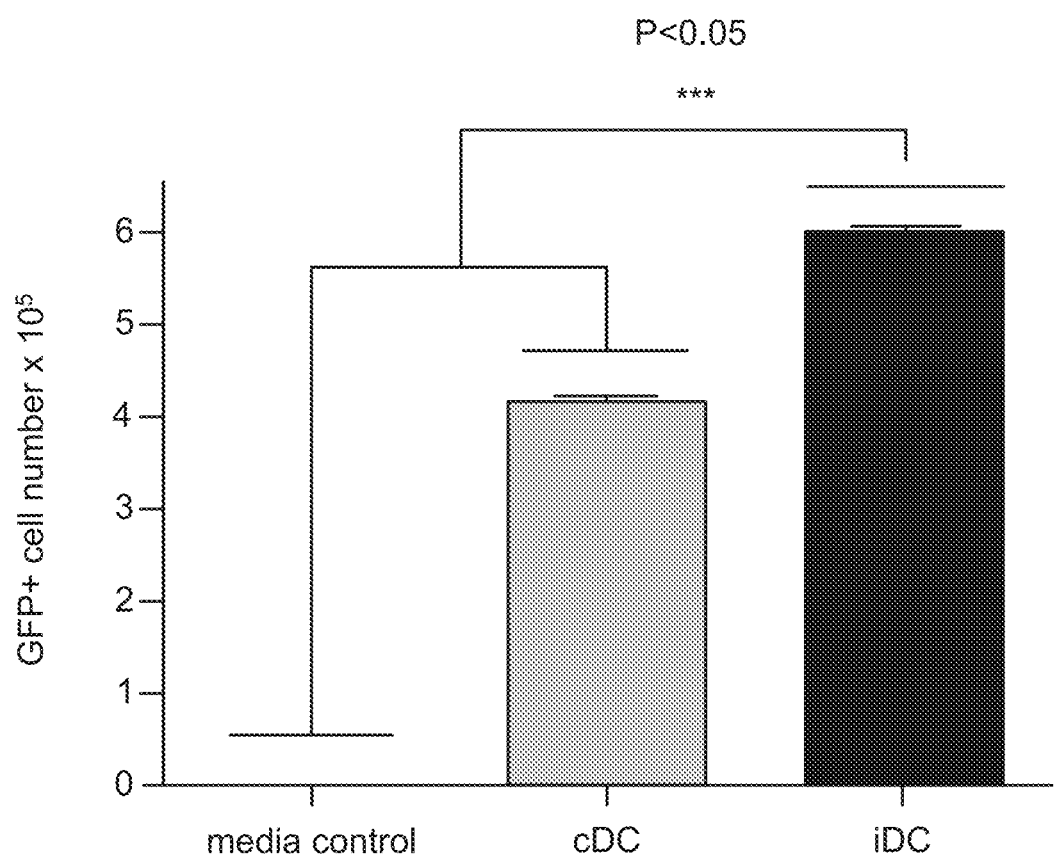
FIG. 23E is a graph summarizing the actual number of GFP+DC-Bregs in vitro after co-culture of a highly-purified GFP+ starting population with media, cDC, or iDC.

A graphic summary showed the actual number of GFP+ DC-Bregs in vitro after co-culture of a highly-purified GFP– starting population (5×10$^4$ cells) with media, cDC or iDC, FIG. 23B. The bars indicated the mean of triplicate wells and the error bars the SEM. p<0.05 shown by asterisk (ANOVA).

A graphic summary showed the actual number of GFP+ DC-Bregs in vitro after co-culture of a highly-purified GFP+ starting population (5×10$^4$ cells) with media, cDC or iDC, FIG. 23C. The bars indicated the mean of triplicate wells and the error bars the SEM. p<0.05 shown by asterisk (ANOVA).

Example 14

Surface Marker Characterization of Suppressive B-Cells

Figure 24A:
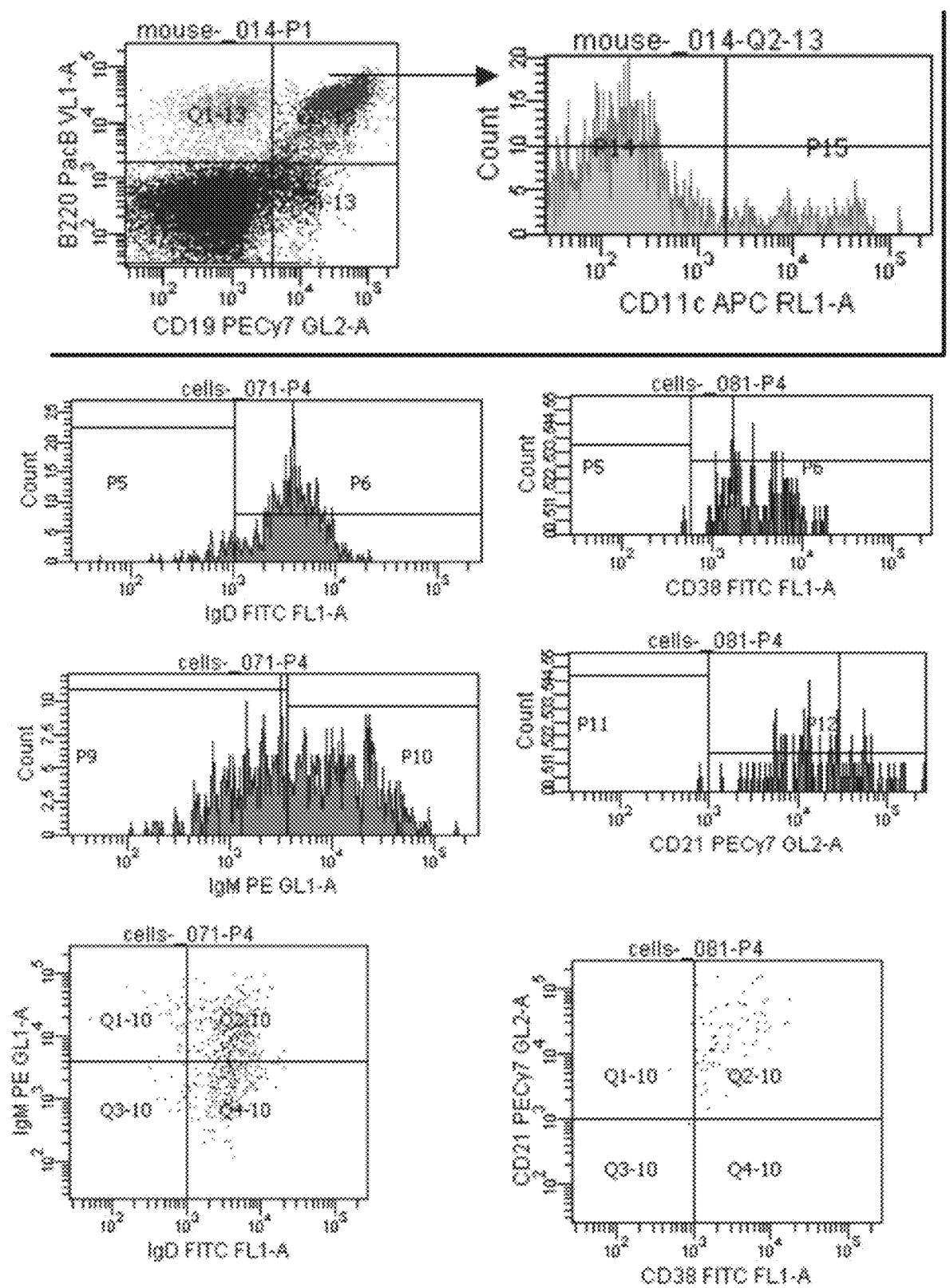
FIGS. 24A-24B is flow cytometric data of splenic DC-Bregs from non-obese diabetic (NOD) mice.
Figure 24B:
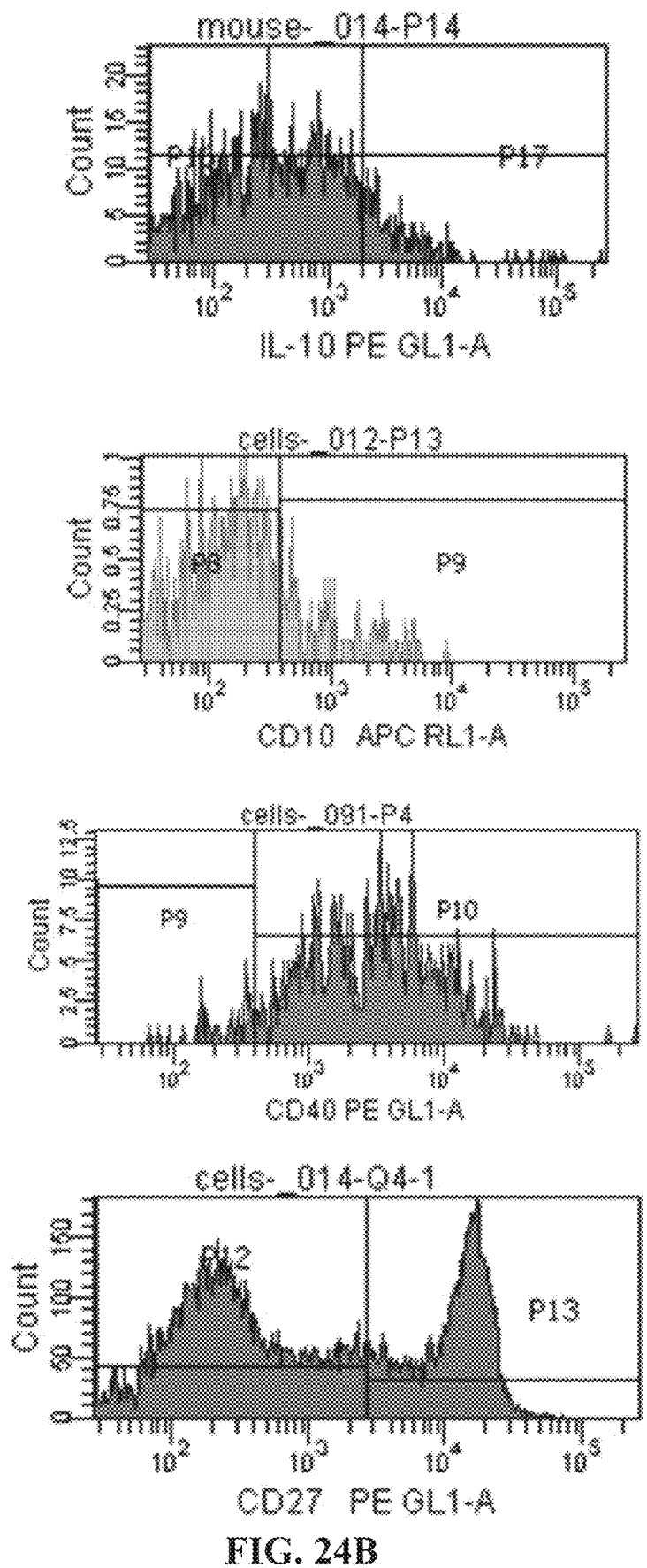

Gating was established as shown (CD19+ B220+ CD11c–), FIG. 24. The frequency of cells expressing each of the surface proteins indicated in the histograms inside this gate further established the phenotype of the DC-Bregs in freshly-isolated spleen of NOD female mice (10 weeks of age). The data shown were representative of the flow cytometry analyses of freshly-acquired splenocytes from three different age-matched NOD mice. Surface markers included IgD, IgM, CD10, CD21, CD27, CD38 and CD40.

Example 15

Suppressive B-Cells in Allogeneic Mixed Lymphocyte Reaction (MLR) In Vitro

Figure 25:
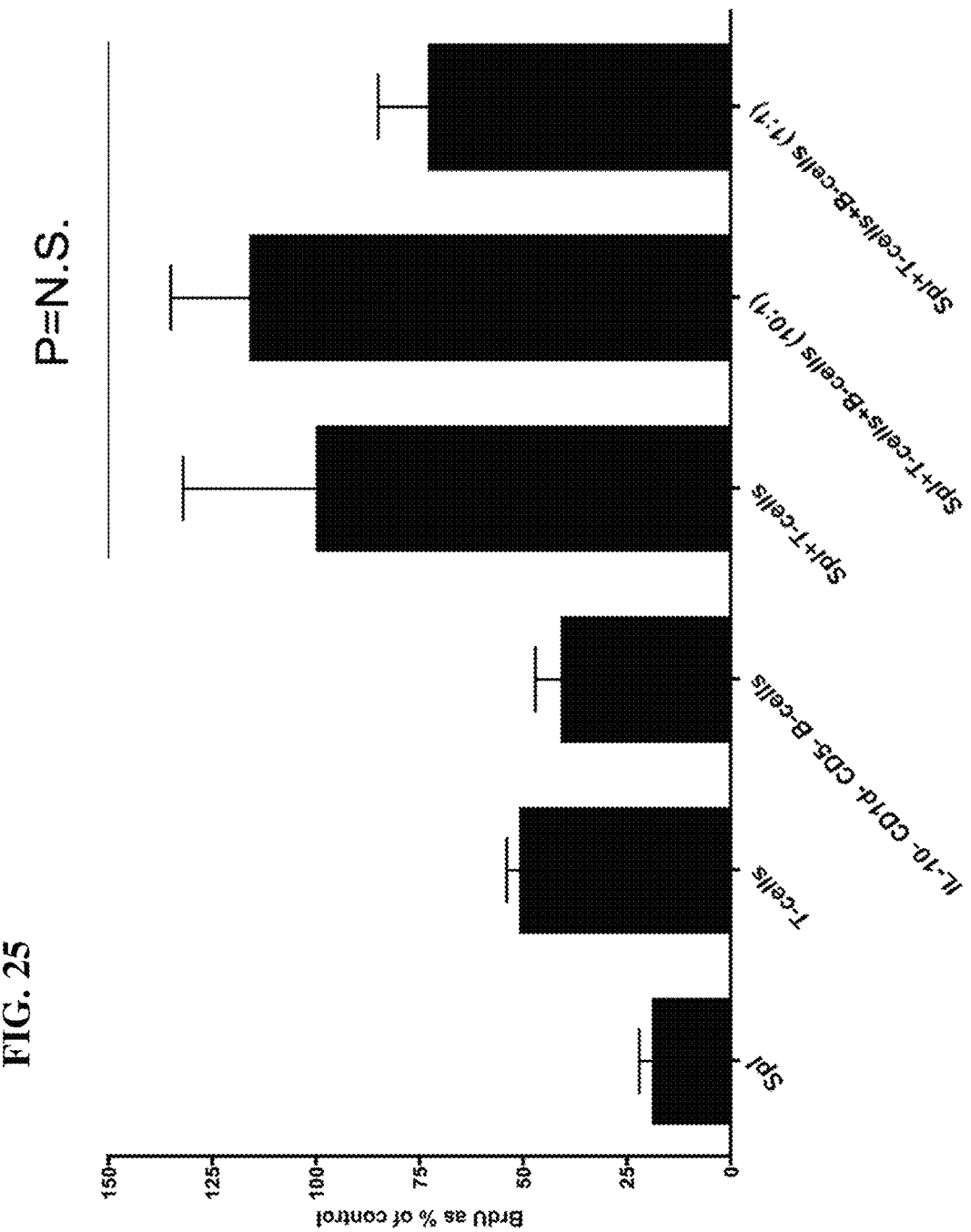
FIG. 25 is a graph summarizing the frequency of BrdU-positive T-cells in the presence or absence of syngeneic B-cells and allogeneic splenocytes, measured by flow cytometry.

The frequency of BrdU+ T-cells was measured by flow cytometry, FIG. 25. Specifically, IL10$^{gfp}$ T-cells freshly isolated from the spleens of IL10$^{gfp}$ transgenic mice were cultured in the presence or absence of syngeneic CD1 d, CD5, IL-10-depleted B-cells (represented in the graph as "IL-10-CD1 d-CD5– B-cells") and allogeneic, irradiated splenocytes (Spl). The data are shown as BrdU+ T-cells as a % control, where control refers to the frequency of proliferation of T-cells in the presence of only irradiated allogeneic splenocytes (taken to be 100%). The B-cells were added at a 1:1 or a 1:10 ratio of B-cells:T-cells. The bars represent the mean and the error bars the SEM. The differences in proliferation of T-cells among the co-cultures were not statistically-significant (p=0.11$^8$, ANOVA).

Example 16

Suppressive B-Cells Express Retinoic Acid (RA) Receptors

Figure 26A:
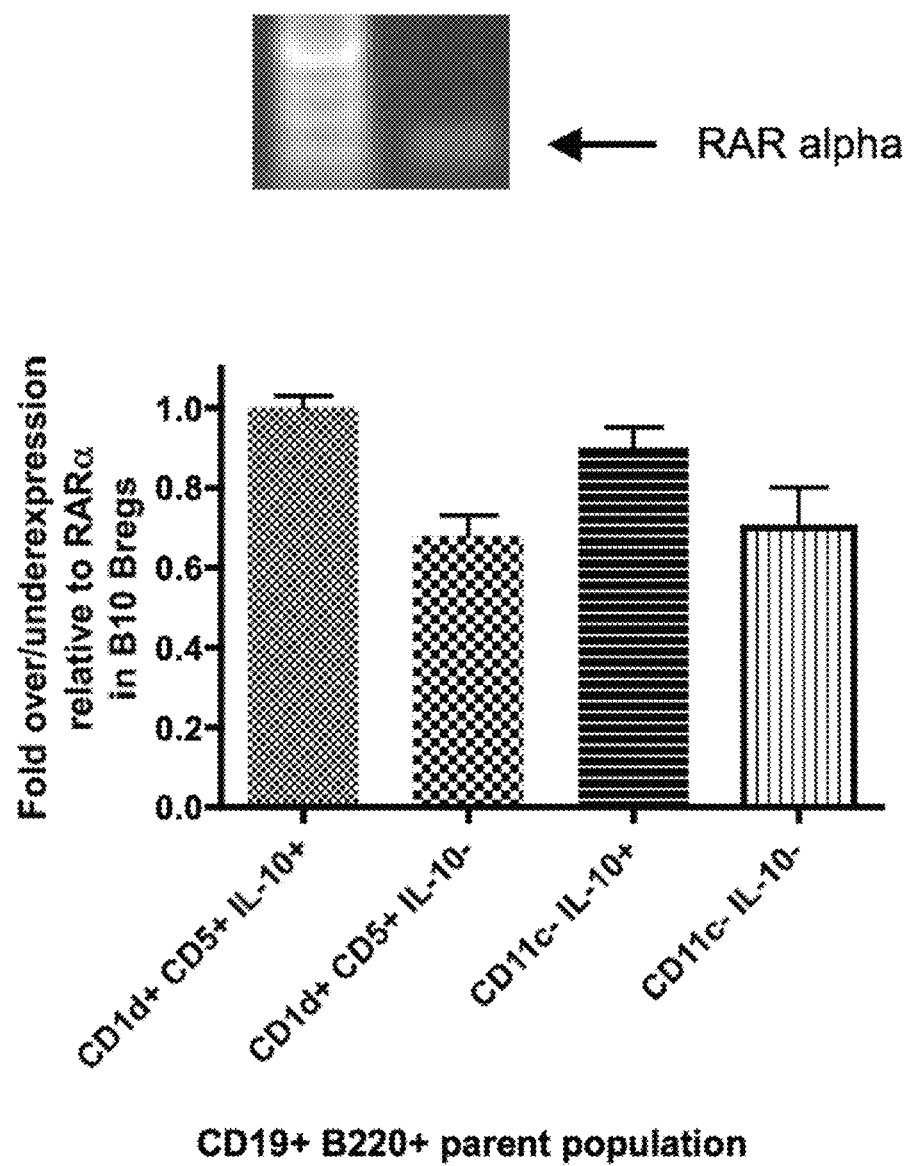
FIG. 26A is a graph summarizing the expression of retinoic acid receptors (RAR alpha) relative to expression in B10 Bregs.
Figure 26B:
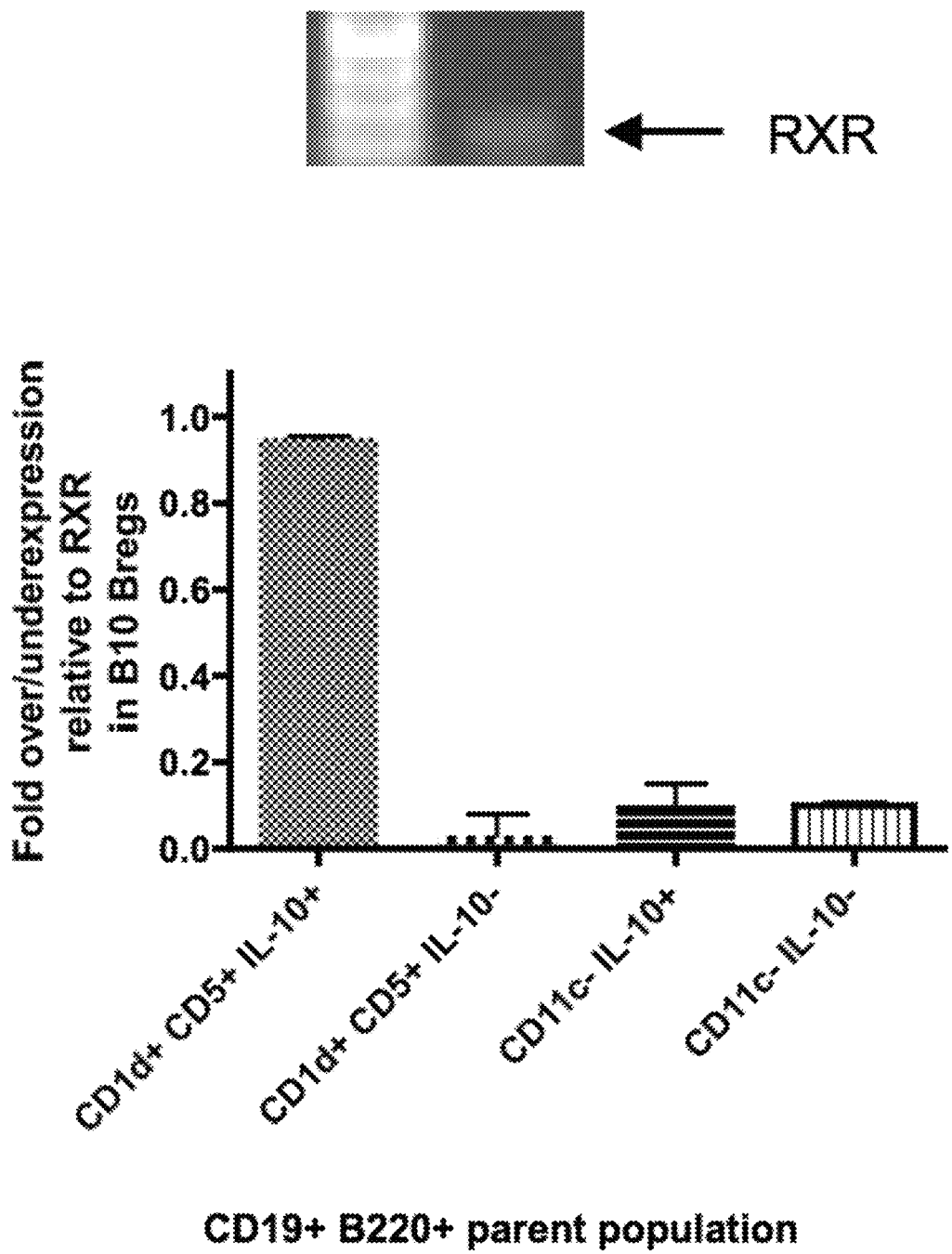
FIG. 26B is a graph summarizing expression of retinoid X receptors (RXRs) relative to expression in B10 Bregs.

Real-time, semi-quantitative RT-PCR confirmed the presence of steady-state mRNA of RA receptor alpha (FIG. 26A) as well as low levels of retinoid X receptor (FIG. 26B) in highly-purified (flow-sorted) DC-Bregs and B10 Bregs from freshly-isolated spleen of IL100$^{g/p}$ transgenic mice. The gel images in FIGS. 26A and 26B showed the RT-PCR products from flow-sorted B10 Bregs. The steady-state mRNA levels of RARalpha and RXR from the B10 Bregs were used as the controls and the values were taken to represent 100% receptor expression. Steady-state mRNA levels of RARalpha and RXR in non-B10 Breg populations were shown in the graphs underneath the gel images normalized to the B10 Breg value and presented as fold under or overexpression. Steady-state RARalpha mRNA was detected in B10 Bregs (first bar in graph; leftmost)), IL-10-CD19+CD5+CD1 d+ cells (second bar in graph), DC-Bregs (third bar in graph), and IL-10− DC-Bregs (last bar in graph; rightmost). The bars represented the medians and the error bars represented the standard deviation. These data were representative of steady-state mRNA from flow sorted cells from two different spleens of age-matched mice (10 week-old females).

Example 17

Dendritic Cells Produce Bioactive RA In Vitro

Figure 27A:
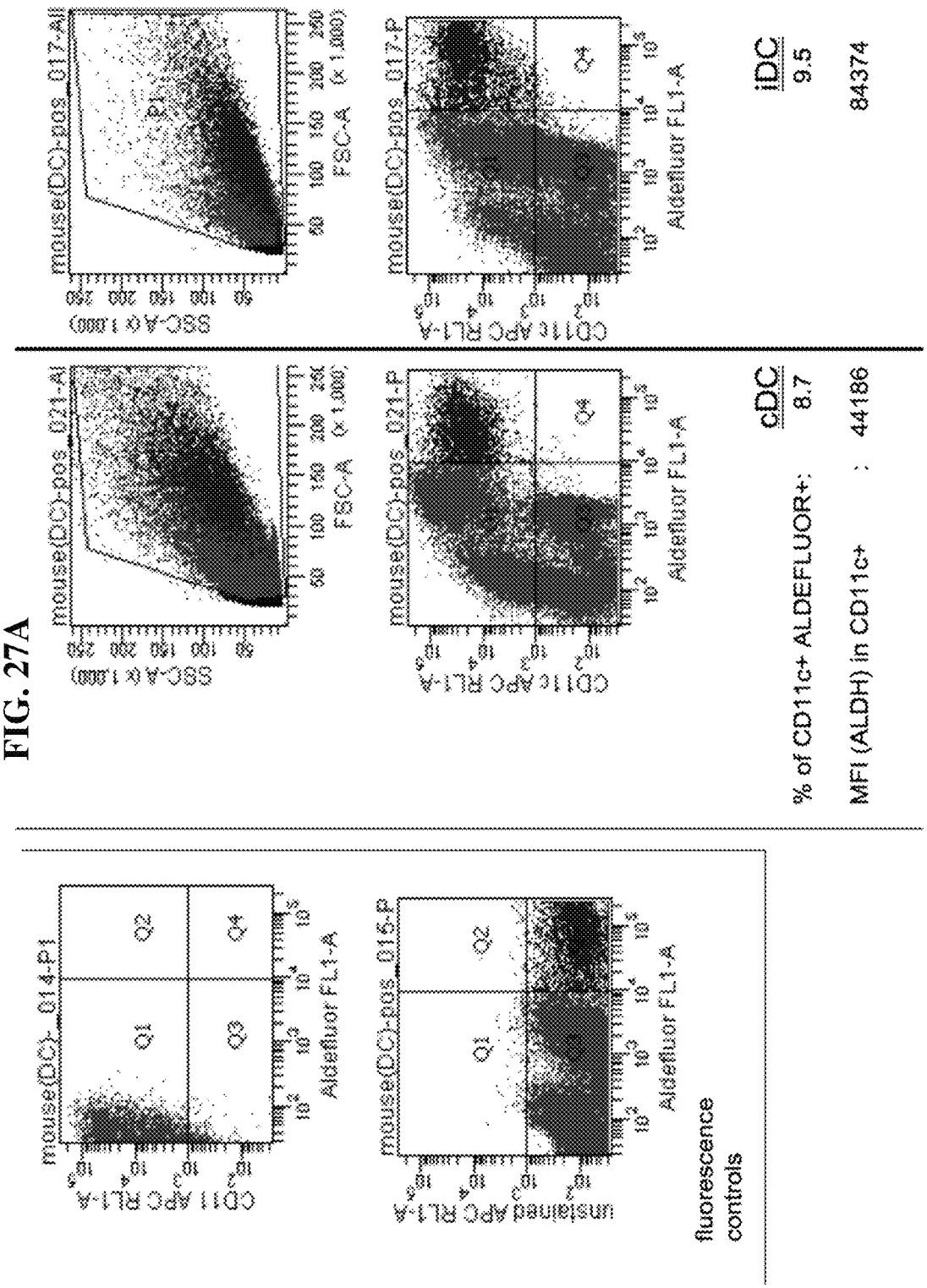
FIG. 27A is flow cytometric analysis of measuring ALDEFLUOR fluorescence of RA-producing cells, including cDC and iDC.

ALDEFLUOR reagent stains aldehyde dehydrogenase-expressing cells and thus RA-producing cells. Even though cDC are ALDEFLUOR+, and the frequency of CD11c+ ALDEFLUOR+ cDC was similar to CD11c+ ALDEFLUOR+ iDC (cDC: 8.7% cells are CD11c+ ALDEFLUOR+ compared to 9.5% of iDC), on a per-cell basis (Mean Fluorescence Intensity; MFI) iDC were twice as reactive with ALDEFLUOR than cDC (44186 compared to 84374), FIG. 27A. The flow cytometry analysis shown was representative of duplicate cultures of four age- and sex-matched NOD female mice (7 weeks of age).

Figure 27B:
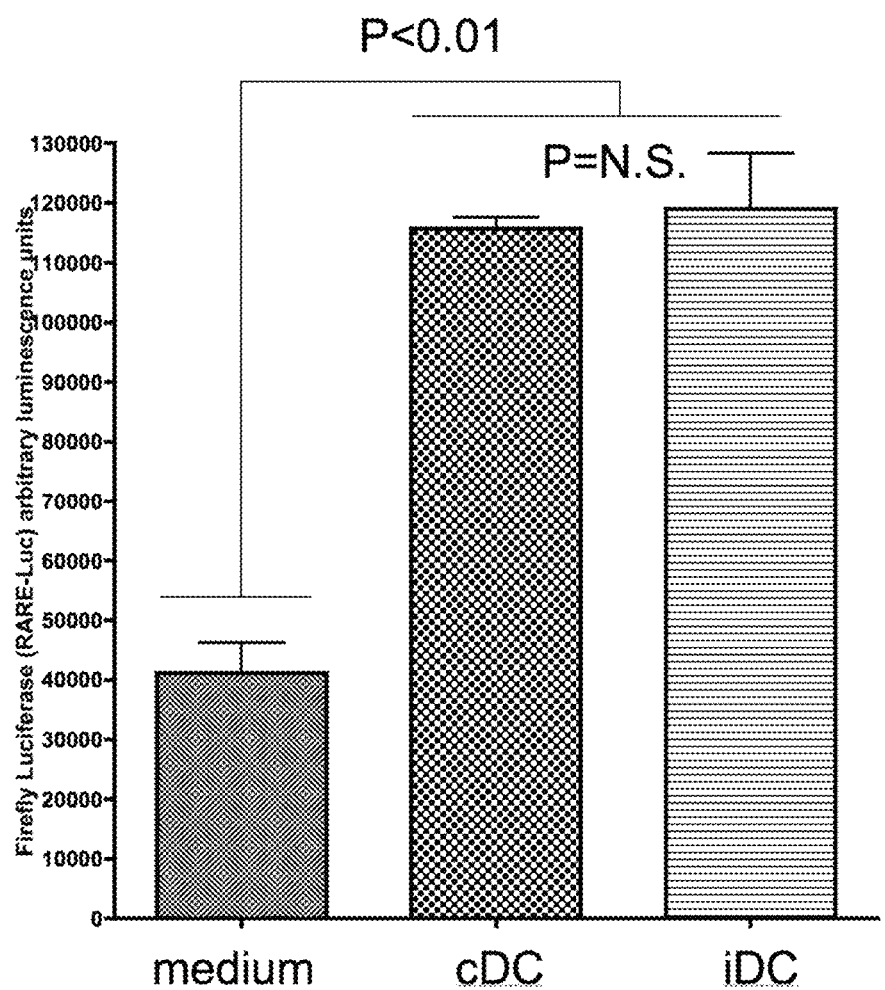
FIG. 27B is a graph summarizing luminescence detection of luciferase activity in RA-response element (RARE)-Luc plasmid-transduced HEK293 cells cultured in the presence of cDC and iDC.

RA-response element (RARE)-driven luciferase activity was detectable in RARE-Luc plasmid-transduced HEK293 cells cultured in the presence of cDC or iDC where DC were placed on top of a Transwell barrier separating them from the RARE-Luc-transduced 293 cells, FIG. 27B. Luciferase activity was measured after 24 hours culture. The bars represented the mean relative luminescence (arbitrary units) of triplicate cultures and the error bars represented the SEM. The differences between the cDC and iDC means were not significant (Student's t-test). HEK293 cells were co-transfected with a CMV-*Renilla* luciferase control plasmid concurrently with the RARE-Luc (Firefly) to control for transfection efficiency.

It will be apparent that the precise details of the methods or compositions described may be varied or modified without departing from the spirit of the described invention. We claim all such modifications and variations that fall within the scope and spirit of the claims below.

What is claimed is:

1. A method for restoration of blood glucose to a pre-diabetic level in a pediatric mammal comprising:
   administering two or more subcutaneous injections of tolerogenic dendritic cells at one or more injection sites proximal to a pancreas in said pediatric mammal,
   wherein said blood glucose is restored to said pre-diabetic level for a period of at least twenty four hours.

2. The method of claim 1, wherein said tolerogenic dendritic cells are isolated from said pediatric mammal or from a different mammal of the same species.

3. The method of claim 1, wherein one of said one or more injection sites is about 3.25 to about 2.25 inches left and lateral to said pancreas and about 2 to about 1 inches superior to said pancreas.

4. The method of claim 1, wherein one of said one or more injection sites is about 1.75 to about 0.75 inches left and lateral to said pancreas and about 2 to about 1 inches superior to said pancreas.

5. The method of claim 1, wherein one of said one or more injection sites is about 3.25 to about 2.25 inches left and lateral to said pancreas and about 3 to about 2 inches superior to said pancreas.

6. The method of claim 1, wherein one of said one or more injection sites is about 1.75 to about 0.75 inches left and lateral to said pancreas and about 3 to about 2 inches superior to said pancreas.

7. The method of claim 1, wherein said administering comprises at least four injection sites.

8. The method of claim 7, wherein a first injection site is about 3.25 to about 2.25 inches left and lateral to said pancreas and about 2 to about 1 inches superior to said pancreas, wherein a second injection site is about 1.75 to about 0.75 inches left and lateral to said pancreas and about 2 to about 1 inches superior to said pancreas, wherein a third injection site is about 3.25 to about 2.25 inches left and lateral to said pancreas and about 3 to about 2 inches superior to said pancreas, and wherein a fourth injection site is about 1.75 to about 0.75 inches left and lateral to said pancreas and about 3 to about 2 inches superior to said pancreas.

9. The method of claim 1, further comprising administering at least three, four or five of said subcutaneous injections of tolerogenic dendritic cells.

10. The method of claim 1, wherein said blood glucose is restored to said pre-diabetic level for between about 65 to about 75 weeks.

11. The method of claim 1, wherein said administering does not comprise administering additional immunosuppressive therapies.

12. The method of claim 1, wherein said administering prevents co-stimulation of a T-cell that is within a radial distance of three cell lengths to said injection site.

13. The method of claim 1, wherein said two or more subcutaneous injections of tolerogenic dendritic cells comprises at least one particle, wherein said particle comprises oligonucleotides comprising the nucleic acid sequence set forth as SEQ ID NO: 4, SEQ ID NO: 5, SEQ ID NO: 6, or SEQ ID NO: 7, or combinations thereof.

14. The method of claim 1 wherein said pediatric mammal has clinical onset of type 1 diabetes for at most 1 month.

15. The method of claim 1 wherein said pediatric mammal is a human.

16. The method of claim 15, wherein said human is between about 1 to about 5 years of age, between about 6 to about 10 years of age, or between about 11 to about 18 years of age.

17. The method of claim 15 wherein said human has pediatric onset of diabetes.

18. The method of claim 1, further comprising:
expanding a suppressive B-cell population in said pediatric mammal, wherein a greater local expansion of suppressive B-cells occurs near said pancreas as compared to a systemic suppressive B-cell expansion.

19. A method for altering a ratio of suppressive B-cells to T-cells to treat type 1 diabetes in a pediatric mammal comprising:
injecting tolerogenic dendritic cells at a site proximal to a pancreas in said pediatric mammal,
wherein said altering comprises increasing said suppressive B-cells and decreasing said T-cells.

20. A method for reducing a blood glucose concentration in a mammal having new-onset diabetes, the method comprising:
selecting said mammal having new-onset diabetes;
administering two or more subcutaneous injections of tolerogenic dendritic cells at one or more injection sites proximal to a pancreas in said mammal,
wherein said blood glucose concentration is reduced to a normal blood glucose concentration for a period of at least twenty four hours in said mammal having said new-onset diabetes, wherein the mammal is a human of less than 18 years of age.

* * * * *

UNITED STATES PATENT AND TRADEMARK OFFICE
CERTIFICATE OF CORRECTION

PATENT NO. : 10,940,164 B2
APPLICATION NO. : 16/297484
DATED : March 9, 2021
INVENTOR(S) : Giannoukakis et al.

Page 1 of 1

It is certified that error appears in the above-identified patent and that said Letters Patent is hereby corrected as shown below:

In the Specification

Column 1, beginning at Line 18, "This invention was made with government support under NIDDK DK063499 and NIDDK DK49835-01, both awarded by the National Institutes of Health. The government has certain rights in this invention." should read --This invention was made with government support under DK063499, and DK049835 awarded by the National Institutes of Health. The government has certain rights in the invention.--

Signed and Sealed this
Twentieth Day of May, 2025

Coke Morgan Stewart
*Acting Director of the United States Patent and Trademark Office*